United States Patent
Chang et al.

(10) Patent No.: US 7,018,331 B2
(45) Date of Patent: Mar. 28, 2006

(54) ENDOSCOPE ASSEMBLY USEFUL WITH A SCOPE-SENSING LIGHT CABLE

(75) Inventors: Huei Liang Chang, Milpitas, CA (US); Richard A. Beutter, San Diego, CA (US)

(73) Assignee: Stryker Corporation, Kalamazoo, MI (US)

(*) Notice: Subject to any disclaimer, the term of this patent is extended or adjusted under 35 U.S.C. 154(b) by 342 days.

(21) Appl. No.: 10/343,375

(22) PCT Filed: Jul. 31, 2001

(86) PCT No.: PCT/US01/24420

§ 371 (c)(1),
(2), (4) Date: Oct. 10, 2003

(87) PCT Pub. No.: WO02/09577

PCT Pub. Date: Feb. 7, 2002

(65) Prior Publication Data

US 2004/0064019 A1    Apr. 1, 2004

Related U.S. Application Data

(63) Continuation-in-part of application No. 09/628,488, filed on Jul. 31, 2000, now Pat. No. 6,689,050, which is a continuation-in-part of application No. 09/131,067, filed on Aug. 7, 1998, now Pat. No. 6,110,107, which is a continuation-in-part of application No. 08/886,955, filed on Jul. 2, 1997, now Pat. No. 5,850,496.

(60) Provisional application No. 60/024,198, filed on Aug. 26, 1996.

(51) Int. Cl.
*A61B 1/07* (2006.01)
*A61B 1/04* (2006.01)
*G02B 6/36* (2006.01)

(52) U.S. Cl. ............... 600/182; 600/178; 600/132; 600/118; 600/112; 385/40; 385/101; 403/27

(58) Field of Classification Search ............... 600/132, 600/118, 109, 178, 182, 110, 112; 385/40, 385/41, 75, 101, 117, 118; 403/27
See application file for complete search history.

(56) References Cited

U.S. PATENT DOCUMENTS 3,942,859 A    3/1976    Korodi (Continued)

FOREIGN PATENT DOCUMENTS

EP    0 027 608    4/1981

(Continued)

OTHER PUBLICATIONS

PCT Application No. PCT/US97/15834, International Preliminary Examination Report, Nov., 1998.

(Continued)

*Primary Examiner*—John P. Leubecker
(74) *Attorney, Agent, or Firm*—Flynn, Thiel, Boutell & Tanis, P.C.

(57) ABSTRACT

An endoscope assembly consisting of an endoscope 622, a light source, 626 and a camera 552 with display 558. The endoscope contains a memory 670 with data that describes the endoscope and its operating characteristics. When the light source is connected to the endoscope with a fiber optic cable 628, the data in the memory are read into a control processor 538a internal to the light source. The control processor, based on the endoscope data configures the light source so that it emits an appropriate amount of light for that endoscope. The light source also sends a control unit 556 of the camera data indicating the type of endoscope to which the camera is attached. Based on this endoscope type data, the control unit processes the image signals generated by the camera head in an appropriate form for the attached endoscope so as to produce appropriate signals for presenting an image on the display.

10 Claims, 36 Drawing Sheets

U.S. PATENT DOCUMENTS

| | | | |
|---|---|---|---|
| 4,325,606 | A | 4/1982 | Ikuno et al. |
| 4,407,272 | A | 10/1983 | Yamaguchi |
| 4,601,284 | A | 7/1986 | Arakawa et al. |
| 4,623,788 | A | 11/1986 | Kern et al. |
| 4,641,915 | A * | 2/1987 | Asakawa et al. ............. 385/26 |
| 4,666,242 | A | 5/1987 | Cairns |
| 4,775,212 | A | 10/1988 | Smith |
| 4,896,939 | A | 1/1990 | O'Brien |
| 5,115,126 | A | 5/1992 | Ams et al. |
| 5,353,147 | A | 10/1994 | Grimes |
| 5,408,263 | A | 4/1995 | Kikuchi et al. |
| 5,460,490 | A | 10/1995 | Carr et al. |
| 5,505,195 | A * | 4/1996 | Wolf et al. ............ 128/203.15 |
| 5,749,885 | A | 5/1998 | Sjostrom et al. |
| 5,850,496 | A | 12/1998 | Bellahsene et al. |
| 5,967,969 | A * | 10/1999 | Enomoto et al. ............ 600/117 |
| 6,068,592 | A * | 5/2000 | Davis .......................... 600/132 |
| 6,092,722 | A | 7/2000 | Heinrichs et al. |
| 6,110,107 | A | 8/2000 | Bellahsene et al. |
| 6,322,496 | B1 * | 11/2001 | Iida et al. .................... 600/118 |
| 6,364,827 | B1 * | 4/2002 | Irion et al. ................... 600/118 |
| 6,436,032 | B1 * | 8/2002 | Eto et al. ..................... 600/117 |
| 6,638,212 | B1 * | 10/2003 | Oshima ....................... 600/109 |
| 6,712,756 | B1 * | 3/2004 | Kura et al. .................. 600/118 |
| 2003/0174205 | A1 | 9/2003 | Amling et al. |

FOREIGN PATENT DOCUMENTS

| | | |
|---|---|---|
| EP | 0 049 477 | 4/1982 |
| EP | 0 416 408 A2 | 3/1991 |
| EP | 0 544 436 | 6/1993 |
| JP | 56-065107 | 6/1981 |
| JP | 57-044116 | 3/1982 |

OTHER PUBLICATIONS

PCT Written Opinion for App. No. PCT/US97/15834 dated Sep. 23, 1998, including Search Report dated Jan. 16, 1998 (11 pages).

Stryker Endoscopy Blueprint of Light Cable Port, Oct., 1996, 3 pages.

Copy of EPO International Search Report for PCT/US01/24420, date Feb. 5, 2002.

Copy of EPO Written Opinion for PCT/US01/24420 dated Jun. 13, 2002.

PCT/US01/24420 International Preliminary Examination Report, Sep. 2002.

* cited by examiner

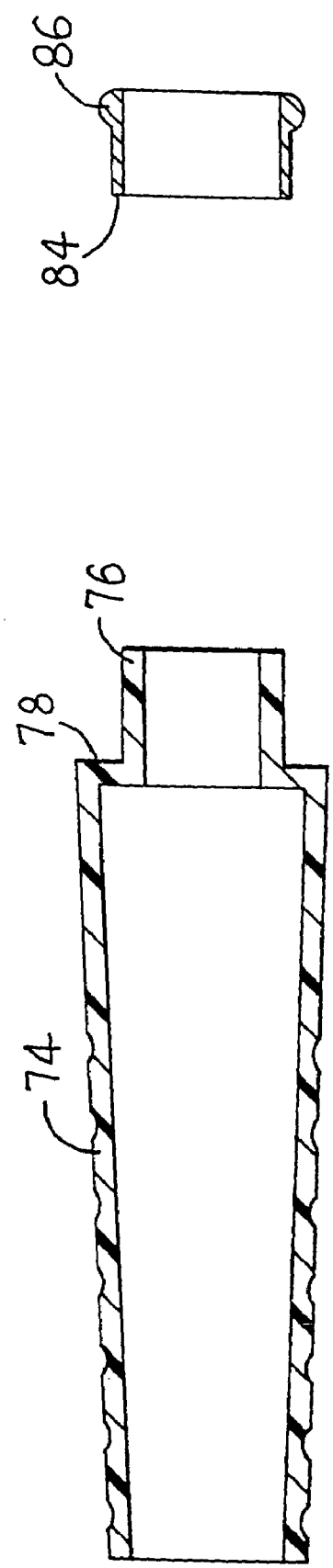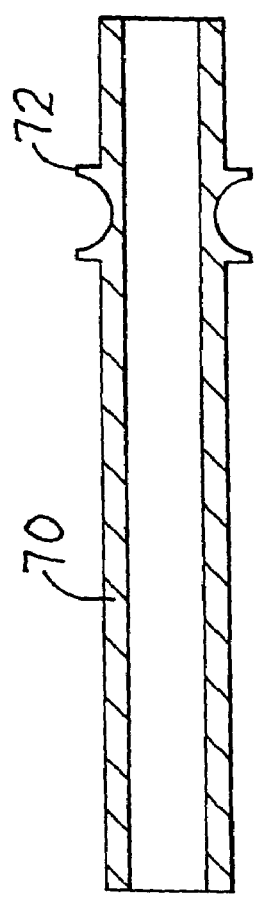

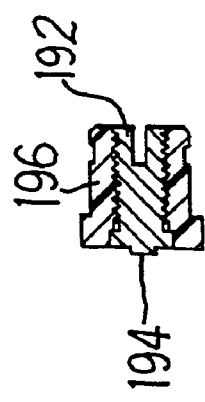
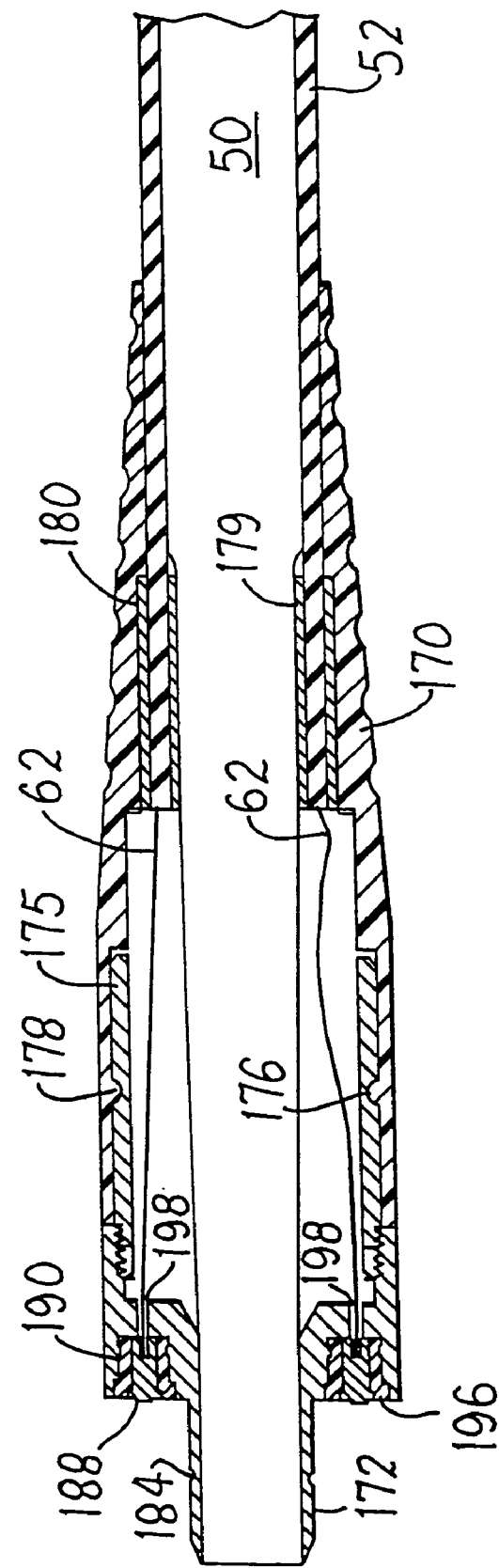
FIG. 14A
FIG. 14

ENDOSCOPE ASSEMBLY USEFUL WITH A SCOPE-SENSING LIGHT CABLE

RELATIONSHIP TO EARLIER FILED APPLICATIONS

This application is a continuation-in-part of U.S. patent application Ser. No. 09/628,488, filed Jul. 31, 2000 now U.S. Pat. No. 6,689,050. Pursuant to 35 U.S.C. Secs. 120 and 365, the Applicants hereby, to the extent possible, claim, for the present application, the filing date of Application Ser. No. 09/628,488, and the applications from which it claims priority. The '488 Application is continuation-in-part of Application Ser. No. 09/131,067, filed Aug. 7, 1998, now U.S. Pat. No. 6,110,107. The '067 Application is a continuation-in-part from Application Ser. No. 08/886,955, filed Jul. 2, 1998, now U.S. Pat. No. 5,850,496. The '955 Application claims priority from United States Provisional Patent Application Ser. No. 60/024,198, filed Aug. 26, 1996. The Applicants hereby incorporate by reference the contents of U.S. Pat. No. 6,110,107, entitled FIBER OPTIC CABLE FOR SUPPLYING LIGHT TO AN ENDOSCOPE AND FOR DETECTING THE PRESENCE OF AN ENDOSCOPE, issued Aug. 29, 2000 and U.S. Pat. No. 5,850,496, entitled, ENDOSCOPE WITH INTEGRATED, SELF-REGULATING LIGHT SOURCE, issued Dec. 15, 1998.

FIELD OF THE INVENTION

This invention relates generally to endoscopes designed to facilitate minimally invasive surgery and, more particularly, to an endoscope with an integrated light source that self-regulates the intensity of the light emitted by the light source.

BACKGROUND OF THE INVENTION

An endoscope is a surgical tool designed to be placed inside a body in order to provide a view of the portion of the body in which it is inserted. In endoscopic surgery, an endoscope is placed in a body at the location at which it is necessary to perform a surgical procedure. Other surgical instruments are placed in the body at the surgical site. The surgeon views the surgical site through the endoscope in order manipulate the other surgical instruments to perform the desired surgical procedure. The development of endoscopes and their companion surgical instruments has made it possible to perform minimally invasive surgery that eliminates the need to make a large incision to gain access to the surgical site. Instead, during endoscopic surgery, small openings, called portals, are formed. One advantage of performing endoscopic surgery is that since the portions of the body that are cut are reduced, the portions of the body that need to heal after the surgery are likewise reduced. Still another advantage of endoscopic surgery is that it exposes less of the interior tissue of the patient's body to the open environment. This minimal opening of the patient's body lessens the extent to which the patient's internal tissue and organs are open to infection.

The ability to perform endoscopic surgery is enhanced by the availability of light sources designed to illuminate the surgical site inside the patient. A typical light source includes a light-emitting bulb that is located outside of the patient in a control console. A fiber optic cable extends between the control console and the endoscope. The cable has a proximal end that is adapted to receive the light emitted by the bulb and a distal end that is coupled to a complementary light post integral with the endoscope. (Hereinafter it shall be understood that "proximal" means towards the light source and "distal" means towards the end of the endoscope positioned at the surgical site.) When the light source is energized, the light emitted by the bulb is transmitted through the cable to the endoscope. A set of optical fibers in the endoscope transmit the light to the surgical site. The emitted light illuminates the surgical site so as to make it easier for surgical personnel to observe the site.

While current light sources have facilitated the advancement of endoscopic surgery, they are not without disadvantages. One particular disadvantage relates to the fact that, in order to illuminate a surgical site, the light source for an endoscopic is required to transmit a large amount of light energy. For example, some of these light sources include light emitting bulbs that is supplied with 250 Watts, have luminous intensity of approximately 2,500 candelas, and an average luminance of 40,000 $cd/cm^2$. Problems arise with these light sources because, during endoscopic surgery, it may be necessary to switch the endoscope that is used on a patient. A change of endoscope may be necessary if, during the surgical procedure, a different field of view of the surgical site is desired; such change in perspective can sometimes only be obtained by switching endoscopes. During this switch of the endoscopes, the distal end of the fiber optical cable is disconnected from the first endoscope and coupled to the second endoscope. Prior to the fiber optic cable being attached to the second endoscope, it is often momentarily placed on a surgical drape. A problem can occur because the light energy emitted by the fiber optic cable can rapidly warm the surface on which the distal end of the cable is placed. If the surface is cloth or paper, such as a surgical drape, there is a potential that this energy may singe the drape. If the fiber optic cable is inadvertently left on the drape for an extended period of time, the heat generated could potentially cause the drape to either burn or ignite.

Moreover, another problem associated with illuminating the surgical site during an endoscopic surgical procedure is that the light directed towards the site invariably changes during the course of the procedure. This change occurs because the endoscope is subjected to both deliberate and involuntary movement during the course of a procedure. When, as a result of this movement, the distal end of the endoscope is moved towards the surgical site, the light it emits focuses on a relatively small surface. If the quantity of received light becomes relatively high, the view of the site is lost due to white-out. If the distal end of the endoscope is moved away from the surgical site, the light emitted diffuses over a relatively large surface. If the amount of light per unit surface area appreciably diminishes, the view of the site significantly darkens. In either situation, the surgeon's view of the surgical site may decay to the point at which it the ability to perform the surgical procedure is hampered. Moreover, even minor changes in the light present at the surgical field may be distracting.

In order to adjust for the problems associated with the changing quantities of light received per unit surface area at a surgical site, many currently available light sources are provided with feedback circuits. These circuits receive an indication of the amount of light that is reflected from the tissue surgical site. This indication typically comes from a camera mounted to the endoscope. Primary, the camera is a transducer that captures the images present at the surgical site in order to facilitate the display and recording of those images. The camera supplies signals representative of light intensity to a feedback circuit internal to the light source. Based on these input signals, the feedback circuit selectively adjusts the amount of the light emitted by the light source. This regulation ensures that the light present at the surgical site remains at a level that ensures the site can be properly viewed.

While the above feedback circuits work reasonably well, there are some limitations associated with current light sources. Specifically, the rate at which feedback adjustments the light emitted by endoscopes occur is a function of the type of endoscope. Often, during a surgical procedure, a surgeon will change the endoscope with which he/she views the surgical site. Presently, each time this change is made, surgical personnel must also manually input commands to the light source or camera in order to provide an indication of the new type of endoscope to which these components are connected. Requiring surgical personnel to perform this procedure can increase the time it takes for the overall surgical task to be accomplished. Moreover, since this procedure is performed manually, there is always the possibility that this procedure will either not be performed, or performed incorrectly. In either situation, until the light source feedback circuit receives a correct indication of the type of endoscope to which the light source is connected, the source may output light that is inappropriate for the endoscope with which it is used.

SUMMARY OF THE INVENTION

This invention relates generally to an improved endoscope with integrated light source designed to reduce the extent to which the light emitted by the light source has the potential for being a thermal hazard in a surgical suite. This invention also relates to a light source capable of receiving a signal representative of the type of light source to which it is connected. Based on this information, the light source of this invention is able to both initially establish the light it emits and the extent and rate at which it adjusts the emitted light. This invention also relates generally to an improved endoscope capable of providing an indication of its specific type.

BRIEF DESCRIPTION OF THE DRAWINGS

This invention is pointed out with particularity in the claims. The above and further advantages of this invention may be better understood by reference to the following description taken in conjunction with the accompanying drawings, in which:

FIGS. 5A, 5B and 5C are cross sectional views of components forming the proximal-end plug of the fiber optic cable;

FIGS. 6A, 6B and 6C are cross sectional views of components forming the distal end plug of the fiber optic cable;

FIG. 14 is a cross-sectional view of the scope-end plug of the cable of FIG. 12;

FIG. 14A is a detailed cross-sectional view of the electrical contact depicted in FIG. 14;

FIG. 22 is an assembly diagram depicting how

FIG. 27 is a cross sectional view of the scope end plug of the cable of FIG. 25;

FIG. 28 is a cross sectional view of the adapter of FIG. 25 taken along line 28—28;

DETAILED DESCRIPTION

Figure 1:
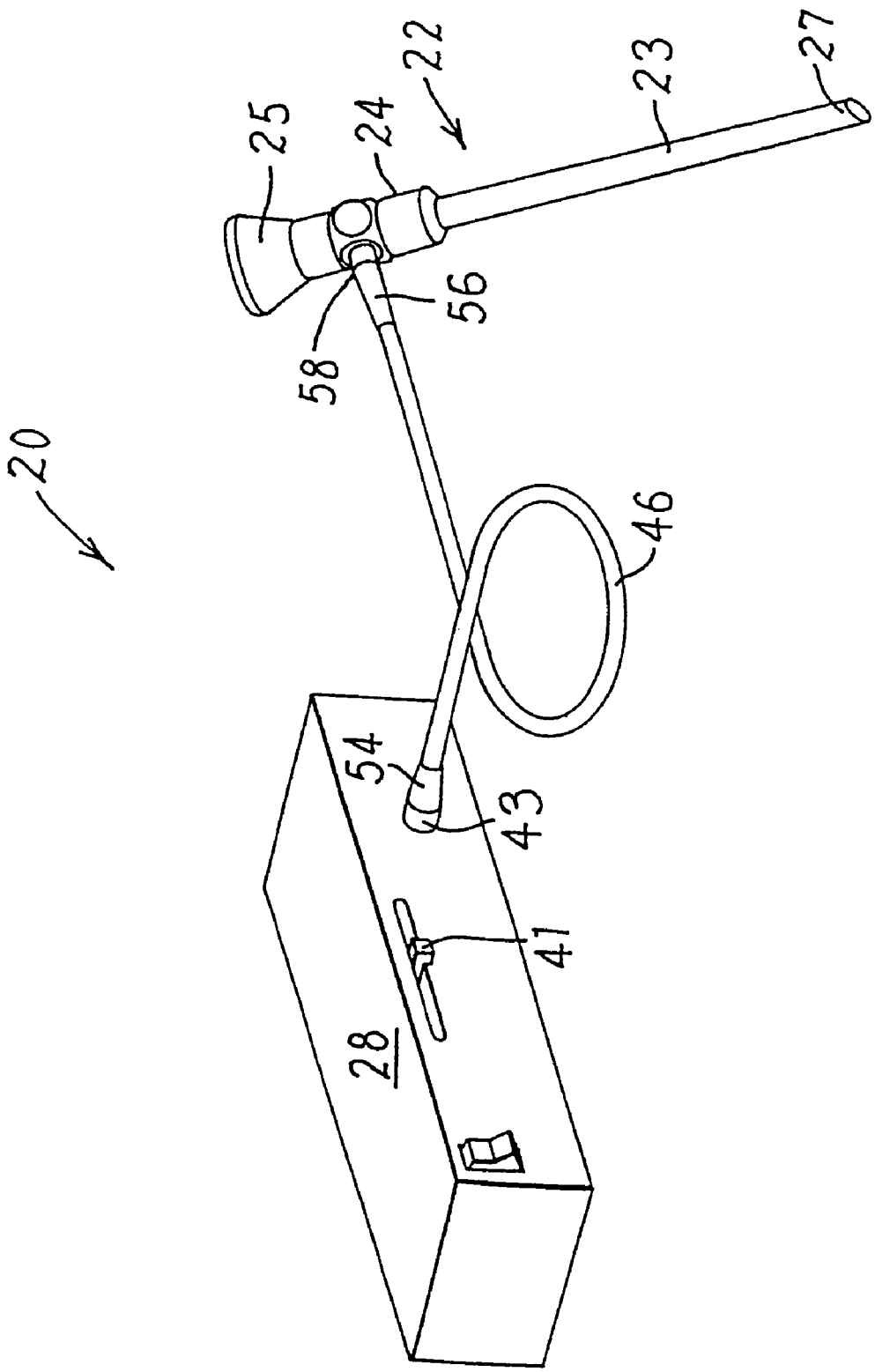
FIG. 1 is block diagram of the main features of the endoscope with integrated light source of this invention.

FIG. 1 illustrates the basic features of the endoscopic system 20 of this invention. The endoscopic system 20 includes an endoscope 22. The endoscope has an elongated hollow shaft 23 with a distal end 27 that is positioned inside the body of the patient. A window, not illustrated covers the distal end of the shaft 23. The shaft 23 also has a proximal end 24 that remains outside of the patient. An eyepiece 25 is fitted over the proximal end 24 to provide a viewing port through which the surgeon views the surgical field. Optical focusing elements, not illustrated, in the shaft 23 serve to enhance the visible field of view. The eyepieces 25 of many endoscopes are designed to hold a television camera. These cameras provide surgical personnel with a view of the surgical site on complementary monitors to which they are connected.

Figure 2:
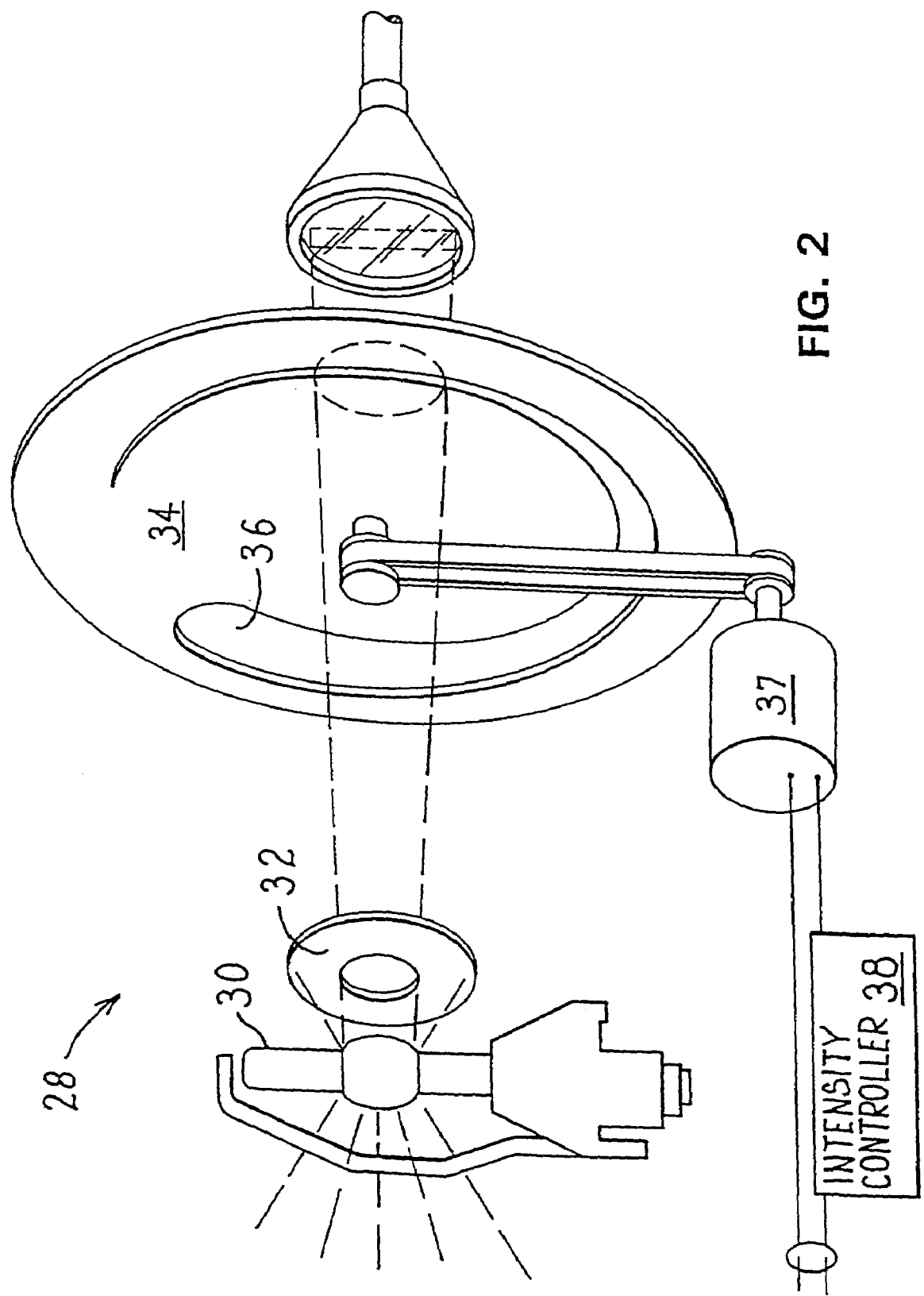
FIG. 2 is a diagrammatic illustration of light bulb and companion intensity controller internal to the light source of this invention.

Endoscopic system 20 includes a light source 28 for illuminating the surgical site. As seen by reference to FIG. 2, light source 28 includes a bulb 30 for emitting light that is used to illuminate the surgical site at which the endoscope 22 is directed. In one preferred version of this invention, bulb 30 is a bulb sold under the trademark HALOMITE as Bulb HTI 250 W/SE. The light emitted by bulb 30 is directed through a focusing ring 32. The light emitted by bulb 30 is directed from ring 32 towards a circular shutter 34 that is rotatingly mounted in the light source 26. Shutter 34 is formed to define a curved aperture 36 immediately inside the perimeter of the shutter that has a variable cross sectional width. The light emitted by bulb 30 is directed towards a fixed location that is offset from the center of shutter 34. By the selective positioning of the aperture 36 relative to the point at which the light is directed, light source 28 controls the intensity of the light emitted therefrom. By selectively positioning shutter 34, a maximum of 100% of the light emitted by bulb 30 to just 5 to 20% of the light emitted can be transmitted from the light source 28. The light emitted by light source 28 is emitted through a socket 43 (FIG. 1).

Shutter 34 is selectively rotated to set the position of aperture 36 by a stepper motor 37. An intensity controller 38 selectively actuates stepper motor 37 in response to user-entered and automatic command signals in order to regulate the amount of light emitted by light source 28. The intensity controller 38 can be controlled by one of two inputs. The light emitted can be controlled manually by the displacement of slide switch 41, e.g. a potentiometer, located on the face of the light source 28.

Alternatively, it is contemplated that the intensity controller 38 may regulate the position of the shutter 34 automatically based on externally generated command signals. These command signals are asserted by a control unit, (not illustrated) integral with the television camera that may be mounted to the eyepiece 25 of the endoscope 22. More particularly, the amplitude of the video signal received from the television camera is used as a feedback signal for controlling the intensity of the light emitted by the light source 28. In this manner, the brightness of the image generated by the television camera inferentially controls the intensity of the light emitted by the light source.

The intensity controller 38 further has a circuit for placing the light source 28 in what is referred to as a standby mode. When the light source 28 is in the standby mode, the signal measured as result of the position of the slide switch 41 or the external command signal is not used to establish the position of the shutter 34. Instead, when the light source 28 is in the stand-by state, intensity controller 38 automatically actuates stepper motor 37 to move the shutter 34 so that only a minimal amount of light is emitted from the light source 28.

Figure 3:
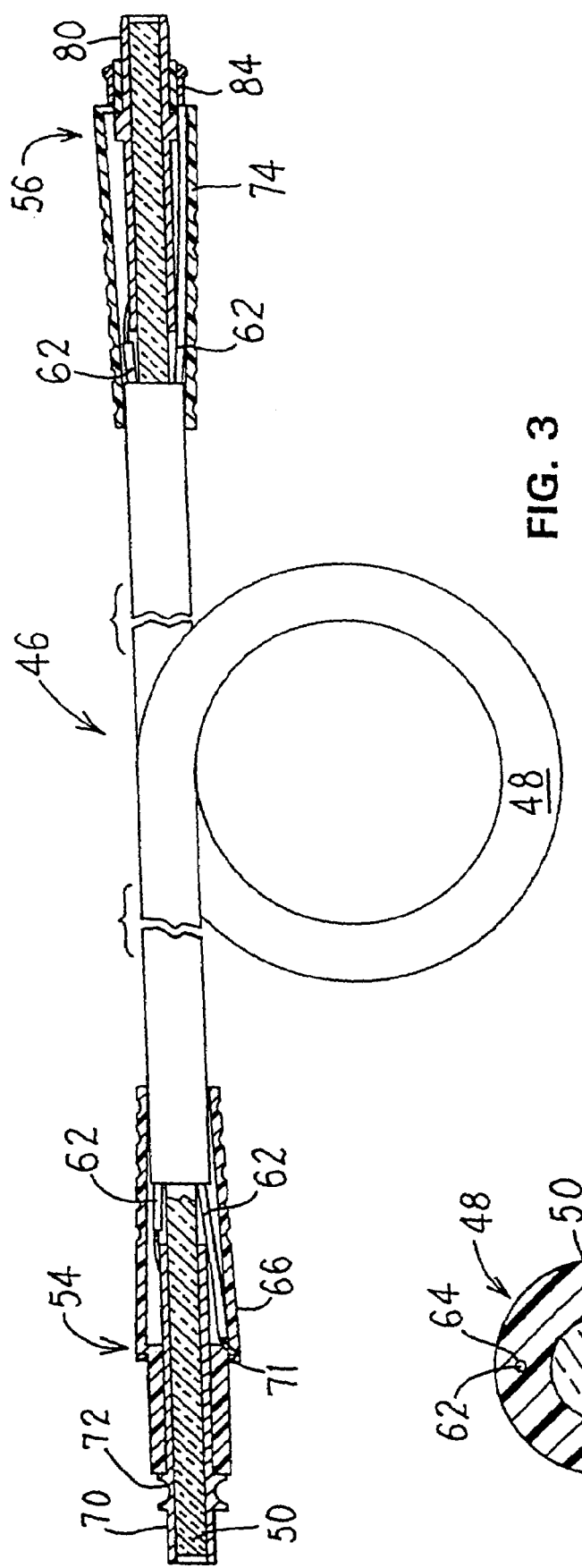
FIG. 3 is a partial plan view of the fiber optic cable with the plugs integral therewith depicted in cross-section.

The light emitted by light source 28 is transmitted to the endoscope 22 over a fiber optic cable 46 coupled to socket 43. Fiber optic cable 46, now described by initial reference to FIGS. 3 and 4, includes a cable body 48 in which there is an elongated core 50 formed out of optically transmissive material. A protective, insulating tubing 52 is disposed around the core 50. In some versions of the invention, tubing 52 is at least partially transparent in order to provide a quick visual indication of the on/off state of the light source and the intensity of the light emitted thereby. One end of fiber optic cable 46 is fitted with a proximal end plug 54 designed to be coupled into light source socket 43. The opposed end of cable body 48 of fiber optic cable 46 is fitted with a distal end plug 56. Distal end plug 56 is designed to be fitted into a complementary light post 58 integral with the shaft 23 of the endoscope 22 adjacent eyepiece 25 (FIG. 1). Fiber optical cables internal to the shaft 23 forward the light to the distal end of the shaft, cables not illustrated.

Fiber optic cable 46 further includes two insulated electrical conductors 62 over which a signal is applied to provide light source 28 with an indication of whether or not the cable 46 is attached to an endoscope 22. Conductors 62 each of which is insulated, extend the length of cable body 48. In the depicted version of the invention, each conductor 62 is contained in an individual conduit 64 formed in the tubing 52 of the cable.

As seen by reference to FIGS. 3, 5A, 5B and 5C proximal-end plug 54 includes a plastic, insulating outer body 66 that is fitted over the adjacent end of cable body 48. The outer body 66 of proximal-end plug 54 includes a sleeve-like head 68 that projects beyond cable body 48. A small annular step 69 defines the separation of the main portion of the plug outer body 66 from head 68. A metallic head sleeve 70 is fitted inside head 68 of outer body 66 so as to extend outside of head 68. In the illustrated version of the invention, head sleeve 70 is formed with a ring 72 that extends around the sleeve 70 adjacent the forward end of the head 68 of plug outer body 66. Ring 72 is formed with a concave profile designed to facilitate the seating therein of conventional spring loaded balls associated with light source socket 43. The proximal end of cable core 50 appears at the open end of head sleeve 70.

A first one of the conductors 62 of fiber optical cable 46 is electrically connected to the end portion of head sleeve 70 disposed in the main portion of the outer body 66 of the plug 54. The second conductor 62 extends through a small opening in the step portion 69 of plug outer body 66. The second conductor 62 electrically attached to a metallic, conductive, washer-like ring 71 that is seated against the outer surface of step 69.

As seen by reference to FIGS. 3, 6A, 6B and 6C, distal-end plug 56 includes a plastic, insulating outer body 74 that is fitted over the adjacent end of cable body 48. The outer body 74 of distal-end plug 56 includes a sleeve-like head 76 that projects forward of both cable body 48 and the main portion of outer body 74. A small annual step 78 defines the separation of the main portion of the plug outer body 74 from head 76. A metallic, conductive head sleeve 80 is fitted inside head 68 of outer body 48 so as to extend outside of head 76. In the illustrated version of the invention, head sleeve 80 is formed with a collar 82 that has a rectangular cross sectional profile. Head sleeve 80 is seated in the outer body 74 of plug 56 so that the leading surface of collar 82 bears against the inside surface of step 78. The most forward end of cable core 52 appears at the open end of head sleeve 80.

A sleeve-like coupling ring 84 formed of a conductive metal is fitted around the outside of the head 76 of the outer body 74 of plug 56. A lip 86 with an outwardly directed, convex cross sectional profile is formed integrally with the forward end of coupling ring 84. The coupling ring 84 is designed to engage a complementary locking tongue associated with endoscope 22. A first one of the conductors 62 of fiber optical cable 42 is electrically connected to an end portion of head sleeve 80 disposed in the main portion of the outer body 74 of the plug 56. The second conductor 62 extends through a small opening in the step portion 78 of plug outer body 74. The second conductor 62 is electrically attached to coupling ring 84.

Socket 43 of the light source 28 is now described by reference to FIGS. 7–10. Socket 43 includes an adapter plate 82 fitted over the front face of the light source 28. Adapter plate 82 is formed with an opening 83 through which the light generated by bulb 30 and passed through the shutter 34 is emitted. A cylindrical knob body 84 is fitted over adapter plate 82 so as to be centered over opening 83. Knob body 84 is formed with a center bore 85 that extends axially therethrough. A tubular base 86 is fitted inside the bore 85 of knob body 84. Base 86 is further provided with a circumferential flange 87 around the proximal end thereof that is secured against adapter plate 82. A spring 88 is located in the bottom of the base. A tube like spring hat 89 is located above spring 88. Base 86 is further formed with four circular openings 91 spaced 90 degrees apart from each other that are located adjacent the forward edge of the spring hat 89. A ball bearing 92 is seated in each one of the openings 91. Knob body 84 is formed with a rectangular groove 93 for receiving the outer portions of bearings 92.

A plastic seating ring 94 is located around the exposed open end of bore 85 of knob body 84. A metal, conductive contact washer 95 is fitted in the top of seating ring 94. More particularly, washer 95 is seated in a groove 96 formed in the outermost surface of seating ring 94. A circular knob adapter 98 functions as the outer member of socket 43. Knob adapter 98 has a center opening 102 designed to accommodate the head portion of proximal-end plug 54.

When proximal-end plug 54 is seated in socket 43, ball bearings 92 seat in the concave space defined by ring 72 of head sleeve 70 so as to lock the plug in the socket. When proximal-end plug 54 is so positioned, the metal surface of head sleeve 70 is in contact with the adjacent inside metal surface of spring hat 89. Conductive ring 71 of plug 54 is in contact with conductive washer 95 of socket 43. Wires, not illustrated, extending from spring hat 89 and conductive washer 95 provide an electrical connection from these members to intensity controller 38.

A similar socket-like assembly is disposed on the light post 58 of endoscope 22. In some preferred versions of the invention, this assembly is actually an adapter arranged to be removably secured to the light post 58. More particularly, this socket or adapter includes a conductive, tube-like member against which the outer surface of head sleeve 80 abuts. There is also one or more conductive locking members designed to be positioned against the lip 86 of coupling ring 84 in order to hold distal-end plug 56 to the endoscope 22. A conductor extends between the member against which head sleeve 80 abuts and the lock member(s) that engage coupling ring 84.

The endoscopic system 20 of this invention is used in the manner similar to which conventional endoscopic systems are used. The light generated by the source 28 is supplied to the endoscope 22 through the fiber optic cable 46. As long as the cable 46 remains attached to the light source 28 and the distal plug 56 is plugged into the adaptor fitted to the light post 58 the endoscope 22 a closed circuit is established across conductors 62 integral with the cable 46. The monitoring circuit internal to the intensity controller 38 is preferably an electronic circuit that detects the voltage across conductors 62 as an indication that the cable 46 is plugged into the endoscope. Consequently, the monitoring circuit asserts a signal to the intensity controller that releases the intensity controller from the stand-by state. This allows the controller 38 to set the intensity of the emitted light up from the minimal setting based on either manual controls or the signals from the television system.

If, however, the distal plug 56 of the cable 46 is disconnected from the endoscope 22, the connection across conductors 62 is broken. The monitoring circuit detects this open circuit state as an indication that the fiber optical cable 46 has been disconnected from the endoscope 22. Consequently, the monitoring circuit asserts a signal to intensity controller 38 that causes the intensity controller to go into the stand-by state. The intensity controller then automatically actuates stepper motor 37 so as to cause the resetting of the shutter 34 to a low light emission state. As a result of this resetting of the shutter, only a relatively small amount of light is emitted by the light source 28.

When distal plug 56 of cable 46 is plugged back into an endoscope, the connection across conductors 62 is reestablished. The complementary monitoring circuit reasserts the signal to intensity controller 38 indicating the establishment of the endoscope connection. Once this signal is again received, the intensity controller is released from the stand-by state. In some versions of the invention, the light source is only released from the stand-by state by the subsequent manual actuation of a stand-by release switch on the face of the light source. Once the intensity controller is released from the stand-by state, the intensity controller again actuates the stepper motor 37 so as to return the shutter 34 to its previous aperture position. The return of shutter 34 to its initial position causes the light source to emit the same amount of light as it previously emitted.

The endoscopic system 20 of this invention provides a convenient means of providing light to a surgical site at which an endoscope is placed. An advantage of this system is that it prevents the light source 28 integral with the system from emitting large amounts of light unless the light is being applied to the complementary endoscope 22. Thus, if in the course of surgery, the light source is disconnected from the endoscope 22, the light source, without any command required by surgical personnel, will automatically reduce the amount of light it sends through the associated fiber optic cable 46. Consequently, during this disconnect period, the distal plug 56 of the fiber optic cable can be placed on a surface without risk that the plug (or more precisely the light cable distal tip) may singe or burn the surface. Moreover, since only a minimal amount of light energy is being emitted by the fiber optic cable when so disconnected, the possibility that surgical personnel handling the plug will inadvertently burn their hands is likewise reduced.

Moreover, once the fiber optical cable 46 is reconnected to an endoscope, the intensity controller 38 automatically adjusts the shutter 34 so that the light source will again emit the same amount of light as it did before it was disconnected. Thus, the endoscopic system of this invention provides a means for applying light to the surgical site at which it is used and that prevents light from being emitted when it is not needed. This eliminates the possibility that unneeded light at the distal end plug can be the source of potentially damage-causing thermal energy.

Figure 11:
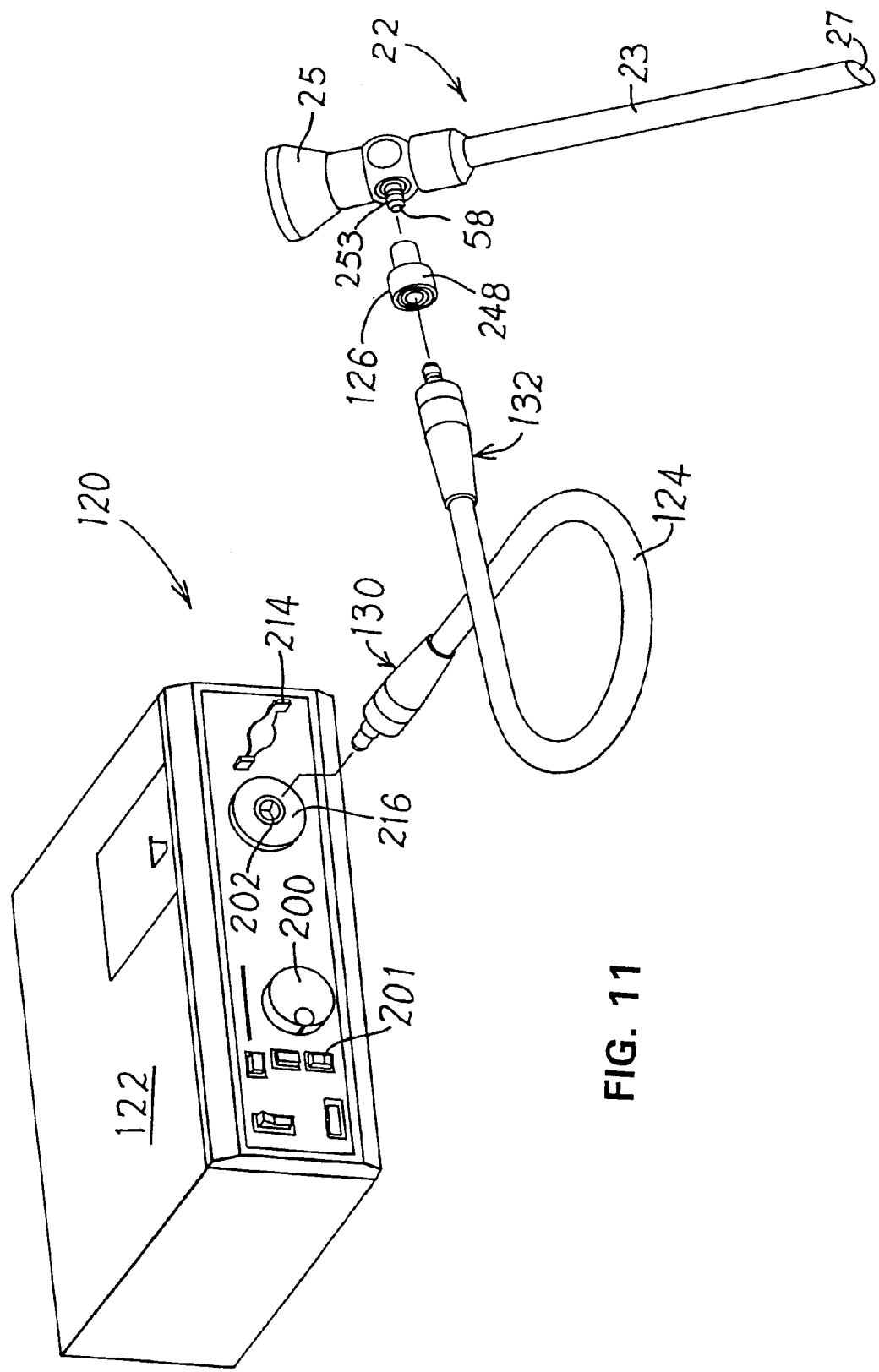
FIG. 11 depicts an alternative endoscope with integrated light source system of this invention.

FIG. 11 illustrates still another endoscope system 120 of this invention. System 120 includes the previously described endoscope 22. In this Figure, the light post 58 distal from the eyepiece through which the illuminating light is supplied to the endoscope 22 is depicted. The illuminating light for the endoscope 22 is supplied by a light source 122 through fiber optic cable 124. The light transmitted by the cable 124 is supplied to the endoscope 22 through an adapter 126 fitted over light post 58.

Figure 4:
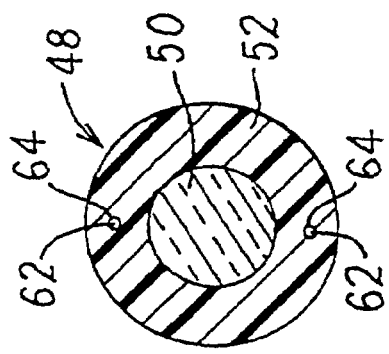
FIG. 4 is a cross sectional view through the center of the fiber optic cable.
Figure 5A:
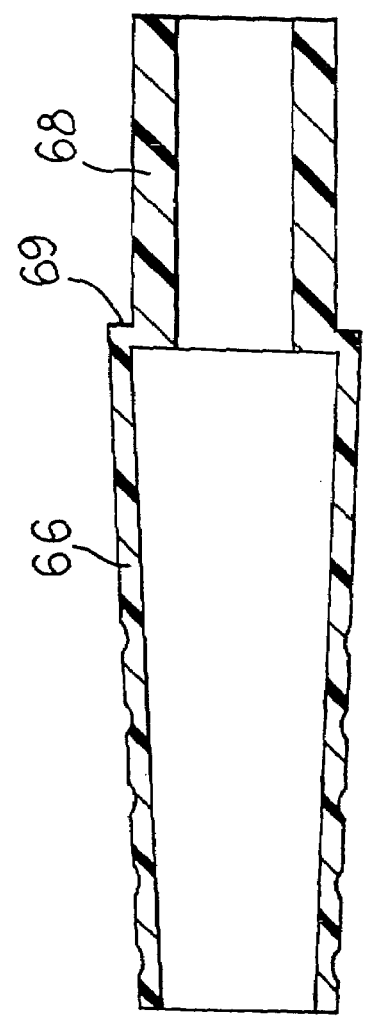
Figure 5C:
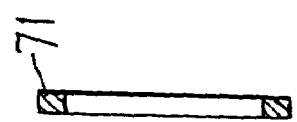
Figure 6B:
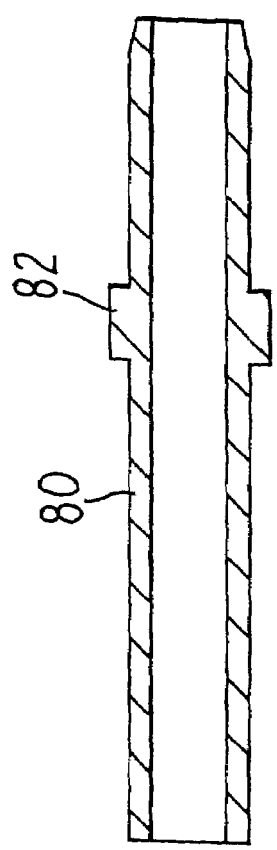
Figure 8:
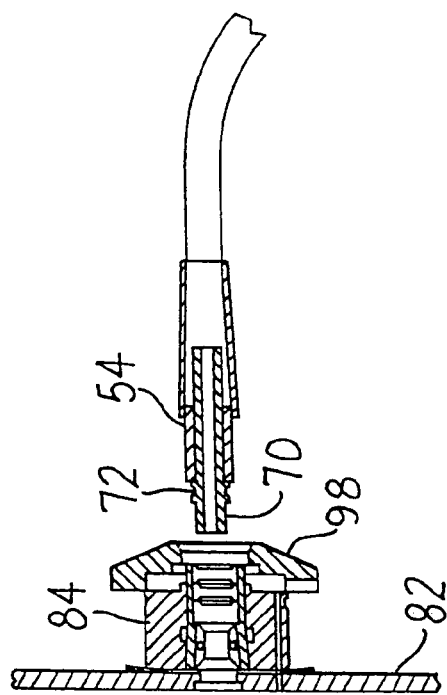
FIG. 8 is a cross sectional view illustrating how the fiber optic cable is coupled to the socket integral with the light source.
Figure 7:
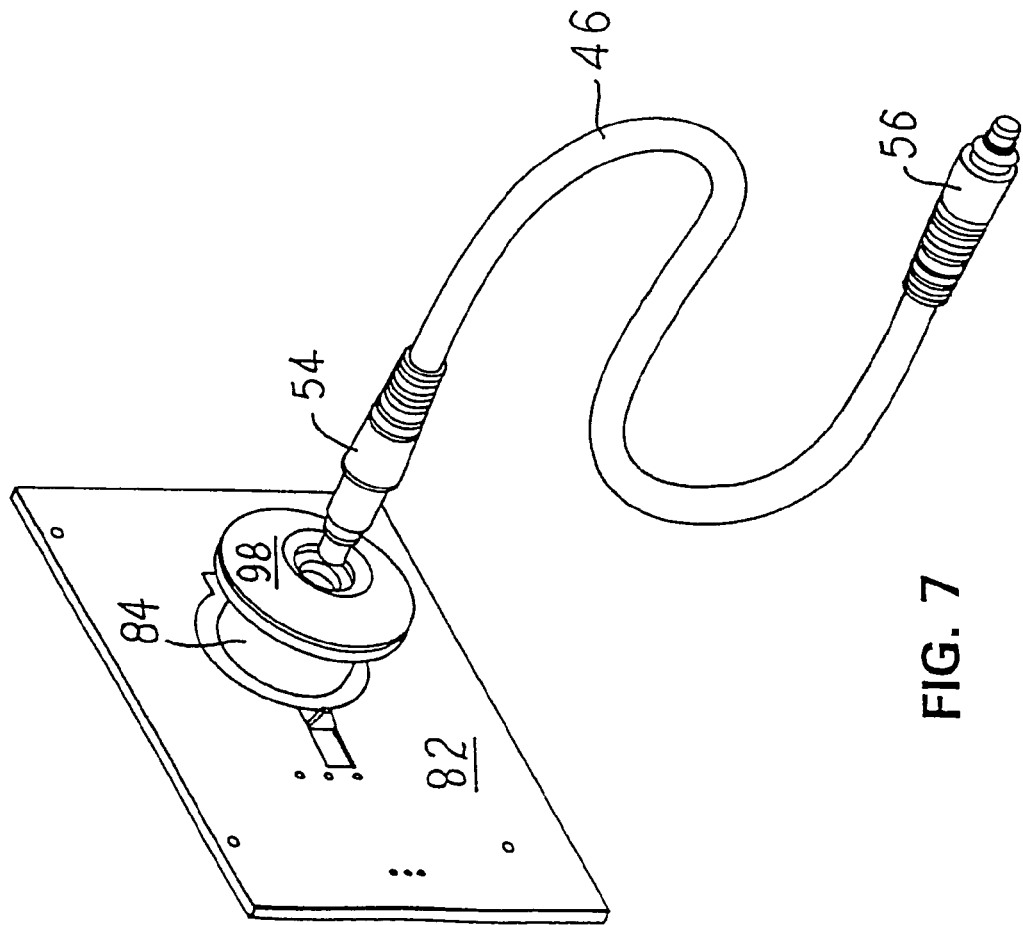
FIG. 7 is a plan view illustrating how the fiber optic cable is coupled to the socket (light cable port) integral with the light source.
Figure 10:
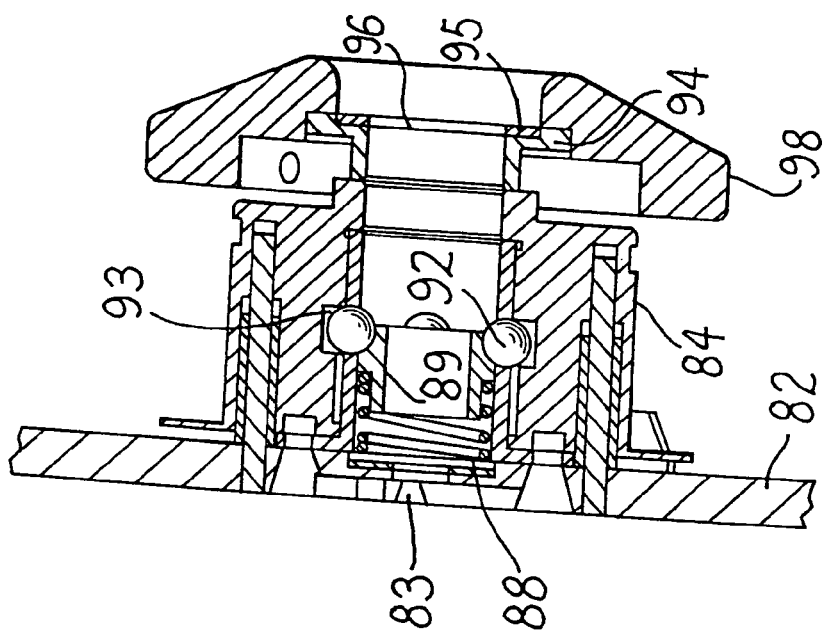
FIG. 10 is a cross sectional view of the socket integral with the light source.
Figure 9:
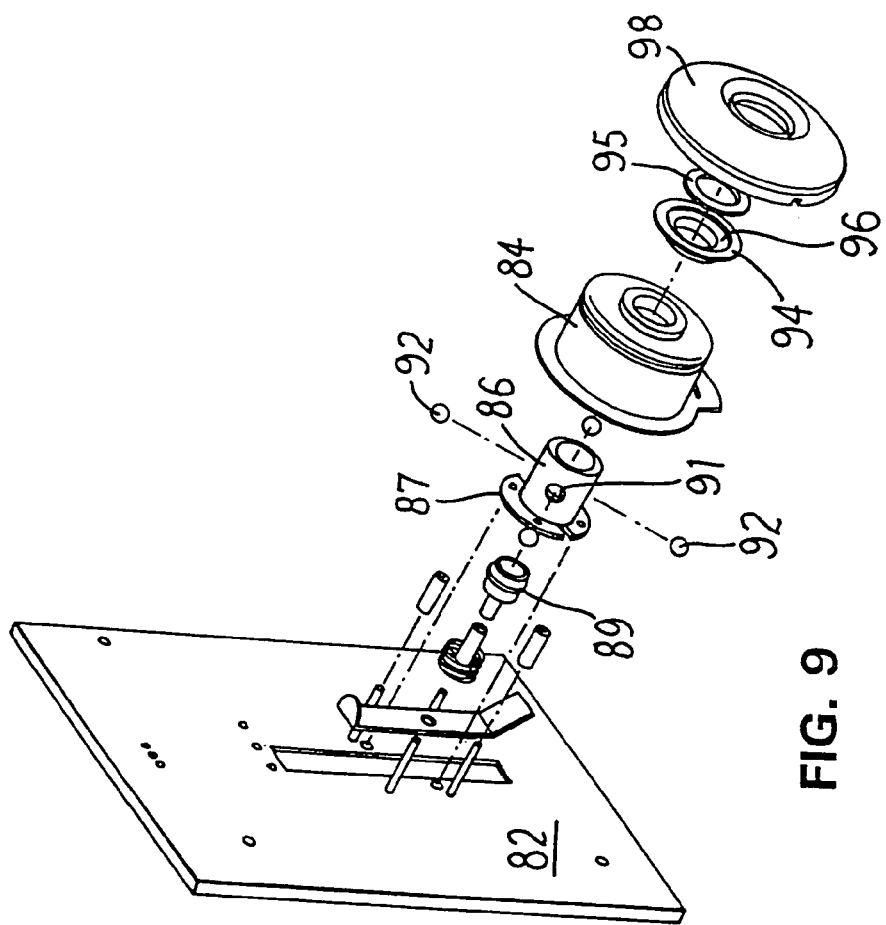
FIG. 9 is an exploded view of the components forming the socket integral with the light source.
Figure 12:
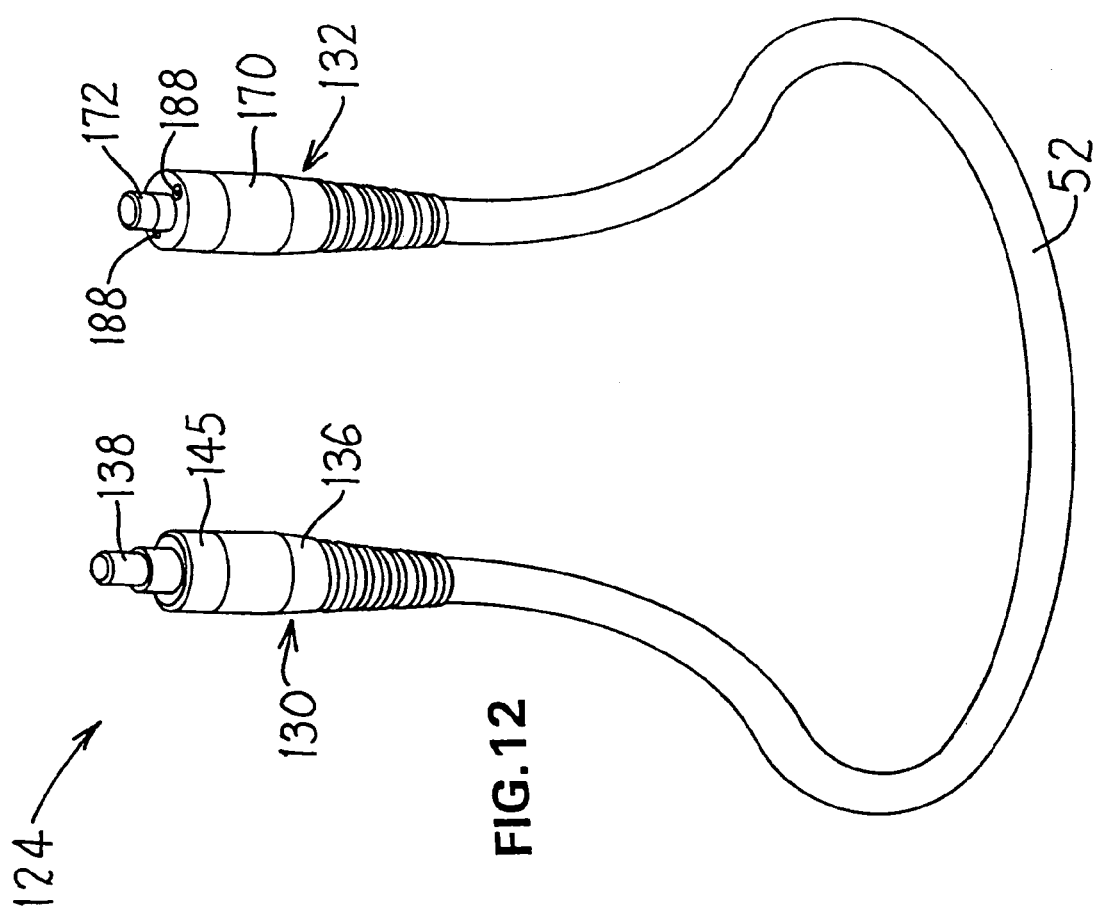
FIG. 12 is a perspective view of the light cable employed in the system of FIG. 11.

Cable 124 of this version of the invention, as seen by reference to FIGS. 4 and 12, includes elongated core 50 (FIG. 4) of optically transmissive material. The core 50 is covered with insulating tubing 52 that is ideally optically transmissive. In some versions of the invention, tubing 52 is formed out of silicone. Embedded in tubing 52 at diametrically opposed positions are two conductors 62. In one preferred version of the invention, conductors 62 are 26-gauge insulated wire. A light end plug 130 forms a proximal end of the cable 124; this plug is coupled to light source 122. A scope end plug 132 forms the opposed distal end of cable 124. Scope end plug 132 is the portion of the cable 124 that is plugged into adapter 126.

Light end plug 130, now described by reference to FIGS. 12 and 13, includes handle 136 formed from silicone that is fitted around the end of insulating tubing 52. The handle 136 is the portion of the light end plug 130 a person grasps to insert/remove the plug from light source 122. A light input tip 138 formed of stainless steel or other electrically conductive material is seated in the handle 136 and extends forwardly therefrom. The light input tip 138 is the mechanical component of plug 130 that covers the portion of the core 50 that extends forward of the handle, the portion that is seated inside the light source 122. Light input tip 138 is more specifically formed to have a stem section 140, that functions as the most forward extending portion of the cable. Immediately distal to stem section 140, light input tip 138 is formed with an intermediate section 142 that has an outer diameter greater than that of the stem section. Light input tip 138 is also formed with a tail section 143. Tail section 143 has an outer diameter slightly greater than that of stem section 140 and less than that of intermediate section 142. As will be described hereinafter, the tail section 143 of light input tip 138 extends approximately two-thirds the distance through handle 136. It will be further observed that the portion of tail section 143 adjacent intermediate section 142 is formed with threading 144 for a purpose to be discussed hereinafter.

A cap 145, also formed of stainless steel other conductive material, is located adjacent the open end of handle 136 so as to extend around light input tip 138. The light input tip 138 and the cap 145 are electrically insulated from each other by a sleeve 147 formed from an electrically non-conductive material, typically a plastic able to withstand the high heat and humidity of surgical sterilization (temperature, approximately 270° F., humidity approximately 100%). It is believed that the sleeve can be formed out of an acetal resin plastic sold under the trademark DELRIN.

The cap 145 itself is shaped to have a sleeve-shaped main body 146 that extends circumferentially around the outer surface of sleeve 147. Main body 146 is shaped to define a flat circular face 148 that extends in a plane perpendicular to the longitudinal axis of the cap 145. The face 148 of the cap 145 is the most proximal positioned surface of the cap. Cap main body 146 also has a circumferentially extending outer surface 141 that is located distally relative to face 148. Cap outer surface 141 is flush with the adjacent outer surface of the handle 136. It will further be understood that cap 145 is shaped so that face 148 has an inner diameter of approximately 0.560 inches and an outer diameter of approximately 0.750 inches. The significance of these dimensions shall become apparent in the following discussion of how cable 124 is coupled to light source 122.

The inner surface of sleeve 147 is provided with threading 149 that engages light input tip threading 144 for holding the sleeve to the light input tip 138. The inner surface of the cap main body 146 and the outer sleeve 147 are provided with complementary threading 150 and 151, respectively, to facilitate the securement of the cap 145 to the sleeve.

A ferrule 152 is threadedly secured to an inwardly stepped distal portion 153 of cap main body 146. Handle 136 is compression fitted around ferrule 152. To facilitate that coupling of the ferrule 152 and the handle 136, the outer surface of the ferrule is formed with a groove 167 in which a complementary semi-circular profile annular flange 154 integral with the handle 136 is seated. It will further be observed that inside the handle adjacent the end of tubing 52 there is first inner sleeve 156 between the core 50 and the tubing. A second, outer sleeve 158 is located between the tubing 52 and the adjacent surface of the handle 136. Sleeves 156 and 158 are formed of plastic to provide reinforcing strength around the end of the tubing 52.

Scope end plug 132, as seen by reference to FIGS. 12, 14, 14A and 15, includes its own silicone handle 170 that serves as a handgrip for the plug. The scope end plug is further provided with scope end tip 172 formed of stainless steel that is partially seated in handle 170 and extend distally therefrom. More particularly, scope end tip 172 has a relatively wide diameter base section 174 that is seated around the open end of handle 170. Extending distally from base section 174, scope end tip 172 has a stem section 176 in that extends distally out of the handle 170. Fiber optic core 50 is fitted inside stem section 176.

A ferrule 175 is threading secured to an inner wall of scope end tip base section 174 so as to extend proximally, therefrom (towards light source 122). Ferrule 175 is compression fitted into handle 170. To facilitate the securement of the ferrule 175 to the handle 170, the ferrule is provided with an annular groove 176 around the outer surface thereof. Handle 170 is provided with a flange 178 around its inner surface that seats in groove 176. A groove 184 is formed around the outer surface of stem section 176.

It will further be observed that inside scope-end plug 132 an inner sleeve 179 is located between the end of tubing 52 and core 50. An outer sleeve 180 is located between the tubing 52 and the handle 170. Sleeves 179 and 180 are formed from plastic.

Seated inside the base section 174 of scope end tip 172 there are two diametrically opposed contacts 188 formed from stainless steel or other conductive material. Each contact 188 has a solid, cylindrical base 192 as well as a reduced diameter solid boss 194. The bosses 194 extend away from base 192 so as to project distally away from the adjacent surface of the scope end tip base section 174.

Contacts 188 are seated in diametrically opposed holes 190 formed in the base section 174 of scope end tip 172. More particularly, each contact is seated in a sleeve-like insulator 196 that is secured in one of the holes 190. Pilot bores 198 that extend coaxially from holes 190 base section 174 serve as conduits through which conductors 62 are routed to the contacts 188.

Figure 23:
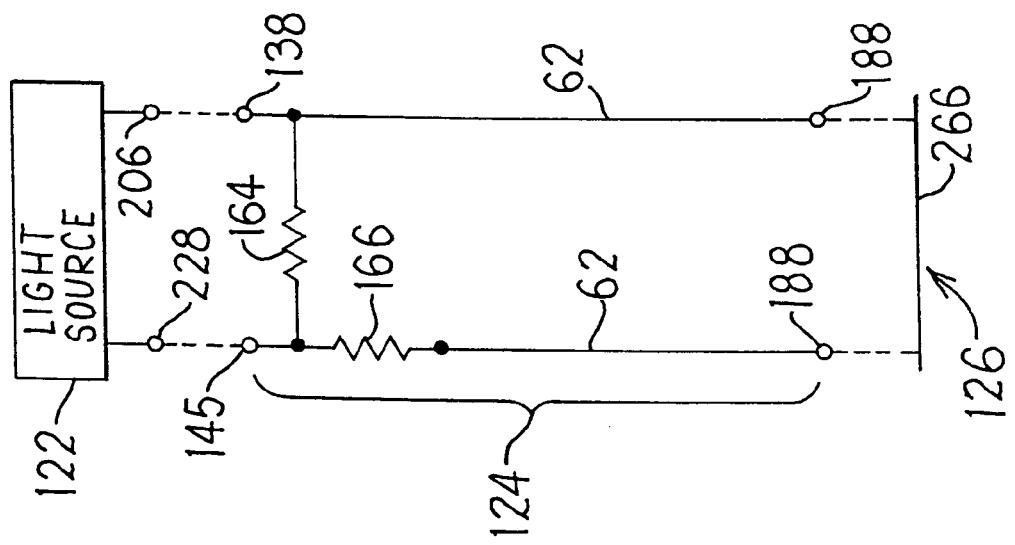
FIG. 23 is a schematic drawing of the conductors and other electrical components integral with the light cable and a representation of how the light cable is electrically connected to the light source and adapter.

FIG. 23 is a schematic drawing illustrating the conductors 62 and other electrically conducting components integral with light cable 124. A resistor 164, which is part of a resistor network, is connected between the light input tip 138 and cap 145. (Light input tip 138, cap 145 and contacts 188 are represented as terminals in FIG. 23.) A resistor 166, also part of the resistor network, extends from the junction of cap 145 and resistor 164. One of the conductors 62 is series connected between the free end of resistor 166 and one of the contacts 188. A second of the conductors 62 extends from the junction of resistor 164 and light input tip 138 to the second of the contacts 188. In some versions of the invention, resistors 164 and 166 have resistances of between 10K and 1 MEG $\Omega$ and are approximately equal in resistance. In still more preferred versions of the invention, resistors 164 and 166 have a resistance between approximately 100K and 220K $\Omega$.

Physically, resistors 164 and 166 are disposed in a void space within light end plug handle 136. Silicone potting material is used to fill the space around resistors 164 and 166 to provide form to the plug 130.

Figure 16:
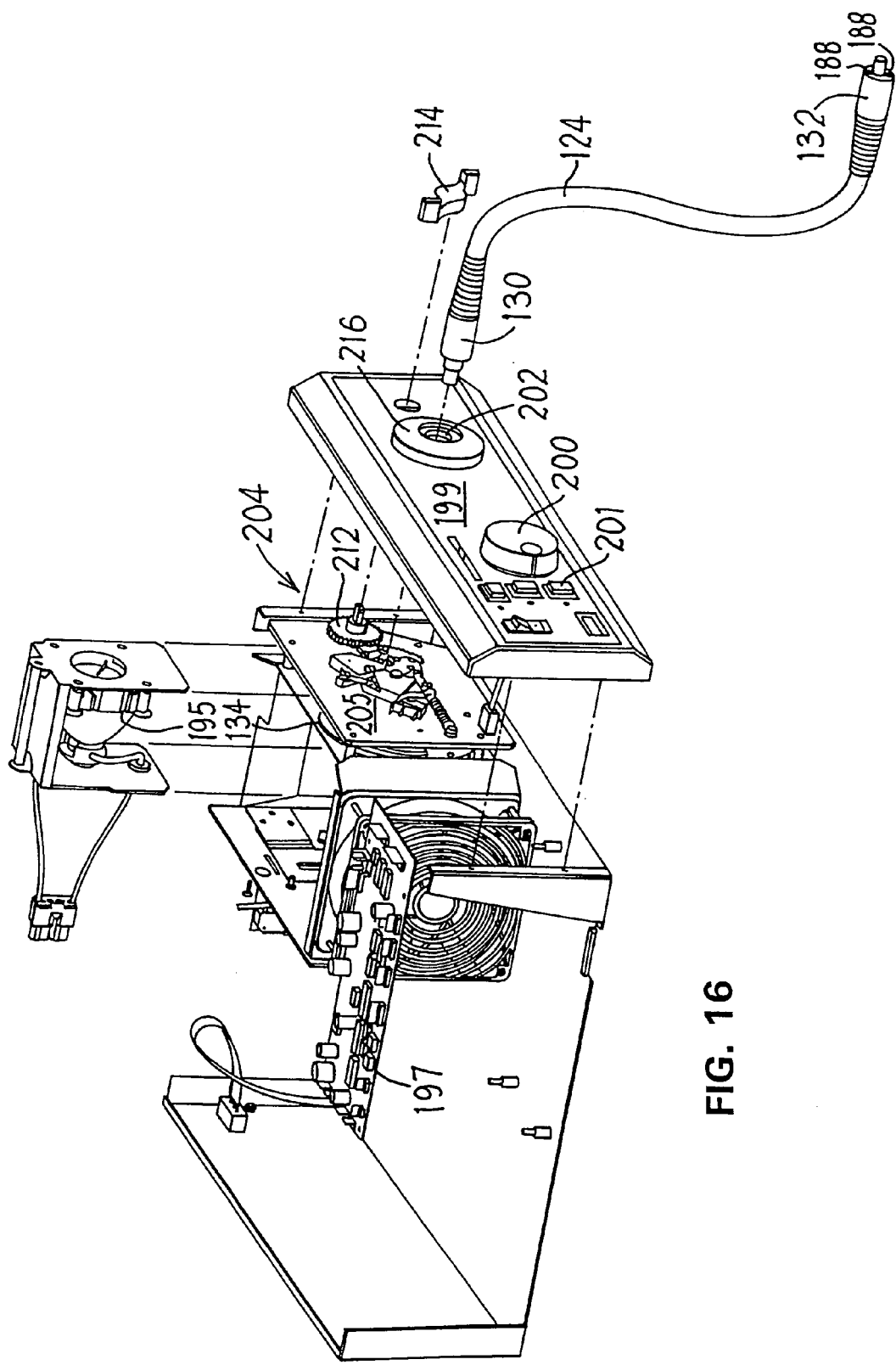
FIG. 16 is an exploded view of the alternative light source.

Light source 122, now described by reference to FIGS. 11, 16 and 17 includes a lamp 195 for emitting the light used to illuminate the surgical site. The intensity of the light emitted by lamp 195 is controlled by the previously described adjustably positionable shutter 34. Also integral with the light source is an intensity control circuit 197 for controlling the actuation of the motor 37 (FIG. 2) that controls the position of the shutter 34.

The brightness of light emitted by light source 122 is manually set by actuation of an intensity control knob 200 disposed outside of a face plate 199 of the light source. Light source 122 is manually placed in/removed from the standby state by the depression of a control switch 201 also on the face plate 199. The placement of the light source in the standby state results in the actuation of the motor 37 so as to cause shutter 34 to be placed in the position wherein only a minimal amount of light is emitted from the light source.

The light end plug 130 of cable 124 is releasably secured in a socket 202 of the light source 122. Socket 202 includes a clamp assembly 204 mounted to a jaw plate 205 located immediately rearward of face plate 199. Clamp assembly 204 includes three jaws 206 that are pivotally mounted to jaw plate 205. Each jaw 206 is formed from a conductive metal such as aluminum and is shaped to have two flat surfaces, not identified. When clamp assembly 204 is in the fully closed state, the flat surfaces of the jaws 206 abut each other. The opening of the clamp assembly 204 causes the jaws 206 to move apart from each other. The jaws 206 are interconnected together for synchronous motion by a jaw gear 208 and a set of arms 210. A spring 211 connected between jaw plate 205 and one of the arms 210 urges the clamp assembly 204 towards the closed state.

The open/closed state of the clamp assembly 204 is controlled by a hub gear 212 rotatably secured to jaw plate 205 that engages jaw gear 208. The hub gear 212 is manually rotated by a release knob 214 mounted outside of the light source face plate 199. When a cable 122 is inserted in the socket 202, release knob 214 is rotated to spread the jaws 206 apart. After the light end plug 130 of the cable 122 is inserted in the socket 202, knob 214 is rotated to open the jaws 206 so that they can be then clamped around the stem of the light input tip 138.

A microswitch 213 is mounted to jaw plate 205 so as to be adjacent one of the jaws 206. The open/closed state of microswitch 213 is controlled by the open/closed state of clamp assembly 204. When the clamp assembly 204 is closed, the adjacent jaw 206 is spaced from the wiper of the microswitch, wiper not illustrated, and the microswitch is in the open state. Once the clamp assembly 204 is opened to accommodate a light cable, the jaw 206 adjacent microswitch 213 abuts the wiper so as to close the microswitch. In some preferred embodiments of the invention, microswitch 213 is positioned so that it closes upon the clamp assembly 204 being opened enough to hold a cable with a tip at least 0.125 inches in diameter, the smallest diameter for a conventional light cable.

It will further be observed that there is a wire 215 that extends from one of the jaws 206. Wire 215 is connected to the jaw 206 to the intensity control circuit 197. Thus, when a jaw abuts the metal of the light input tip 138, the tip is connected to the intensity control circuit 197.

Figure 19:
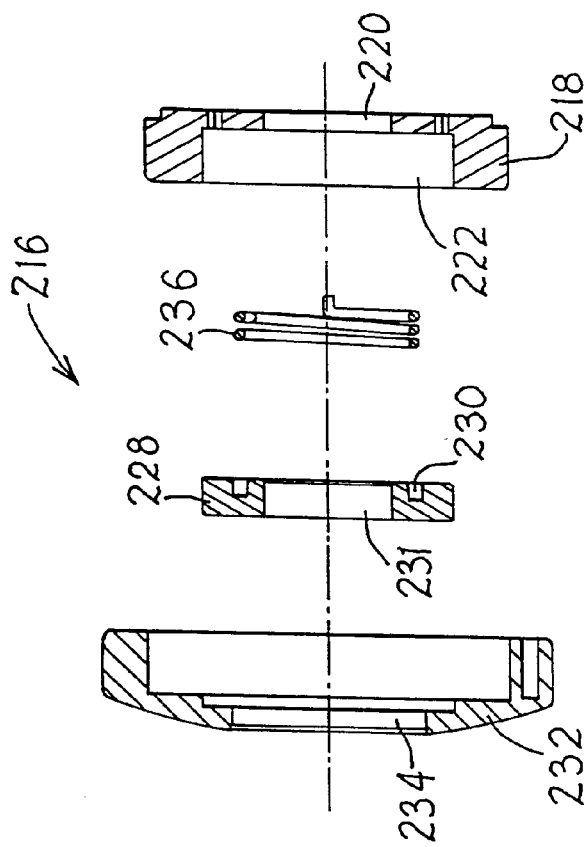
FIG. 19 is a cross-sectional view of the knob assembly of FIG. 18.
Figure 18:
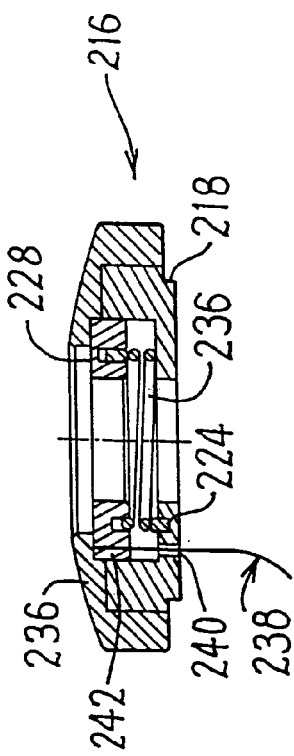
FIG. 18 is an exploded cross-section view of the knob assembly integral with the light source in which the cable is inserted.

Socket 202 also includes a knob assembly 216, seen best in FIGS. 18 and 19, that is secured to the face plate 199 of the light source through which the light input tip 138 extends. Knob assembly 216 includes a circular insert 218 that is secured to the outer surface of face plate 199. Insert 218 is formed from non-conductive material such as DEL-RIN. Insert 218 is shaped to have a center opening 220 through which the light input tip 138 extends. There is also a large, outwardly directed counterbore 222 around center opening 220. The surface of the insert that defines the base of counterbore 222 is formed with a groove 224.

A contact ring 228 formed of brass or other electrically conductive material, is seated in the counterbore 222 of insert 218. It will be noted that in the depicted version of the invention, the surface of the contact ring 228 that faces inwardly is formed with a groove 230. It will be further understood that contact ring 228 is shaped to have a center opening 231 with a diameter of between approximately 0.650 and 0.750 inches. The contact ring 228 is so dimensioned so that a conventional cable, a cable that does not have scope-sensing circuitry, can be secured in socket 202 without physically contacting ring 228. Most conventional cables light-transmitting cables are provided with light end plugs that have outer diameters less than the diameter of opening 231 of contact ring 228.

Ring 228 is held in place by a non-conductive knob 232 that is compression secured over insert 218. Knob 232 is formed with an opening 234 to allow the scope end plug 130 to be inserted therein. Nevertheless, it will be noted that the portion of the knob 232 that defines opening 234 subtends the outer perimeter of contact ring 228 to hold the ring in position.

Contact ring 228 is outwardly biased by a spring 236 located between the ring and insert 218. The turns of the spring 236 located at the opposed ends thereof are located in grooves 224 and 230 of, respectively, the insert 218 and the contact ring 228. An electrical connection between the intensity control circuit 197 and conductive ring 228 by a conductor 238. Insert 218 is provided with a through hole 240 to allow conductor 238 to extend therethrough. Conductive ring 228 is provided with a bore 242 to facilitate the securement of the conductor 238 to the ring.

Figure 20:
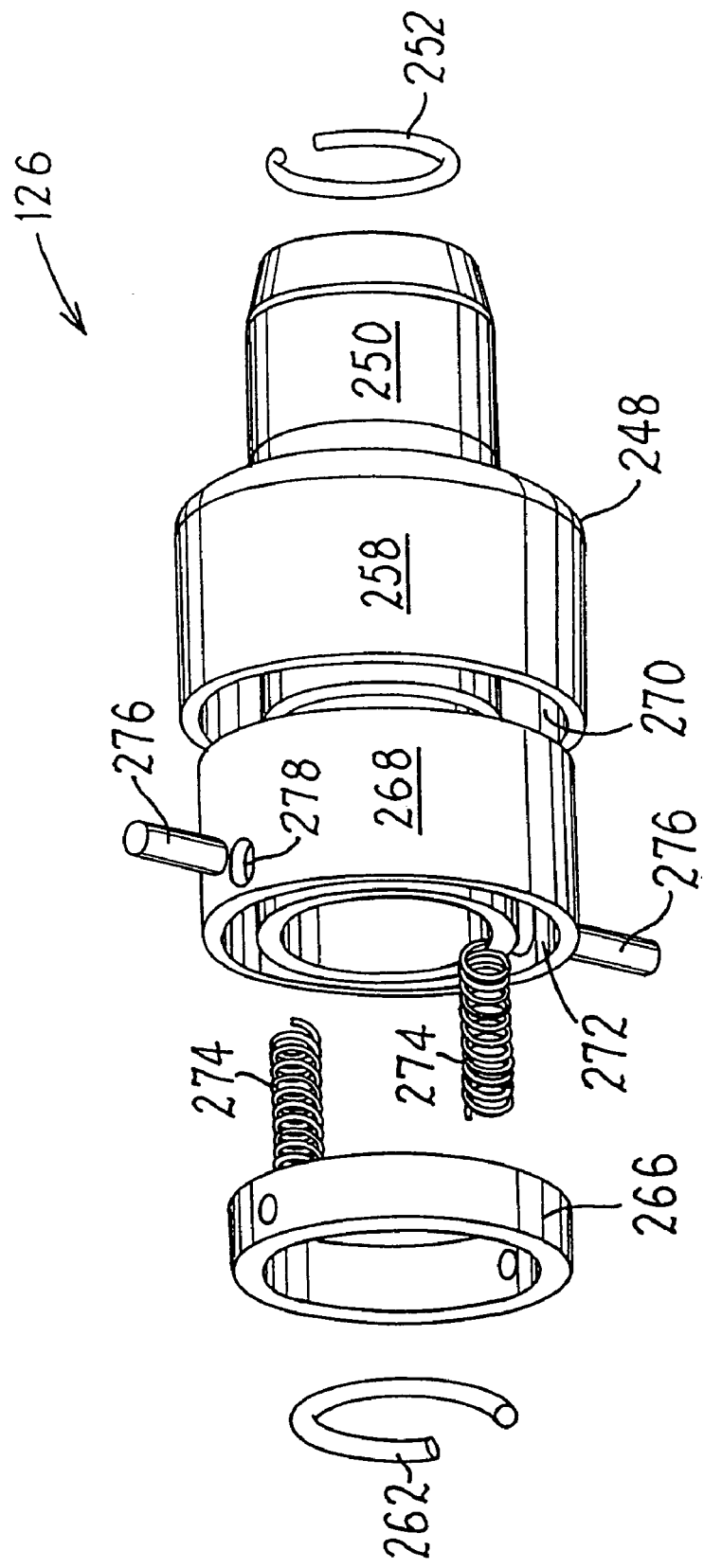
FIG. 20 is an exploded view of the components forming the adaptor fitted to the endoscope.
Figure 21:
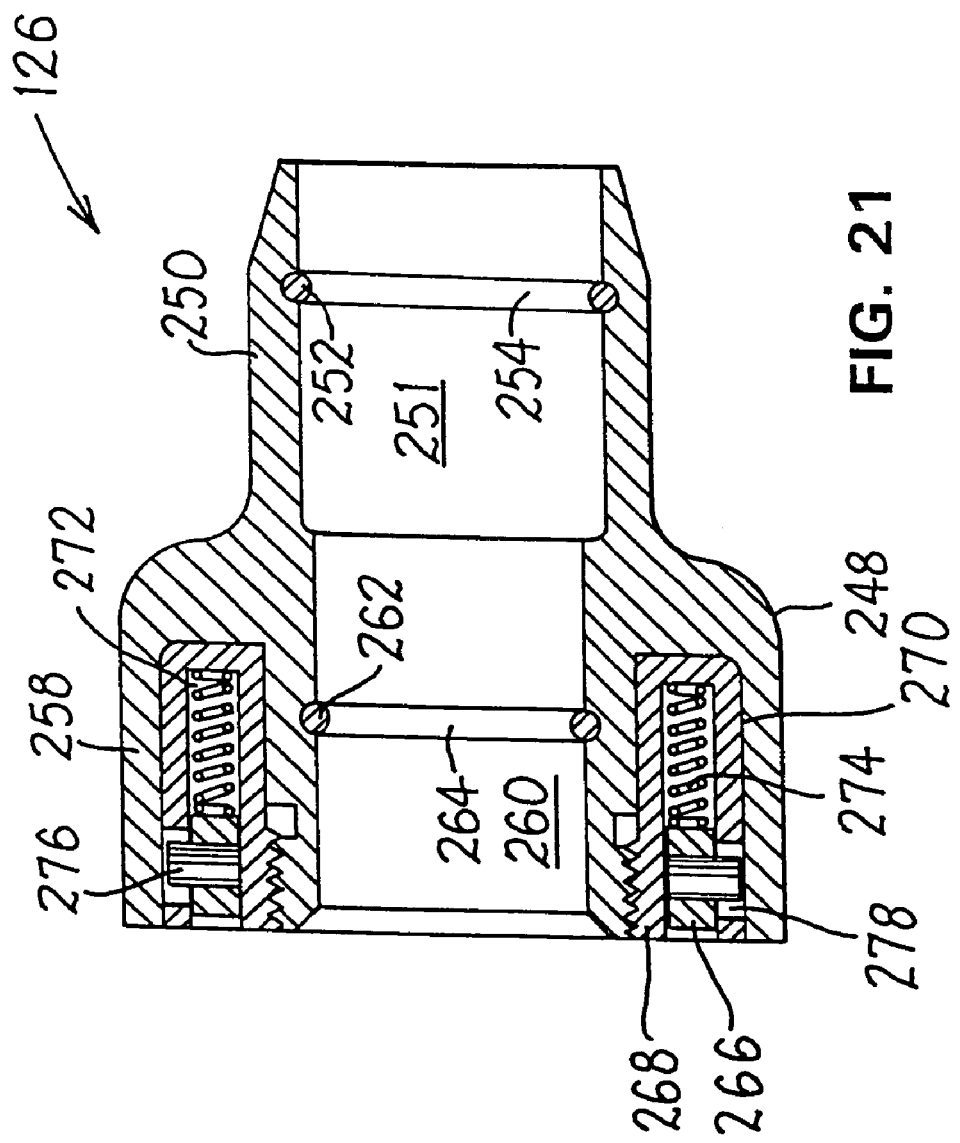
FIG. 21 is a cross-sectional view of the adaptor of FIG. 20.

The adapter 126 to which the scope end plug 132 is secured is now described by reference to FIGS. 20, and 21. Adapter 126 includes a body shell 248 formed of metal that has a scope end 250 fitted over the light post 58 of the endoscope 22. Scope end 250 is formed to define a scope bore 251 having a diameter that is a function of the outer diameter of the complementary light post 58. A split-O-ring snap ring 252 is fitted in a groove 254 formed around the inner wall of the body shell 248 that defines scope bore 251. When the adapter 126 is fitted over light post 58, snap ring 252 seats in a complementary groove 253 (FIG. 11) around the outer diameter of the light post 58 to hold the adapter to the light post.

Body shell 248 is further formed to have a plug end 258 with a diameter greater than that of the scope end 250. Plug end 258 has a plug bore 260 coaxial with and in direct communication with scope bore 251. Plug bore 260 is dimensioned to accommodate the scope end tip 172 of scope end plug 132. A split-O-ring snap ring 262 is seated in groove 264 formed in the inner wall of body shell 248 that defines plug bore 260. When the scope end plug 132 is coupled to the adapter 126, snap ring 262 seats in groove 184 formed in the stem section 176 of scope end tip 172.

Adapter 126 further includes a circular contact ring 266 for establishing a short circuit between contacts 188. Contact ring 266 is seated in insulator 268 that is disposed in the proximal end of body shell 248. More particularly, the open face of plug end 258 of body shell 248 is formed with an annular channel 270 in which the sleeve-like insulator 268 is threadedly secured or press fitted. Insulator 268 is formed from a non-conductive, sterilizable plastic such as is sold under the trademark ULTEM by the General Electric Company.

The outer, proximal, face of the insulator 268 is shaped to have a groove 272 in which contact ring 266 is seated. Contact ring 266 is outwardly biased towards the scope end plug 132 by a pair of springs 274 seated in groove 272 of insulator 268. Outward movement of contact ring 266 is limited by two opposed pins 276 also formed from ULTEM plastic. Pins 276 extend through openings 278 formed in the outer wall of insulator 268 and through bores 280 formed in contact ring 266. It will be observed that opening 278 of the insulator 268 have an oval profile so as to allow the longitudinal movement of contact ring 266 relative to the insulator. In the absence of any opposing force, the springs 274 bias the contact ring 266 so it projects a slight distance away from the insulator 268.

Figure 22A:
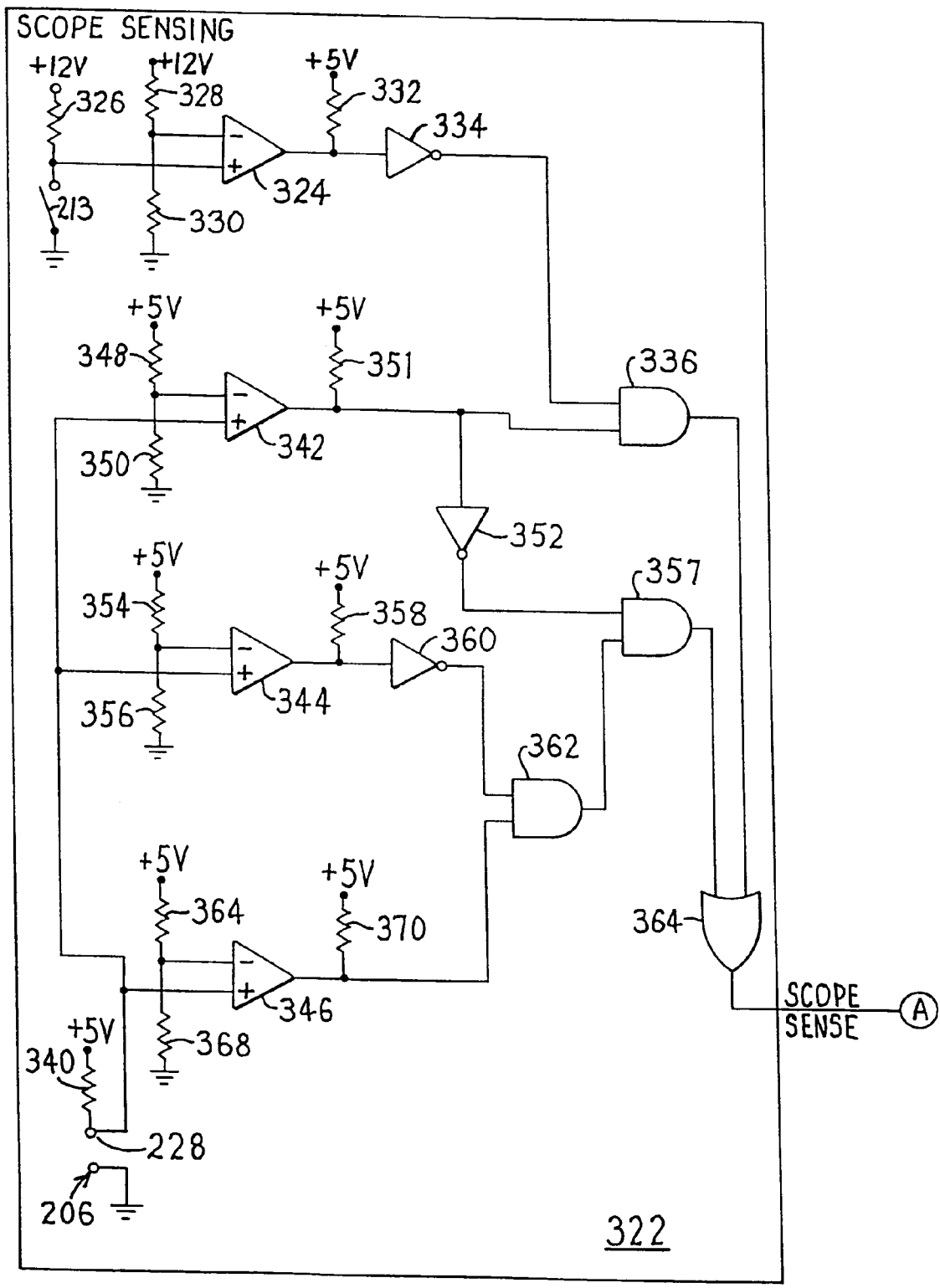
FIGS. 22A and 22B are arranged together to form a schematic and block diagram of the intensity control circuit 197 internal to the light source.
Figure 22B:
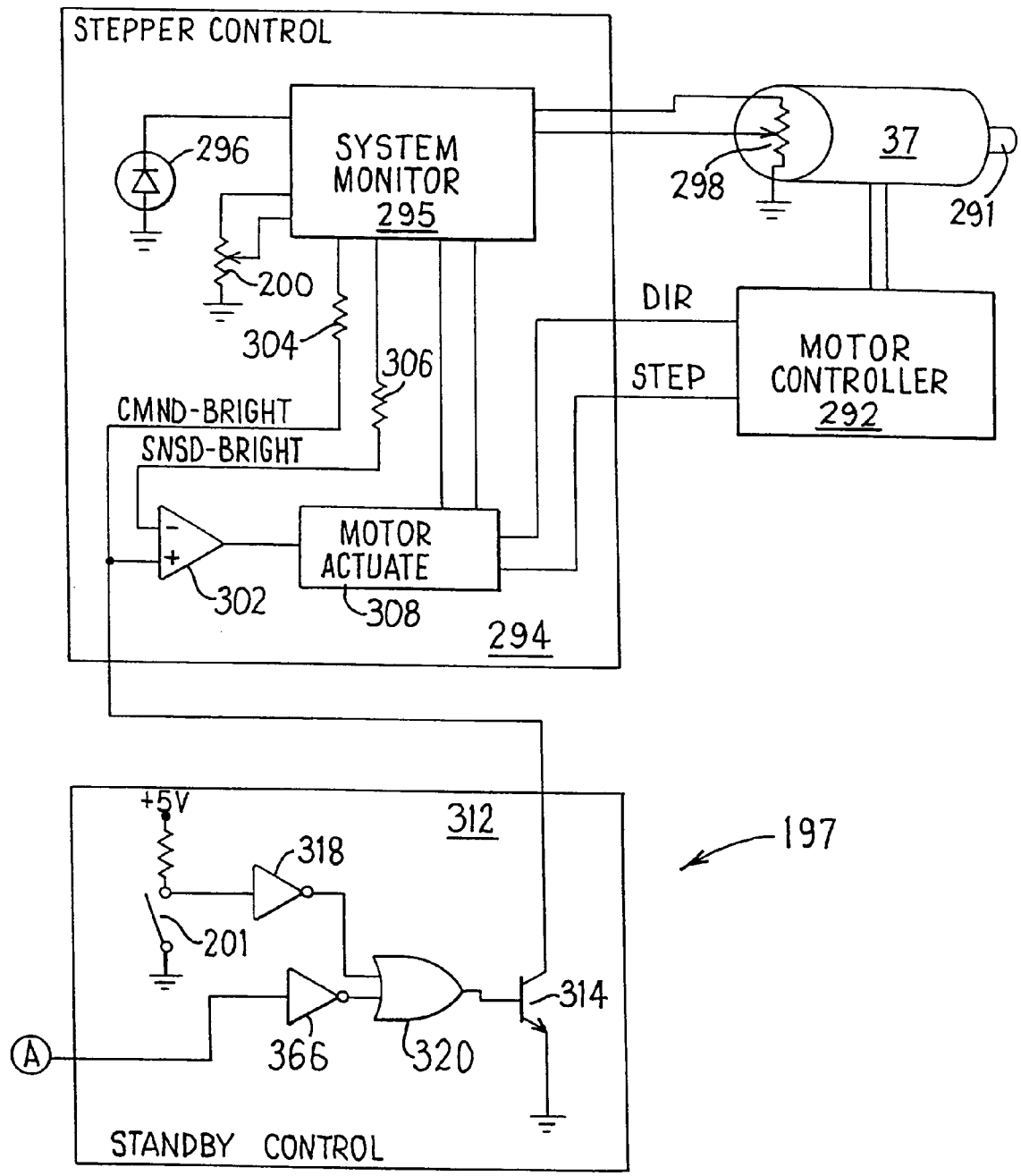

The intensity control circuit 197 internal to light source 122 that controls the actuation of stepper motor 37 is now described by reference to FIGS. 22A and 22B. Intensity control circuit includes a motor controller 292 that actually applies controls the application of commutation currents to the internal windings of motor 37 so as to cause the desired displacement of the motor rotor 291 and shutter 34 (FIG. 2) connected thereto. Integral with many motor controllers 292 is an actual motor controller chip, (not illustrated,) that actually ties the motor windings to voltage source and ground so as to cause current flow through the windings. In some preferred versions of the invention, a UC3517 motor controller integrated circuit chip manufactured by Unitrode is employed in motor controller 292.

Motor controller 292 actuates the motor based on signals received by a stepper control 294. More particularly, stepper control 294 provides motor controller 292 with DIRECTION (DIR) and STEP signals. The DIRECTION signal provides an indication if current is to be applied to the motor 37 to cause rotor 291 movement in either the clockwise or counterclockwise direction. The STEP signal is the actual signal that is asserted to provide an indication that the motor is to be actuated.

When the light source 122 is not in the standby mode, stepper control 294 regulates motor actuation based on signals produced by a system monitor 295. The system monitor 295 monitors signals, other than those related to the standby mode, that are produced by the light source 122. In particular, system monitor 295 monitors the signal produced by the user actuation of intensity control knob 200, herein represented as potentiometer. System monitor 295 also receives a luminosity signal representative of the light present at the surgical site. The signal is received from a photosensitive transducer, represented by photosensitive diode 296, integral with the video camera that receives the light transmitted from the surgical site through endoscope 22. The system monitor 295 is also tied to a sensor integral with motor 37, sensor representative by potentiometer 298, that provides a signal representative of the rotation of the motor rotor 291.

Based on the received input signals, system monitor produces two output signals, a COMMAND BRIGHTNESS (CMND-BRGHT) signal and a SENSED-BRIGHTNESS signal (SNSD-BRGHT) signal. The COMMAND-BRIGHTNESS signal is representative of the user-desired intensity of the light that should be emitted by the light source. The SENSED-BRIGHTNESS signal is representative of the measured brightness. Both BRIGHTNESS signals are adjusted in real-time based on the feedback signals received from the motor 37, intensity control knob 200 and the photosensitive transducer 296.

The COMMAND-BRIGHTNESS and SENSED-BRIGHTNESS signals are applied, respectively to the noninverting and inverting inputs of a master comparator 302 also integral with stepper control 294. More particularly, it will be noted that the COMMAND-BRIGHTNESS signal is applied to master comparator 302 through a resistor 304 and the SENSED-BRIGHTNESS signal is applied through a resistor 306. The output signal produced by master comparator 302 is applied to a motor actuate circuit 308. The motor actuate circuit 308 also receives certain supplemental control signals produced by the system monitor 295. Based on the signals it receives, motor actuate circuit 308, in turn, selectively asserts the DIRECTION and STEP signals to the motor controller 292 so as to cause the actuation of the motor 37.

Intensity control circuit 197 also includes a standby control circuit 312. Standby control circuit 312 is connected to stepper control circuit 294 for causing the actuation of the motor so as result in the shutter 34 being set to its minimal-light-out position regardless of the states of the COMMAND- and SENSED-BRIGHTNESS signals. In the illustrated version of the invention, standby control circuit 312 includes an NPN transistor 314 with a collector tied to the noninverting input of master comparator 302 and an emitter tied to ground. When transistor 314 is turned on, the noninverting input of master comparator 302 is tied to ground. The application of this "zero" voltage signal to comparator 302 causes the comparator to assert a signal that in turn causes motor actuate circuit 308 to assert DIRECTION and STEP signals that result in the actuation of the motor 37 so that shutter 34 is rotated to the minimal-light-out state.

A voltage is applied to the base of transistor 314 to turn the transistor on through one of two sources. First, the light source can be manually placed in the standby mode by the closing of control switch 201. This pulls the voltage presented to the input of invertor 318 low so as to cause the invertor to assert a high voltage, a transistor on voltage, to transistor 314 through OR gate 320. Normally, when switch 201 is open, a high voltage is presented to the input of invertor 318 through a resistor 321.

Alternatively, a transistor-on voltage is applied to transistor 314 from a scope-sensing circuit 322. Scope-sensing circuit 322 monitors signals representative of whether or not a cable is plugged into the light source 122, the type of cable and, if it is a scope-sensing cable, whether or not an endoscope 22 is attached thereto. Depending on the signals received by the scope-sensing circuit 322, the scope-sensing circuit asserts a SCOPE-SENSED signal to standby control circuit 312. If the SCOPE-SENSED signal is not asserted, transistor 314 is turned on to hold the light source 122 in the standby mode. If the SCOPE-SENSED signal is received, standby control circuit 312 is placed in what is referred to as a "toggle" mode. When the standby control circuit 312 is in the toggle mode, the standby control circuit can then be used to put the light source 122 in and take the light source out of the standby mode by the manual setting of control switch 201.

Scope-sensing circuit 322 includes a comparator 324 that produces a signal indicative of whether or not a cable is clamped to the light source 122. Comparator 324 has a noninverting input that is tied to a +12 VDC voltage source through a pull-up resistor 326. The noninverting input of comparator 324 is also tied to one terminal of microswitch 213. The opposed end of microswitch 213 is tied to ground. The inverting input of comparator 324 is applied to the junction of two series connected resistors 328 and 330 that are tied between the +12 VDC voltage source and ground. Resistors 328 and 330 are selected so as to cause a signal between 1.0 and 11.0 VDC to be applied to the inverting input of comparator 324.

The output of comparator 324 is tied to a +5 VDC voltage source through a resistor 332. The output signal produced by comparator 324 is applied to an invertor 334. The output of invertor 334 is applied to one input of an AND gate 336.

Also integral with scope-sensing circuit 322 are the conductive jaws 206 of clamp assembly 204 and the conductive contact ring 228 of socket 202. (The jaws 226 and contact ring 228 being represented as terminals in FIG. 22A). Wire 215 (FIG. 17) tied to the jaw 206 is connected to ground. Contact ring 228 is tied to the +5 VDC voltage source through a resistor 340. The voltage present at contact ring 228 is thus a function of the type of cable connected to the light source 122 and, if it is a scope-sensing cable 124, whether or not the cable is attached to an endoscope 22.

The voltage present at contact ring 228 is applied to the noninverting inputs of three separate comparators 342, 344, and 346. The inverting input of comparator 342 is tied to the junction of resistors 348 and 350 that form a voltage divider between the +5 VDC voltage source and ground. Resistors 348 and 350 are selected to present a voltage between 3.0 and 4.0 VDC to the inverting input of comparator 342. The +5 VDC voltage source is connected to the output of comparator 342 through a resistor 351. The output signal from comparator 342 is applied to the second input of AND gate 336.

The output signal from comparator 342 is also applied to the input of an invertor 352. The signal produced by invertor 352 is applied to one input of an AND gate 357.

The inverting input of comparator 344 is tied to the junction of two series connected resistors 354 and 356. Resistors 354 and 356 are connected between the +5 VDC voltage source and ground and have the same resistance so as to present a 2.5 VDC signal to the inverting input of comparator 344. The +5 VDC voltage source is tied to the output of comparator 344 through resistor 358. The output signal from comparator 344 is applied to the input of an invertor 360. The signal produced by invertor 360 is applied to one of the inputs of an AND gate 362.

The inverting input of comparator 346 is connected to the junction of two series connected resistors 364 and 368. Resistors 364 and 368 extend between the +5 VDC source and ground and are selected so that the voltage present at the junction thereof is between approximately 1.0 and 1.5 VDC. The +5 VDC voltage source is tied to the output of comparator 346 through a resistor 370. The output signal produced by comparator 346 is applied to the second input of AND gate 362.

The output signal produced by AND gate 362 is applied to the second input of AND gate 357. The output signals produced by AND gates 336 and 357 are applied to the inputs of an OR gate 364. The signal produced by OR gate 364 is the SCOPE-SENSED signal produced by scope-sensing circuit 322. The signal produced by OR gate 364 is applied to standby control circuit 312. More particularly, in the illustrated version of the invention, the signals produced by OR gate 364 is applied to an invertor 366 integral with standby control circuit 312. The output signal from invertor 366 is the second input signal into OR gate 320.

When the light source 122 is actuated and there is no cable attached thereto, microswitch 213 is open and a 5.0 VDC signal is present at the contact ring 228. Owing to the state of microswitch 213, comparator 324 presents a +5 VDC high signal to invertor 334. Invertor 334 thus produces a low signal to its complementary input into AND gate 336. The AND gate 336 thus asserts a low signal to one of the inputs of OR gate 364.

Owing to the presence of the +5 VDC signal at contact ring 228, comparator 342 likewise asserts a high signal. This high signal is inverted by invertor 352. The low signal produced by invertor 352 causes AND gate 357 to likewise produce a low signal. Thus, two low signals are provided to OR gate 364. The OR gate 364 thus asserts a low signal which is interpreted by standby control circuit 312 as a SCOPE-SENSED signal, an instruction to place the light source in the standby mode. In the depicted version of the invention, this signal is inverted by invertor 366. The resultant high signal is thus applied through OR gate 320 to the base of transistor 314 to turn the transistor on.

Figure 17:
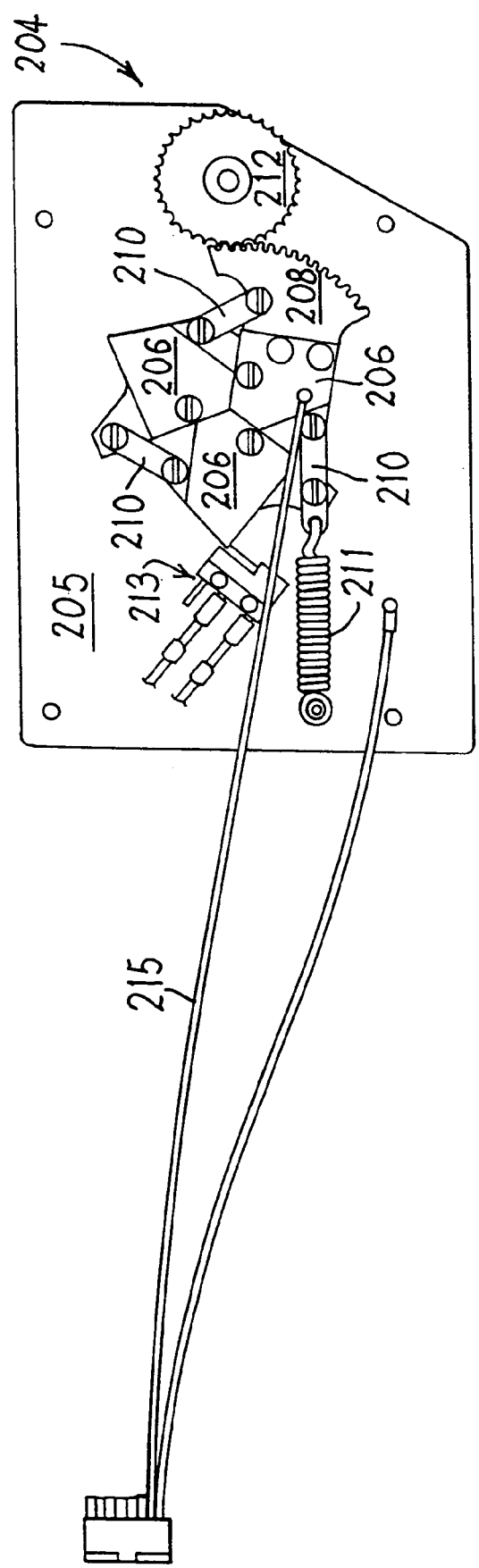
FIG. 17 depicts the clamping mechanism integral with the light source used to secure the cable thereto.

When a light cable, regardless of its scope-sensing capabilities, is secured in socket 202, microswitch 213 is closed by the outward movement of the adjacent jaw 206 (FIG. 17). The closing of microswitch 213 causes the voltage presented to the noninverting input of comparator 324 falls to zero and the output of the comparator likewise goes low. Owing to the inversion of the signal produced by comparator 324 by invertor 334, a high signal is thus presented to one input of AND gate 336.

If a conventional cable is attached to the light source 122, the cap integral with the light end plug will be spaced a slight distance inwardly from the contact ring 228. Thus, the circuit between conductive jaws 206 and contact ring 228 remains open. Consequently, the signals produced by comparators 342, 344 and 346 are the same as they were in the no-cable state. Therefore, comparator 342 produces a high signal that is presented to the second input of AND gate 336. Since both inputs to AND gate 336 are high, the AND gate produces a high signal to OR gate 364. The OR gate 364 thus asserts a high, SCOPE-SENSED signal to standby control circuit 312.

Invertor 366 inverts the SCOPE-SENSED signal and applies it to OR gate 320. Thus, the standby control circuit 312 does not automatically place the light source in the standby mode. Switch 201 can, however, be actuated to manually place the light source in and remove the light source from the standby mode.

If a scope-sensing cable 124 is coupled to the light source 122, a first electrical connection is established between jaw 206 and light input tip 138 as seen by reference to FIG. 23. Simultaneously, a second electrical connection is established between cap 145 and contact ring 228. Thus, the electrical circuit between jaw 206 and contact ring 228 is closed. Assuming the cable 124 is not attached to an endoscope 22, only resistor 164 is placed in this circuit. Consequently, the voltage present at contact ring 228 drops to approximately 2.8 VDC.

When the above no-scope voltage is presented to comparator 342, the output signal of the comparator transitions low. The low signal produced by comparator 342 causes the output signal produced by AND gate 336 to likewise transition low. The low signal produced by AND gate 336 is applied to one input of OR gate 364. When the contact ring 228 voltage is in this no-scope voltage state, comparator 344 will continue to assert a high state signal. This signal is inverted low by invertor 360. The low signal produced by invertor 360 is applied to one input of AND gate 362 so as to place the output signal from AND gate 362 in the low state.

The low state of AND gate 362 causes a like transition of AND gate 357. Consequently, two low signals are applied to OR gate 364. The OR gate 364 thus asserts a low SCOPE-SENSED signal to standby control circuit 312. The receipt of the SCOPE-SENSED signal, as discussed, turns on transistor 314 so as to force the light source 122 into the standby mode.

If the scope-sensing cable 124 is connected to an endoscope 22 to which an adapter 126 is attached, the cable contacts 188 abut adapter contact ring 266. Thus, contact ring 266 completes the connection between conductors 62 so as to place resistor 166 in parallel with resistor 164. The insertion of resistor 166 into the circuit thus serves to cause the voltage present at light source contact ring 228 to fall to approximately 2.0 VDC.

When the contact ring 228 voltage drops to 2.0 VDC, the scope-connected voltage, comparator 342 will continue to assert a low output signal. It will be observed, however, that the output signal from comparator 342 is inverted by invertor 352 and the resultant high signal is applied to one of the inputs of AND gate 357.

The drop of contact ring 228 voltage to the scope-connected level does however cause the output signal from comparator 344 to transition low. This low output signal is inverted by invertor 360 and applied as a high signal to one input of AND gate 362. The second input of AND gate 362 is, in this state, receiving a high signal from comparator 346. Consequently, AND gate 362 asserts a high signal to the second input of AND gate 357.

Since, in the scope-connected state, AND gate 357 receives as inputs two high signals, the AND gate asserts a high signal. This high signal is applied through OR gate 364 to the standby control circuit as the SCOPE-SENSED signal. The receipt of the SCOPE-SENSED signal cause the standby control circuit to turn off transistor 314 so that system monitor circuit 295 provides the signals employed for controlling the intensity of the light emitted by light source 122. Light source 132 can still manually be placed in the standby mode by the closing of switch 201.

An advantage of endoscope system 120 is that light source 122 can be used with both the scope-sensing cable 124 and with conventional cables. When a conventional cable is plugged into the light source 122, the light source operates in a conventional manner and can be placed in the standby mode by depression of control button 201. When the scope-sensing cable 124 is employed, intensity control circuit 197 will automatically place the light source in the standby mode whenever the cable is not connected to the scope adapter 126.

It should be recognized that the foregoing description is directed to one specific embodiment of the invention and that other versions of the invention may vary from what has been described. Other versions of the invention may employ cable plugs, light source sockets and endoscope cable adapters different from what has been described. For example, in some versions of the invention, the conductive contacts on the cable plugs and complementary sockets/adapters may not be longitudinally spaced apart from each other as has been described. In these versions of the invention, these contacts may be located at different radial locations around a common circumference.

Figure 24:
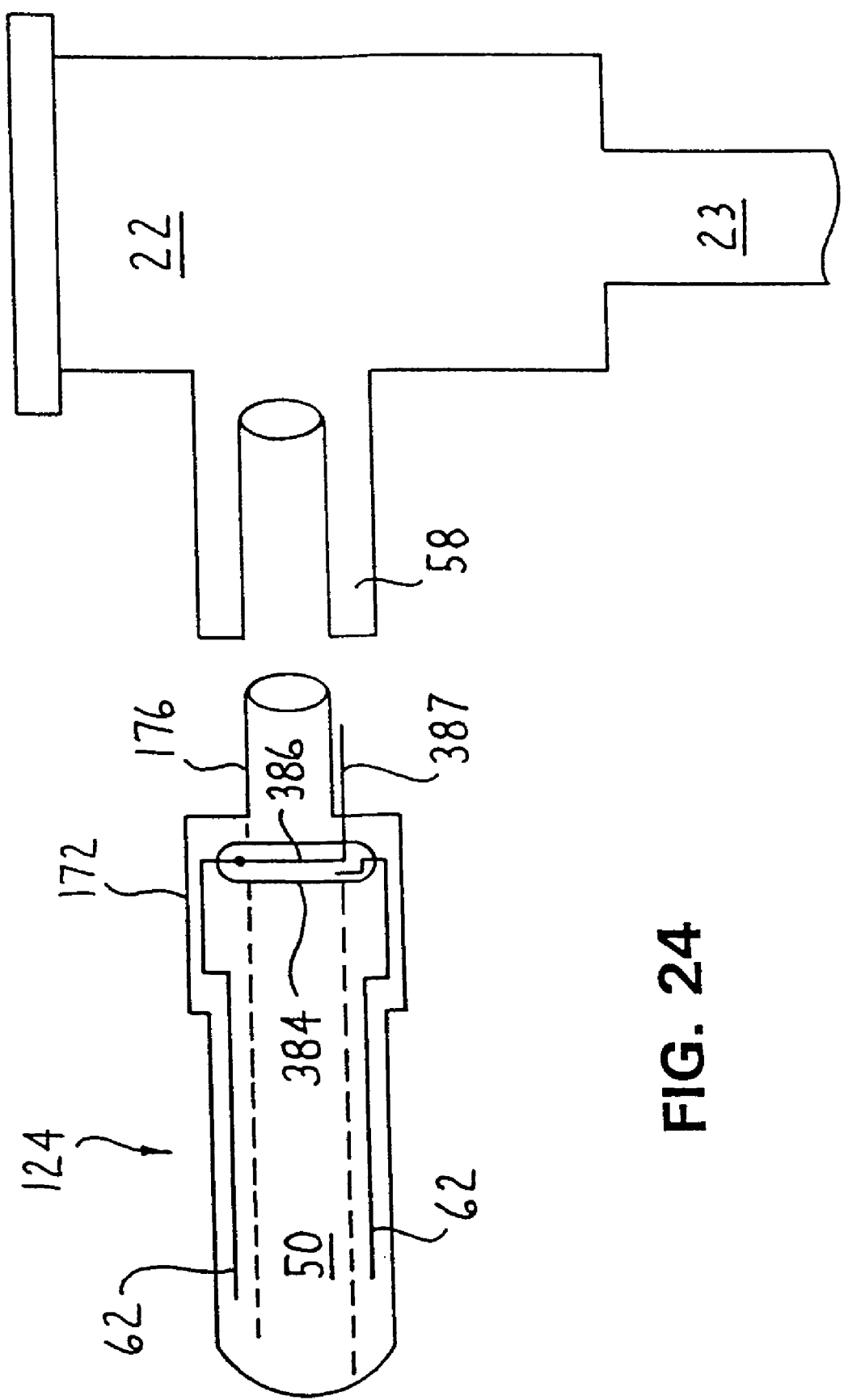
FIG. 24 is a diagrammatic illustration of a fiber optic scope-sensing cable of this invention with a scope-sensing switch located in the scope end plug.

Still other versions of the invention may not have the exposed contacts of the described embodiment. In some versions of the invention, as seen in FIG. 24, a small switch 384 may be located in the scope end plug 172 of the fiber optic cable 124. This switch 384 is provided with a contact 386 that only closes the connection across conductors 62 when a complementary moving member 387 is displaced upon the coupling of the cable 124 to the endoscope 22.

An advantage of this embodiment of the invention is that is that it eliminates the need to base the closing of the circuit established by the conductors 62 based on contacts integral with the scope end tip staying in physical contact with a third conductive element.

Figure 25:
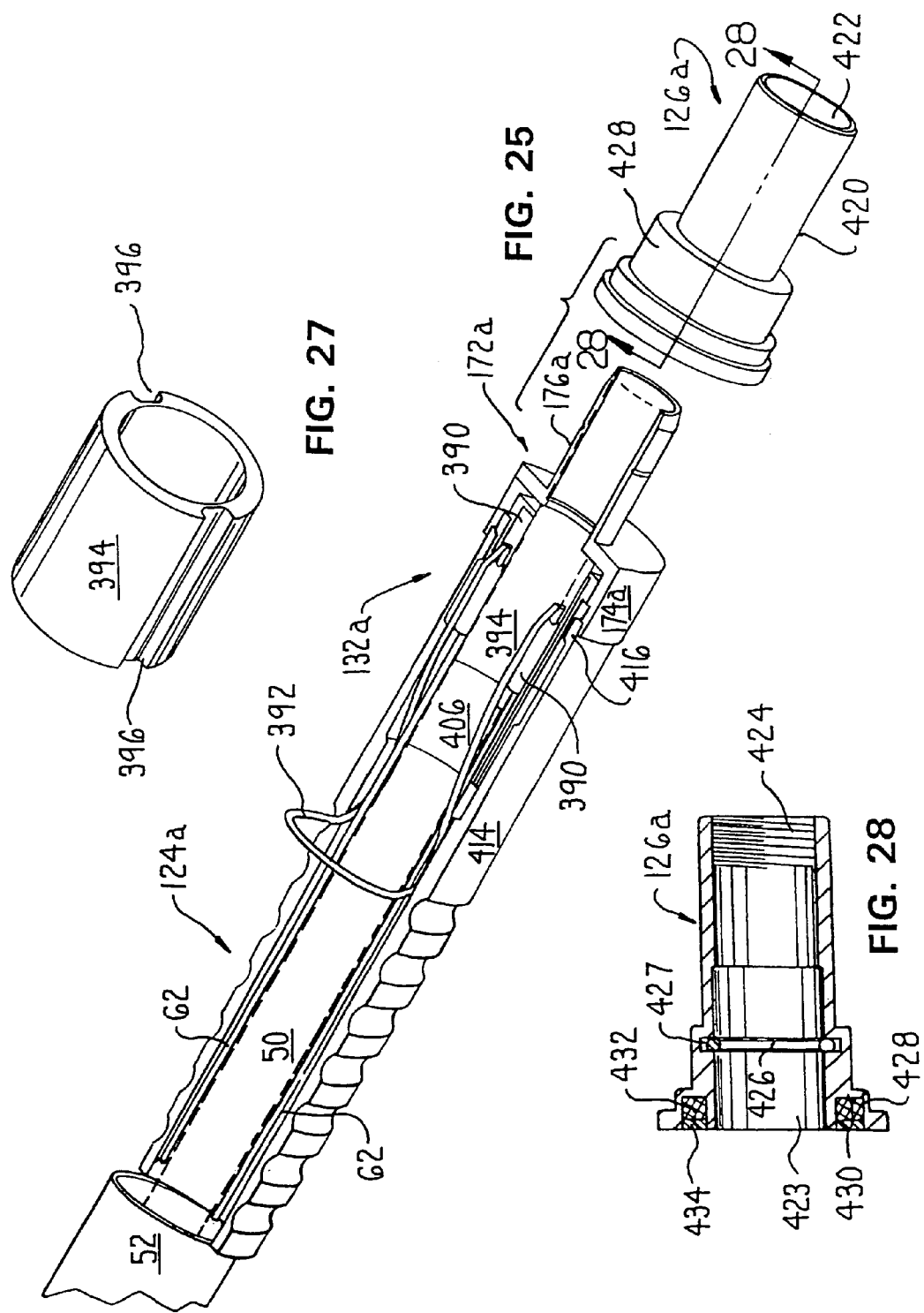
FIG. 25 is a cutaway and exploded view of a fiber optic scope-sensing cable of this invention with magnetically actuated scope-sensing switches in the scope end plug and the complementary adapter with which this cable is employed.
Figure 26:
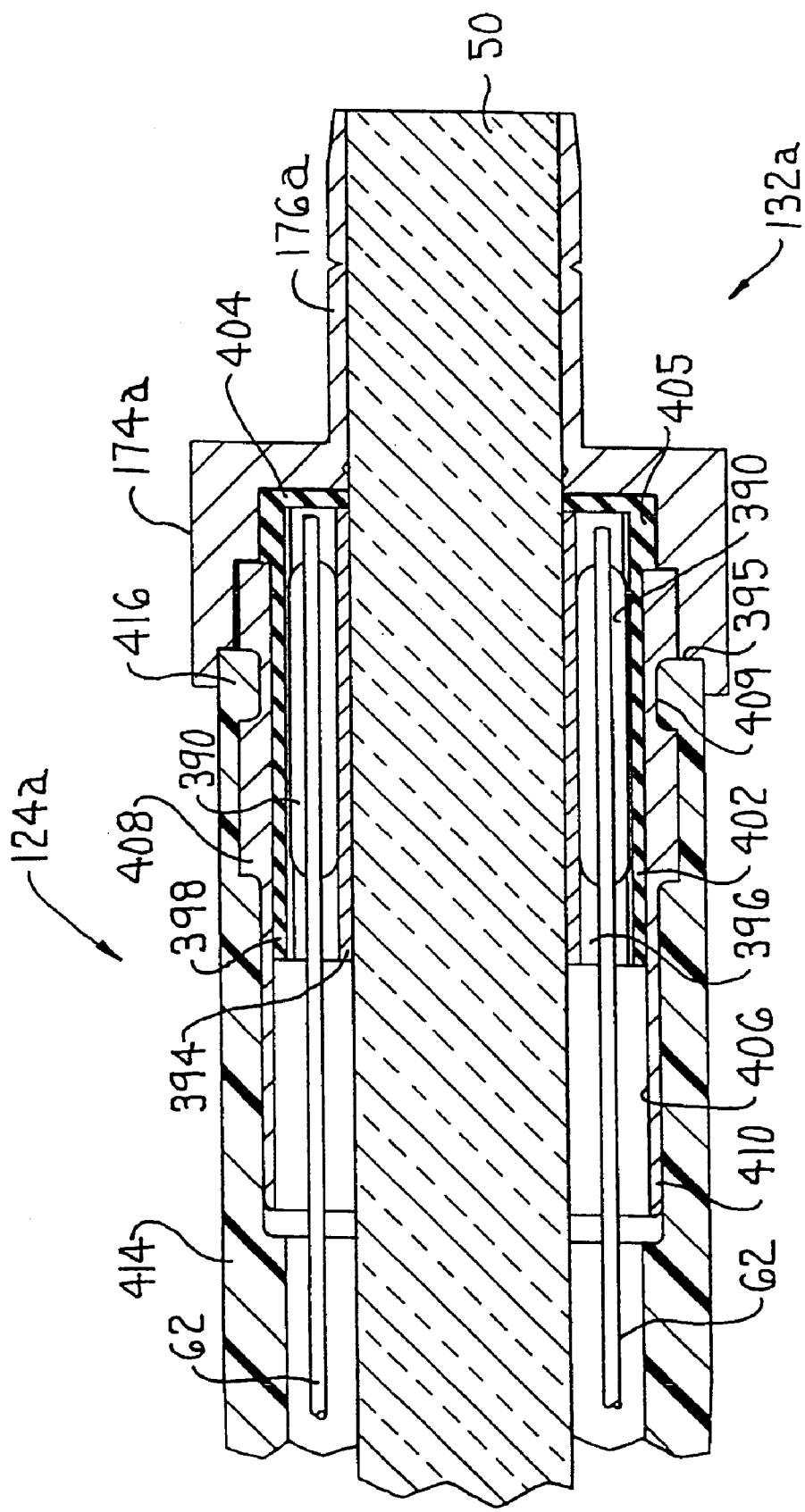
FIG. 26 is a perspective view of the insulator of the cable of FIG. 25.

Alternatively, as depicted in FIGS. 25 and 26, the scope end of the fiber optic cable may be provided with one or more magnetically actuated switches that are set by a magnet integral with the complementary adaptor. These Figures depict an alternative cable 124a of this invention. Cable 124a includes the fiber optic core 50, the electrical conductors 62, the light end plug 130, and the resistors 164 and 166 of previously described cable 124 (FIGS. 12 and 13). Cable 124a also includes a scope-end plug 132a in which two magnetically actuated reed switches 390 are seated. The reed switches 390 are series connected together by a harness 392 formed of wire that extends around the fiber optic core 50. The free end of each reed switch 390, the end not connected to the harness 392, is connected to an end of one of the conductors 62. The reed switches 390, when closed, close the circuit between conductors 62.

More particularly, scope end plug 132a has a scope end tip 172a with a solid, wide diameter base section 174a. Base section 174a is shaped to have step 395 around the inner wall that defines the open end of the base section. A narrow diameter stem section 176a extends outwardly from base section 174a. Fiber optic core 50 extends to the end of stem section 176a. A sleeve-shaped insulator 394 is fitted over the section of the fiber optic core 50 seated in the scope end tip base section 174a. Insulator 394 is formed out of ULTEM plastic or other sterilizable plastic. The insulator 394 is compression fit over the section of the core 50 it surrounds. As seen in FIG. 27, the outer wall of insulator 394 is formed to define two opposed grooves 396 that extend the length of the insulator. Each reed switch 390 is seated in a separate one of the grooves 396. A silicon adhesive, not illustrated, holds the reed switches 390 in the grooves 396.

A sleeve-like outer shell 398 surrounds the reed switches 390 and the insulator 394. Shell 398 is formed out of ULTEM plastic or other insulating plastic. Shell 398 has a cylindrical main body 402 that surrounds the insulator 394. The shell 398 is also formed with an annular, inwardly directed lip 404. Lip 404 has an inner edge against which the fiber optic core 50 abuts. It will further be observed that the end of main body 402 adjacent lip is formed to have step 405 with greater outer diameter than the rest of the body. When the scope end plug 132a is assembled, shell 398 is positioned so that the outer surface of lip 404 abuts the flat surface of scope end tip 172a that serves as the transition between base section 174a and stem section 176a. The outer surface of step 405 seats against the inner wall of base section 174a.

A generally tube-shaped insert 406 is seated over shell 398. Insert 406 is formed of aluminum or other light-weight metal. The insert 406 is shaped to have an inner wall with a constant diameter. The outside of the insert 406 is shaped to have first and second sections 408 and 410, respectively; the first section 408 has an outer diameter greater than the outer diameter of second section 410. It will further be observed that the first section 408 of the insert 406 is formed to define an annular groove 409. Insert 406 is tightly fitted over shell 398 and the components that shell 398 surrounds. When the scope end plug 132 is so assembled, the insert first section 408 is seated in the scope end tip base section 174. In the illustrated version of the invention, insert 406 has a length greater than that of insulator 394 and of outer shell 398. Accordingly, insert 406 extends a further distance towards the light end plug 130 that either insulator 394 or outer shell 398.

A flexible handle 414 extends from scope end tip base section 174a over insert 406. Handle 414 is formed from silicon rubber. The distal end of handle is formed with an inwardly directed lip 416. Lip 416 is seated in insert groove 409. The distal end of the handle 414 itself is seated in the space defined by the step 395 of scope end tip 172a.

An adapter 126a with which cable 124a is used is now described by reference to FIGS. 25 and 28. Adapter 126a includes a tube-like body 420 formed out of metal. The body is shaped to have an axially extending through bore 422 that serves as the space in which the endoscope light post 58 and scope end tip stem section 176a seat. In the depicted version of the invention the inner wall of the body 420 defining bore 422 is formed with threading 424 adjacent the distal end of the adapter 126a. The threading 424 engages complementary threading formed around the light post 58 to hold the adapter to the endoscope 22, (light post threading not illustrated).

The proximal end of the body 422 is formed with a counterbore 423 that is coaxial with and slightly larger in diameter than bore 422. Counterbore 423 is dimensioned to receive scope end tip stem section 176a. A snap ring 426 is seated in a groove 427 formed in the inner wall of the body 422 that defines counterbore 423. Snap ring 426 engages complementary groove 184 on the scope end tip stem section 176a to hold the cable 124a to the adapter 126a.

The adapter body 422 is further formed to have a base section 428 with a relatively wide outer diameter adjacent the proximal end of the adapter 126a. Base section 428 is formed with an annular channel 430 that is open to the proximal end of the adapter 126a that is separated from and surrounds counterbore 423. An annular magnet 432 is seated in the base of channel 430. A ring 434 formed of epoxy or other adhesive material holds the magnet 432 in channel 430.

When cable 124a and adapter 126b are employed with endoscope 22 and light source 122, they are used in the manner with which the previously described cable 124 and adapter 126 are used. When the cable 124a is coupled to adapter 126, the magnetic field surrounding magnet 432 causes the contacts internal to reed switches 390 to close. The closing of reed switches 390 closes the connection between conductors 62 to tie resistor 166 in parallel across 164. The change of resistance of this circuit is measured by scope sensing circuit 322 as previously described.

An advantage of the fiber optic cable 124 and adapter 126a is that the moving components of reed switches 390 are contained totally within the scope end plug 132a. Thus these components are not exposed to the surgical and sterilization fluids and material which might possible cause their degradation.

Also, in the above described version of the invention two, series-connected reed switches 390 are provided. An advantage of providing two switches is that if one inadvertently closes, the other should remain open. This feature substantially eliminates the likelihood cable 124a will provide a false indication that it is connected to an endoscope 22 when no such connection has been established.

Moreover, it should be recognized that the intensity control circuit 197 may be provided with override switches that allow surgical personnel to regulate the emission of light independently of the connected/disconnected state of the associated fiber optic, scope-sensing light cable. It should similarly be recognized that the mechanism for controlling the intensity of the light emitted by the light source may also vary from what has been described. For example, other versions of the invention may not employ the shutter with variable aperture. In these versions of the invention, the intensity control circuit may regulate the energization voltage or current applied to the light emitting bulb in order to regulate the amount of light emitted by the bulb itself. Also, the intensity controller could be configured to turn the bulb or other light emitting element off if the cable is disconnected from the complementary endoscope.

Also, while the disclosed circuit 197 is shown as comprising a set of discrete components, that need not always be the case. In some versions of the invention, the intensity control circuit may include a microprocessor, specifically programmed to respond to conventional cable/scope-sensing cable and scope connected/scope disconnect signal states by placing the light source in and out of the standby mode. In these, as well as in other versions of the invention, the circuitry internal to the scope-sensing cable may be different from what has been described. For example, it may be desirable to remove the resistors and substitute therefor logic components capable of withstand the sterilization environment to which the cable is exposed.

Furthermore, in some versions of the invention, it may be desirable to provide two pairs of conductors in the fiber optical cable. A first one of the pairs may be connected to the adapter 126 as described. The second pair of conductors would actually be a single conductor that is connected to two additional contacts integral with the proximal-end plug. The scope-sensing circuit could then monitor whether or not complementary conductors associated with the light source socket form either and open or closed circuit. Based on the state of this circuit, the scope-sensing circuit internal to the light source could evaluate the conventional cable/scope-sensing cable and scope connected/disconnected states of the system 120. This circuit would eliminate the need to provide the scope-sensing cable with resistors or other discrete components.

It should further be recognized that the contact ring 266 may be integrally installed on the light post 58 of the endoscope 22.

Figure 29:
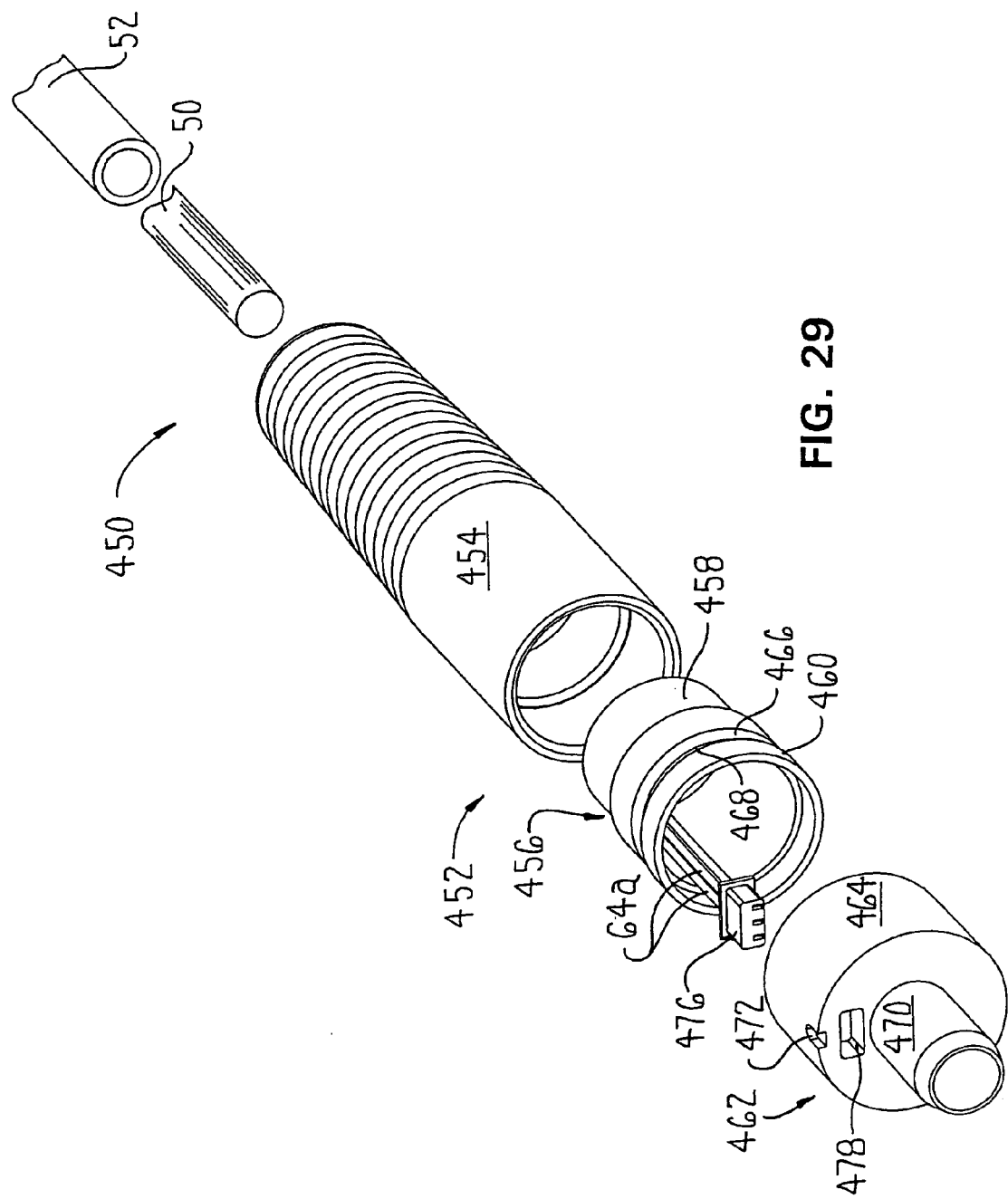
FIG. 29 is an exploded view of the proximal end tip, the light end tip, of an alternative fiber optic cable of this invention.

FIG. 29 depicts the proximal end of an alternative fiber optic cable 450 of this invention. Cable 450, in addition to core 50 and insulator tubing 52, includes three conductors 64*a*. In FIG. 29, proximal ends of the conductors 64*a* are shown. Conductors 64*a* it should be understand are each insulated. Cable 450 includes a light end plug 452. Plug 452 has a tube-like rubber handle 454. The proximal ends of the fiber optic core 50, insulated tubing 52 and conductors 64*a* extend into and through the open distal end of handle 454.

A multi-section, sleeve-shaped insert 456 fits into the open proximal end of handle 454. The insert 456 is formed from a rigid plastic. Insert 456 is shaped to have first section 458 dimensioned to be press-fit secured in the open proximal end of handle 454. Extending forward, proximally, from the first section 458, insert 456 has a second section 460. Insert second section 460 has a larger outer diameter than first section 458.

A cap 462 formed out of stainless steel is fitted over insert second section 460. The cap 462 has a relatively wide diameter main body 464 that is press fit over the insert second section 460. In order to prevent fluid leakage into the cable 450, an O-ring 466 is located between the outer surface of insert second section 460 and the inner wall of cap body 464. The O-ring 466 seats in a groove 468 formed in the insert second section 460. Cap 462 has an elongated, cylindrical, hollow head 470 that extends forward from the front face of main body 464. The proximal end of core 50 is fitted in head 470. Head 470 is the portion of cable 450 that is seated in the socket of the complementary light source with which the cable is used.

Cap 462 is further formed so as to define a small alignment notch 472 in the outer perimeter of the main body 464. The alignment notch 472 facilitates the proper positioning of plug 452 for a purpose to be explained below.

Light end plug 452 is provided with a connector 476. The connector 476 is seated in an opening 478 formed in the face of the cap main body 464. The front face of connector 476 is flush with the adjacent face of the main body 464. The proximal end of each conductor 64*a* is connected to a complementary terminal internal to the connector 476. When the light end plug 452 is fitted to the complementary light source socket, the seating of an alignment pin integral with the socket in notch 472 causes the plug to be positioned so that connector 476 mates with a multi-pin electrical plug 477 (FIG. 34) integral with the socket. The mating of these two components causes an electrical connection to be established between the circuitry internal to the light source and conductors 64*a*.

Figure 30:
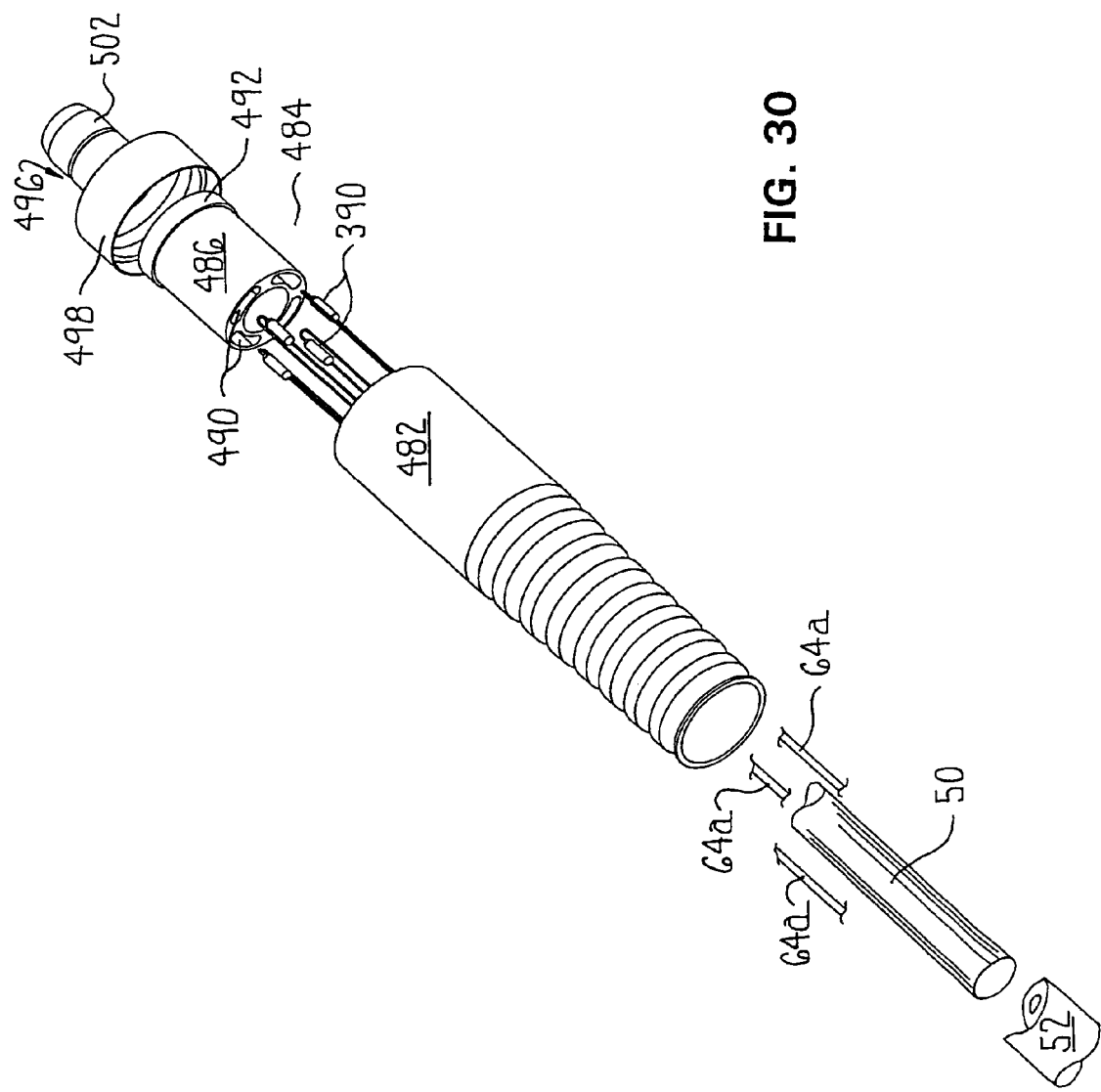
FIG. 30 is an exploded view of the distal end tip, the scope end tip of the cable of FIG. 29.
Figure 31:
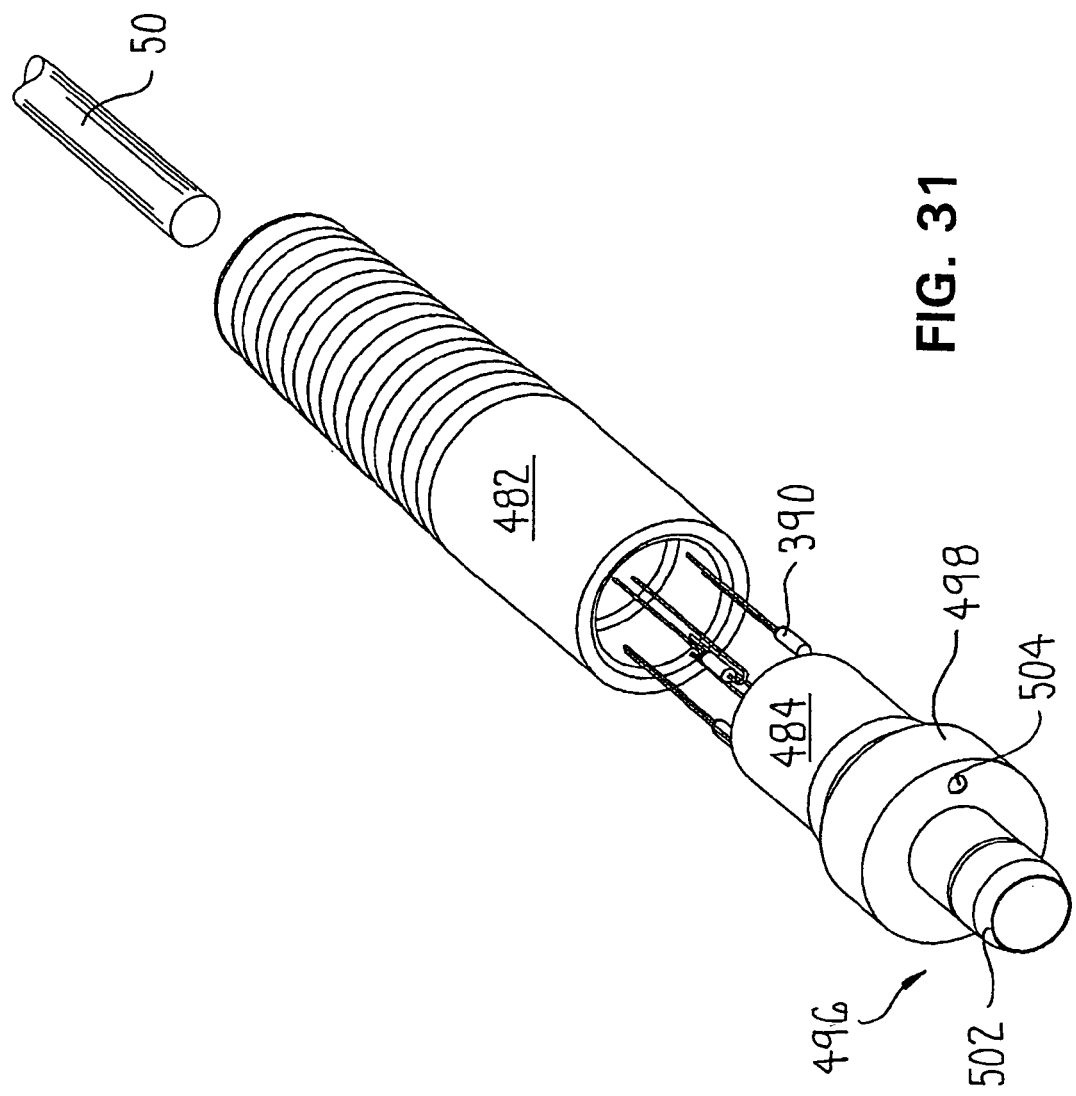
FIG. 31 depicts the end face of the tip pf FIG. 30.

A scope end plug 480 of cable 450 is illustrated in FIGS. 30 and 31. Plug 480 includes a rubber handle 482 similar in material and shape to handle 454. The distal end of core 50, insulating tube 52 and conductors 64*a* extend into handle 454. A generally cylindrical insulator shell 484 is seated in the open distal end of handle 454. Shell 484, which is formed of plastic has a relatively thick wall 486 with a circular cross sectional profile. The inner surface of wall 486 defines a bore 488 that extends axially through the shell 484. The distal end of core 50 extends through bore 488. Wall 486 is further formed to define four separate chambers 490 each of which is located between the inner and outer surfaces of the wall. Each chamber 490 opens from the proximal end of wall 486. Shell 484 is formed so that the opposed, distal ends of chambers 490 are closed. The shell 484 is further shaped to have a small annular lip 492 that extends outwardly from the distal end of the outer surface of wall 486. When the shell 484 is seated in handle 482, lip 492 extends around the outer open end of the handle.

A scope end tip 496 is fitted over the exposed end of shell 484. Tip 496 is formed from stainless steel and shaped to have a wide diameter base 498. Base 498 has an open proximal end in which the exposed end of shell 484 is press fit and sealingly secured. Extending forward from base 498, tip 496 has a narrow diameter head 502. The distal end of core 50 seats in head 502. Tip 496 is further formed so that the scope-facing face of the base 498 is formed to have an opening 504. Opening 504 is contiguous with a closed-end bore formed in the distal end face of shell 484 (bore not identified).

Plug 480 further includes four, magnetically set reed switches 390. Each reed switch 390 is seated in a separate one of the chambers 490 formed in the shell 484. As described below, the reed switches 390 are connected across conductors 64*a*.

Figure 32:
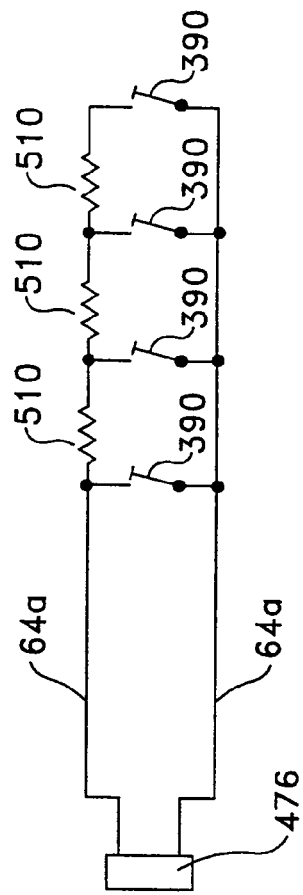
FIG. 32 is a schematic and block diagram of the circuit internal to the cable of FIG. 29.

FIG. 32 depicts one circuit internal to cable 450. In this circuit, three resistors 510 are series connected to the end of one of the conductors 64*a*. The reed switch 390 extends from the resistors 510 to the second conductor 64*a*. More particularly, one reed switch 390 extends from the junction of the first, proximal, resistor 510 with the conductor 64*a* to which the resistors are connected. A second reed switch 390 extends from the junction of the first resistor 510 with the second, middle, resistor 510. A third reed switch 390 extends from a junction of the second resistor 510 to the third, distal resistor 510. The fourth reed switch 390 extends from the distal, free end of the third resistor towards the second conductor 64*a*. (This version of the cable 450 does not include the third conductor illustrated in FIGS. 29 and 30.)

Figure 33:
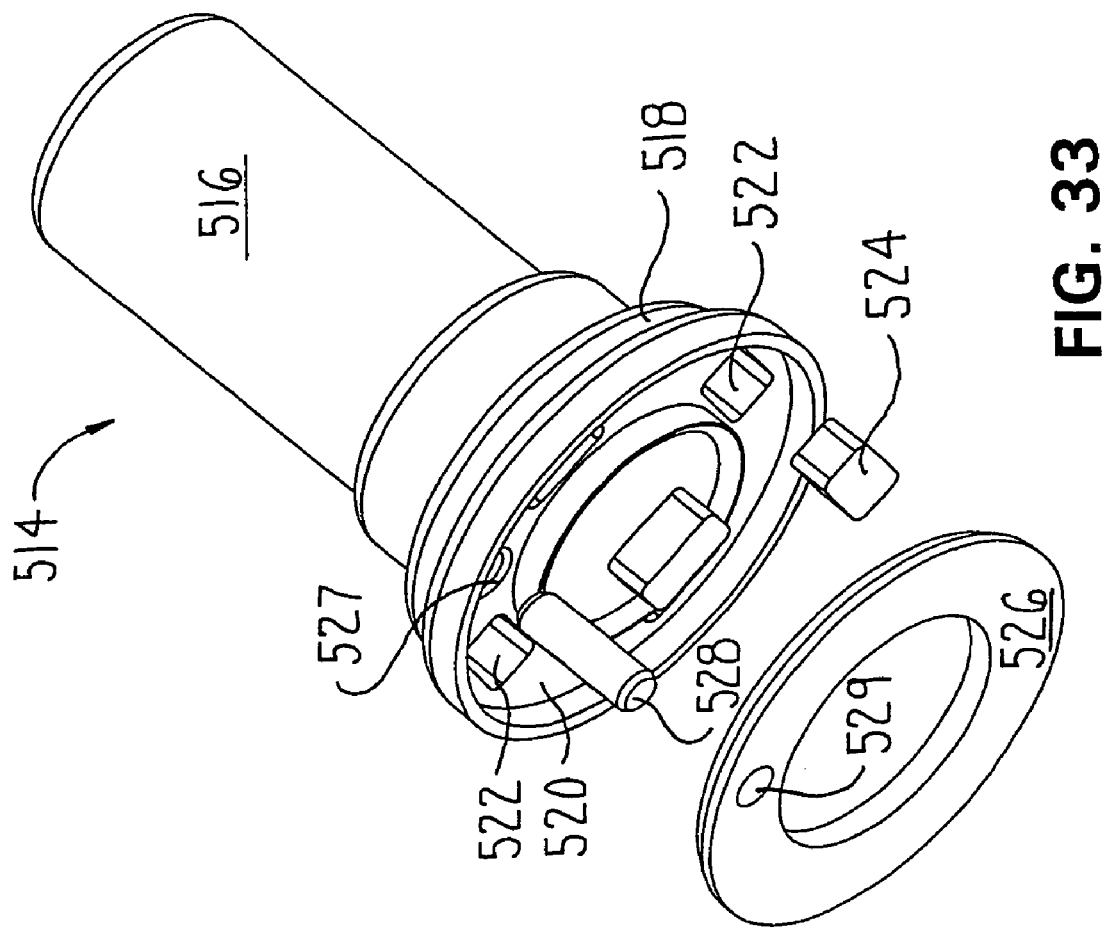
FIG. 33 is an exploded view of an adaptor intended for use with the cable of FIG. 29.

FIG. 33 depicts an adaptor 514 intended for use with an endoscope 22 and fiber optic cable 450. Adaptor 514 includes a tube like body 516 formed out of a relatively low magnetic metal such as stainless steel. Body 516, like adaptor body 420 (FIG. 28), is formed to having threading 424 to facilitate the engagement of the adaptor to the endoscope 22. Also, the inside of the adaptor body 516 is provided with a snap ring 427 (FIG. 27) to facilitate the removable securing of the head 502 of scope end plug 480 to the adaptor.

Adaptor body 516 is formed so that the proximal end thereof has a base 518 with an outer diameter that is wider than the portion of the body that extends distally from the base. Body 516 is formed so as to have a proximal end face 520 at the proximal end of base 518. Face 520 is recessed inwardly relative to the outer perimeter of the base 518. The adaptor body 516 is further formed to define a number of rectangular holes 522 that extend inwardly from face 520. Holes 522 are spaced equangularly around the circumference of face 520.

A single magnet 524 is seated in separate ones of the holes 522. The specific hole 522 in which the magnet 522 is seated is a function of the type of endoscope 22 with which the adapter is intended to be used. Again, in some versions of the invention, the adapter may be permanently fitted to the light post of the endoscope 22. A washer-like adapter plug 526 formed of magnetically permeable plastic or metal is fitted over face 520 to cover the magnet 524.

Adapter 514 is further provided with an alignment pin 528. Pin 528 is securely fitted in a circular hole formed in body base 518 and extends proximally away from the adaptor 514. Pin 528 extends through a hole in plug 526. When the scope end plug 480 is fitted in the adaptor 514, pin 528 seats in opening 504 and bore 506. This alignment causes a specific one of the reed switches with a magnet 524.

More particularly, the position of the magnet 524 in the adapter 514 relative to the alignment pin is specific to the type of endoscope with which the adapter is used. In some versions of this invention, endoscopes 22 are type classified as a function of the outer diameter of their shafts 23.

Figure 34:
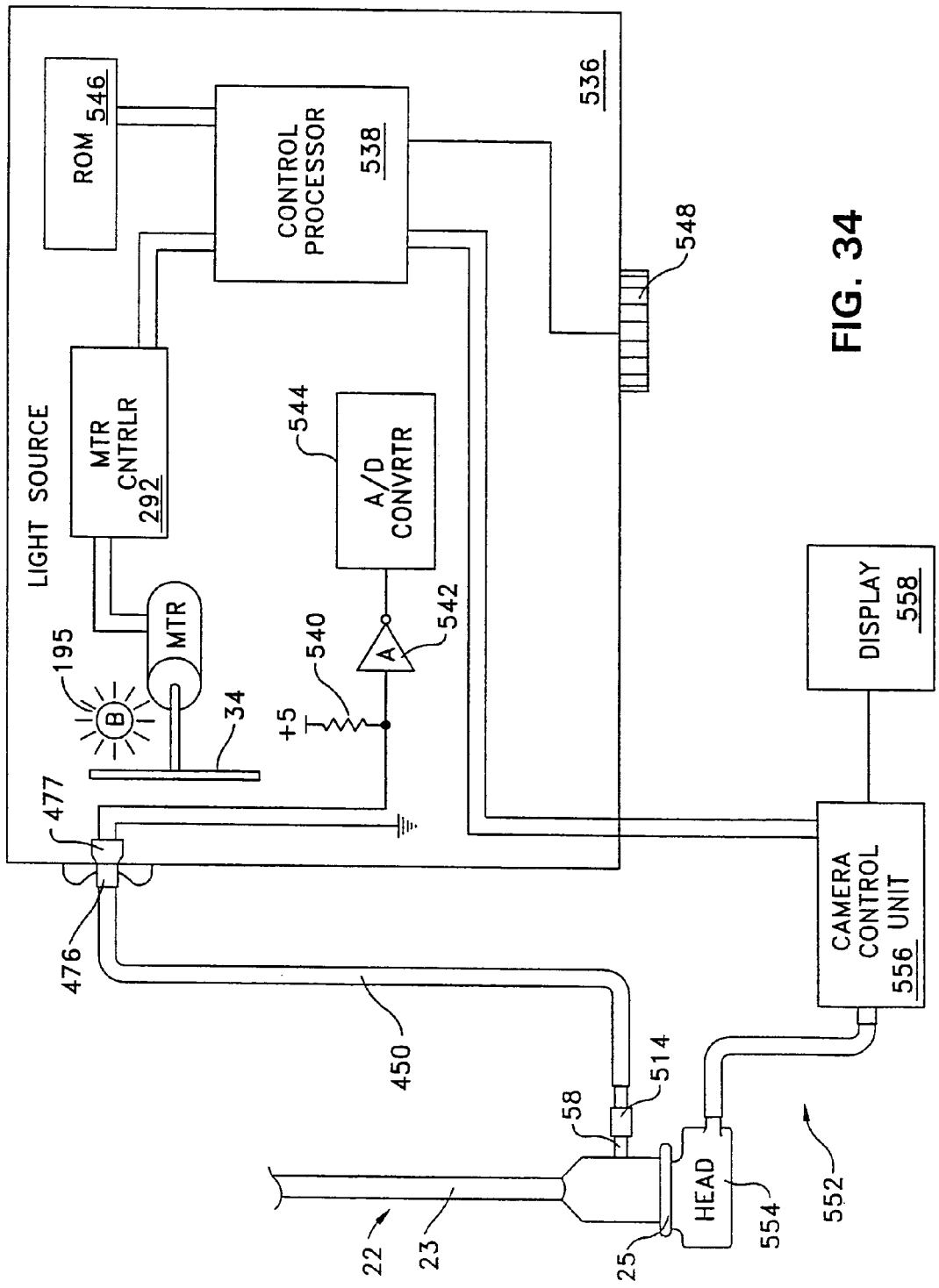
FIG. 34 is a block diagram of sub-circuits internal to the light source to which the cable of FIG. 29 is connected.

FIG. 34 depicts a light source 536 with which cable 450 and adaptor 514 are used. Light source 536 includes the previously described lamp 195, shutter 34, and stepper motor 37. Motor controller 292 is provided for regulating the actuation of motor 37. A control processor 538 generates the command signals that are applied to motor controller 292. Suitable processors for integration into light source 536 come from the 80C51 family of microcontrollers. Light source 536 also has a resistor 540 that is tied at one end to a 5 VDC voltage source internal to the light source, (source not shown). Resistor 540 is connected to the source plug 477 to which connector 476 is connected. More particularly, through this connection, resistor 540 is connected to cable resistors 510. A second connector of plug 477 is tied to ground. Specifically, this connection establishes a ground connection to the cable conductor 64a to which the reed switches 390 are connected.

The end of resistor 540 distal from the 5 VDC voltage source is also connected to the input terminal of a buffer 542. The output terminal of buffer 542 is connected to an analog-to-digital converter 544. The digital data stream generated by converter 544 is output to control processor 538. In FIG. 33, this data are being shown forwarded to processor 538 over a two-line bus 544.

Light source 536 is also shown as having a ROM 546 connected to control processor 538. ROM 546 stores the operating instructions executed by the control processor 538 to regulate the emission of light from source 536. The control processor 536 is also connected to manually-set controls represented in FIG. 34 by knob 548. The manually set controls are actuated in order for the medical person to control the light emitted by the source 536.

Figure 34A:
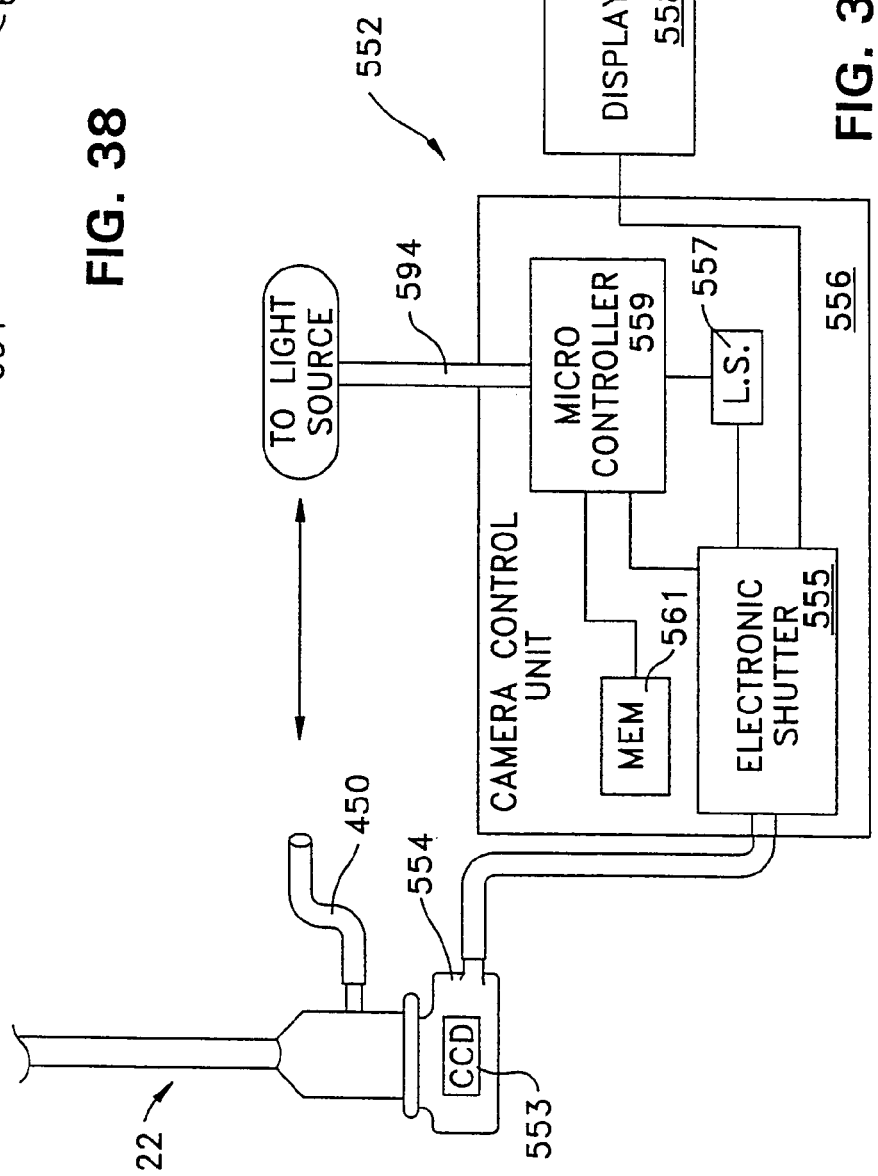
FIG. 34A is a block diagram of the sub-circuits of the camera of this invention.

The light source 536, in addition to being connected to the endoscope 22, is connected to a camera 552 that is employed to capture and display images of the surgical site to which the endoscope is directed. Cameral 552, as seen in FIG. 34A, has a head 554 that is mounted to the proximal, exposed end of endoscope 22. Head 554 contains a transducer, such as one or more charge coupled devices 553, that are employed to capture the emitted images and converts those images into an electrical signals. Each charge coupled device 553 includes large number of pixels. The pixels (not illustrated) store charge as a function of the quantity of light to which they are exposed.

Camera 552 also includes a camera control unit 556 that is connected to the head 552. Internal to unit 556 is an electronic shutter assembly 555. The electronic shutter assembly 555 gates, scans, the pixels integral with the charge coupled device 553 to determine the charge held by each pixel. Based on the quantity of this charge, the electronic shutter assembly 555 and other components internal to the camera control unit 556 generate signals representative of the image detected by the head 552. The image signals can be used to present an image of the surgical site on a display 558 and/or stored to generate a record of the images at the site.

The camera control unit also includes a light sensor circuit 557. In FIG. 34A, this circuit 557 is shown connected to receive an output signal from the electronic shutter assembly 555. The light sensor circuit 557, based on the signals received from the charge coupled device 553, generates a signal representative of the current light level at the surgical site.

Both the electronic shutter 555 and the light sensor circuit 557 are connected to a microcontroller 559 internal to the camera control unit 556. The light sensor signal supplies to the microcontroller 559 signals indicating the current light level at the surgical site. Based upon this input variable, and other input variables not relevant to this invention, microcontroller 559 regulates the actuation of the electronic shutter assembly 555. Specifically, microcontroller 559 regulates the frequency with which the electronic shutter assembly determines the charge present at the pixels integral with the charge coupled device 553. This regulation is referred to as controlling the "rate of electronic shutter" of the camera 552. This regulation is performed to ensure that the signals gated from the charge coupled device 553 can be used to generate a quality image of the surgical site. If signals representative of large quantities of pixel charge are generated, the resultant image signals may generate an image that is too bright, a whited-out image. If signals representative of too low a quantity pixel charge are generated, the resultant image signals may generate a viewable image that is excessively dark.

Microcontroller 559 also forwards to light source control processor 538 data representative of the current light level at the surgical site. One suitable camera 552 that can be employed with the light source of this invention is the 888™ Camera marketed by the Stryker Corporation of Kalamazoo, Mich.

Figure 35:
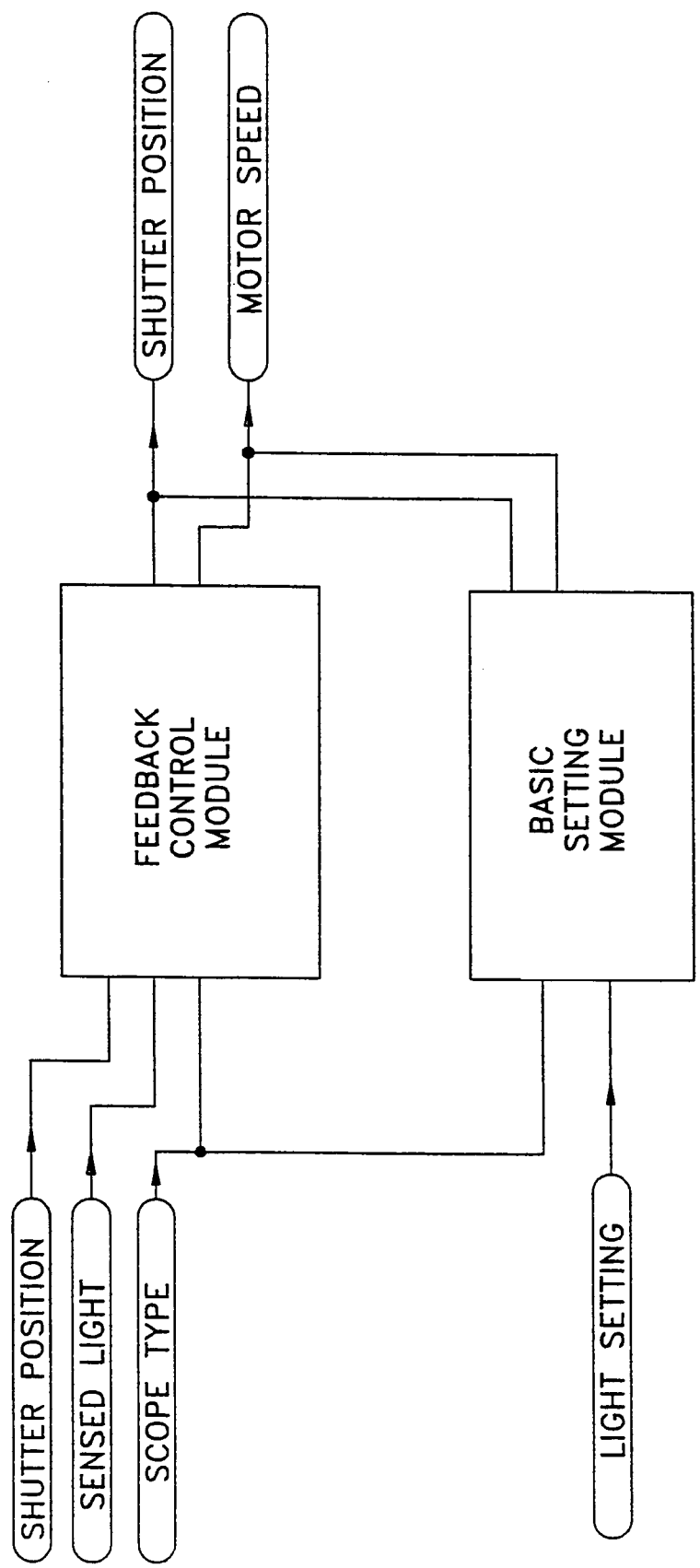
FIG. 35 depicts two modules of software instructions that are executed by the light source of this invention.

FIG. 35 depicts two of the software modules that are selectively executed by the light source control processor 538. A first module is the basic setting module 562. The basic setting module 562 provides an initial control of the quantity of light emitted by source 536. The input variables to module 562 are whether or not an endoscope is connected to the light source and the type of endoscope. In FIG. 35, these inputs are represented as a single "SCOPE TYPE" input. The second input into module 562 is the user-set light setting. This setting is determined by the control processor 538 based on the user-established actuation of knob 548. Based on the input variables into the basic setting module 562, the module generates commands to establish both the setting of the shutter position and the rate at which the shutter should be moved to its new position. This latter command is represented as the "MOTOR SPEED" output.

A second software module executed by control processor 538 is a feedback control module 564. Feedback control module 564 is primarily executed by the processor 538 in-between executions of basic control module 562. The feedback control module is executed by the processor 538 to adjust the light emitted by the source 536 so that the brightness of the reflected light at the surgical site remains constant once set by the surgeon. A first input into the feedback control module 564 is the current selected light output level. This is represented as the "SHUTTER POSITION" input. A second input into the feedback control module 564 are the sensed light measurements obtained from camera 552. As discussed hereinafter, a third input into feedback control module is an indication of the type of endoscope 22 connected to the light source 536. The output signals from feedback control module 564 are the previously described shutter position and motor speed signals.

The shutter position and motor speed signals generated by modules 562 and 564 are applied to a motor driver module (not identified) also executed by the control processor 538. Based on the above described input signals, the motor driver module sends signals to motor controller 292 that result in the motor 37 being actuated so that shutter 34 is appropriately repositioned. The signals generated by the motor driver also regulate the speed at which the motor 37 is actuated so as regulate the rate at which the shutter 34 moves. This speed regulation establishes the rate at which the light emitted by source 536 changes.

In order to use this version of the light system of this invention, cable 450 is plugged into light source 536. Initially, when the scope end plug 480 is not connected to a complementary adaptor, the cable reed switches 390 are spaced from any magnets. The reed switches 390 are thus in their normal, open state. Consequently, the voltage across conductors 64a is the open-circuit voltage of 5 volts. This voltage is applied through buffer 542 to converter 544. Converter 544 applies a digitized representation of this voltage to processor 538. Processor 538 interprets this signal as indicating that cable 450 is not attached to a complementary endoscope. Based on a recognition of this state being detected, basic setting module 562 is executed. More particularly, the basic setting module 562 generates shutter position instructions directing the shutter be positioned so that the light source is placed in the minimal light out position. Basic setting module 562 also generates motor speed instructions directing the motor 37 be run at relatively fast rate in order to place the shutter 34 in the desired position.

When cable scope end plug 480 is fitted into an endoscope adapter 514, the reed switches 390 are aligned with the holes 522 in the adaptor 518. The single reed switch 390 that is aligned with the magnet 524 fitted to adapter 514 transitions from the open state to the closed state. The closing of the reed switch 390 closes the connection between conductors 64a. As discussed above, the position of the magnet 524 in the adapter 514 is a function of type of endoscope 22. Therefore the particularly reed switch 390 that closes is likewise a function of endoscope type.

Depending upon which one of the reed switches 390 is closed, the signal flow is through none, one, two or three of the resistors 510. The level of the signal across the conductors 64a is thus function of which one of the reed switches 510 was closed. The level of this signal, which is a scope-sensed signal, is thus representative of the type of endoscope 22 to which the cable 450 is connected. This signal is digitized by converter 544. Converter 544 applies a digital form of this signal, a scope-type signal, to processor 538.

Processor 538, upon receipt of this new scope type signal, reexcutes the algorithm forming basic setting module 562. The basic setting module 562, in this reexecution, has an inputs the data representative of the type of endoscope to which the light source 536 is connected and the setting of knob 548. Based on this input data, basic control module 562 generates data indicating the new position at which the shutter 34 should be positioned. Module 562 also generates a signal indicating how fast motor 37 should be actuated to reposition the shutter 34. In this repositioning, the motor 37 is driven at a relatively fast rate. As a consequence of this repositioning of the shutter 37, light source 536 emits a quantity of light that is function of both the type of endoscope to which it is directed and the setting of the user-set knob 548.

Basic setting module 562 is further configured to set the shutter position as a function of the type of endoscope to which the source is configured. In the described version of the invention, module 562 is configured so that when it receives an indication that a relatively large diameter endoscope 22 is attached to the light source 536, the source should emit a relatively small quantity of light. When a relatively small diameter endoscope is attached to the light source 536, basic setting module 562 is configured to cause the source to emit a relatively large amount of light.

During the surgical procedure, medical personnel actuate knob 548 to adjust the amount of light emitted by source 536. Based on the resetting of knob 548, the basic setting module 562 generates a new shutter position signal so as to cause the resetting of shutter 34. Basic setting module 562 also generates motor speed signal so as to control the rate at which motor 37 resets shutter 34. In many preferred versions of the invention, to facilitate this readjustment of the shutter 34, module 562 causes the motor to run at a speeds at or slight below the speed at which the motor is driven to transition the light source from the no-scope to scope-connected light output states.

Also during the surgical procedure, movements of the surgical site and/or endoscope relative to each other may cause the light directed to surgical site to vary. The feedback control module 564 continually monitors signals from the camera 552 representative of the current light level at the surgical site. Based on this input variable, module 564 continually, selectively adjusts the position of the shutter 34 to ensure that the light present at the surgical site is uniform and matches the desired setting of knob 548.

The extent to which the shutter position is reset is also function of additional variables. One of these variables is the current shutter position, the current amount of light the source 536 should be emitting. A third input variable upon into the algorithm executed when the feedback control module 564 is executed is the type of scope of attached to the light source 536. Specifically, if the sensed light variable indicates that the quantity of light emitted by source 536 needs to be increased, less light needs to be supplied for a large diameter endoscope 22 than a small diameter endoscope. The algorithm internal to the feedback control module 564 is constructed to recognize this difference. Thus, the final generation of the shutter position output command signal by the feedback control module 564 reflects this difference between endoscopes 22.

Feedback control module 564 also generates a motor speed signal to regulate the rate at which motor 37 repositions shutter 34. Generally, the rate at which the shutter is reposition during feedback adjustment is slower than the rate at which it is adjusted when it is transitioned between the no-scope and scope-connected states. The motor speed is also a function of scope type. In some preferred embodiments of the invention, feedback control module 564 is configured so that, in comparison to smaller diameter endoscopes, for larger diameter endoscopes, the feedback adjustment occurs at a slower rate.

Thus, the above version of the invention does more than simply inhibit the emission of light when cable 450 is not attached to an endoscope. In this version of the invention, when cable 450 is attached to an endoscope 22, the control circuit internal to the light source initially resets the source so that it emits the appropriate amount of light for the specific type of endoscope. This feature of the invention means that each time the source is attached to a new endoscope, the surgeon does not have spend time engaging in a radical resetting of the emitted light setting.

Moreover, this invention is further configured so that light source 536 automatically performs the feedback adjustments needed to be performed based on the type of endoscope 22 connected to it. Each time the light source 536 is attached to a different endoscope 22, medical personnel do not need to manually enter data that reflects this component change. Since a manual step is not performed, both the time takes to be performed and the potential for error during its execution are likewise eliminated.

An alternative circuit internal to cable 450 is now described by reference to FIG. 36. In this version of the invention, three conductors 64a extend from light end plug 452 to scope end plug 480. One of the conductors 64a is through plug 477 and connector 476 is connected to the 5 VDC voltage source internal to light source 536. The circuit also includes a 4-bit digital to analog converter 570. Converter 570 is housed in the scope end plug 480. In some versions of the invention, handle 480 is formed with an inner wall that defines a notch in which converter 570 is seated, (inner wall and notch not illustrated). The conductor 64a carrying the 5 VDC is connected to converter 570 to provide a reference voltage to the converter.

A branch extension of the conductor 64a that carries the 5 VDC signal is connected to one end of each of the reed switches 390. The opposed ends of reed switches 390 are each connected to a separate input pin of the converter 570. A second one of the conductors 64a extends from the ground pin of converter 570 to connector 476. This conductor 64a, through connector 476 and plug 477, is connected to the ground plane of the light source 536. The third conductor of 64a of this version of cable 450 extends from the analog signal outlet pin of converter 570. This conductor 64a, through connector 476 and plug 477, is connected to buffer 542 of the light source 536.

The adapter with which the above-described version of cable 450 is used is structurally very similar to previously described adapter 514. The only difference between versions of the adapters is that, in the currently described version, plural magnets 524 may be seated in the individual holes 522 of the adapter body base 518. The number of magnets 524, and the arrangements of the magnets is a function of the type of endoscope to which the adapter is intended to be coupled. In one embodiment of this version of the invention, endoscope type is defined by two variables. The first variable is the previously described outer diameter of the shaft 23. The second variable is the angle of the opening at the distal end of the shaft 23. By reference it should be understood that if the plane of the opening is perpendicular to the longitudinal axis of the shaft, the opening is considered to have a 0° angle.

The light source 536, the cable 450 and adapter 514 of the immediately above-described invention work in a manner similar to the previously described version of the invention. (However, there will be no need to provide a pull-up voltage through a resistor similar to resistor 540. Instead, the 5 VDC signal is, as previously discussed, applied to the components internal to cable 450.) The signal from buffer 542 is applied to analog-to-digital converter 544 internal to light source 536. The output signal of converter 544, which is representative of both whether or not a endoscope 22 is attached to the light source 536 and the type of endoscope, is applied to control processor 538. Based on this input signal, the basic setting module and feedback control module 562 and 564, respectively, are selectively executed by the control processor 538.

In the above-described version of the invention, adapter 514 can be provided with up to 4 magnets. Accordingly there are 15 possible arrangements of one to four magnets 524 relative to alignment pin 528. Converter 570 is capable of generating output signals at 16 different voltage levels. Thus, by the selective positioning of the magnets 524 in the adapter 514, this version of the invention can be used to, over a three conductor circuit, provide an indication of whether or not the light cable 450 is attached to one of 15 different types of endoscopes. The remaining voltage level, often the 0 volt level, is used to provide a no-scope connection state signal. The version of the light source 536 with which this version of cable 450 is used is configured to distinguish between 15 different types of endoscopes 22 and provided shutter positioning commands for each of these endoscopes.

Figure 37:
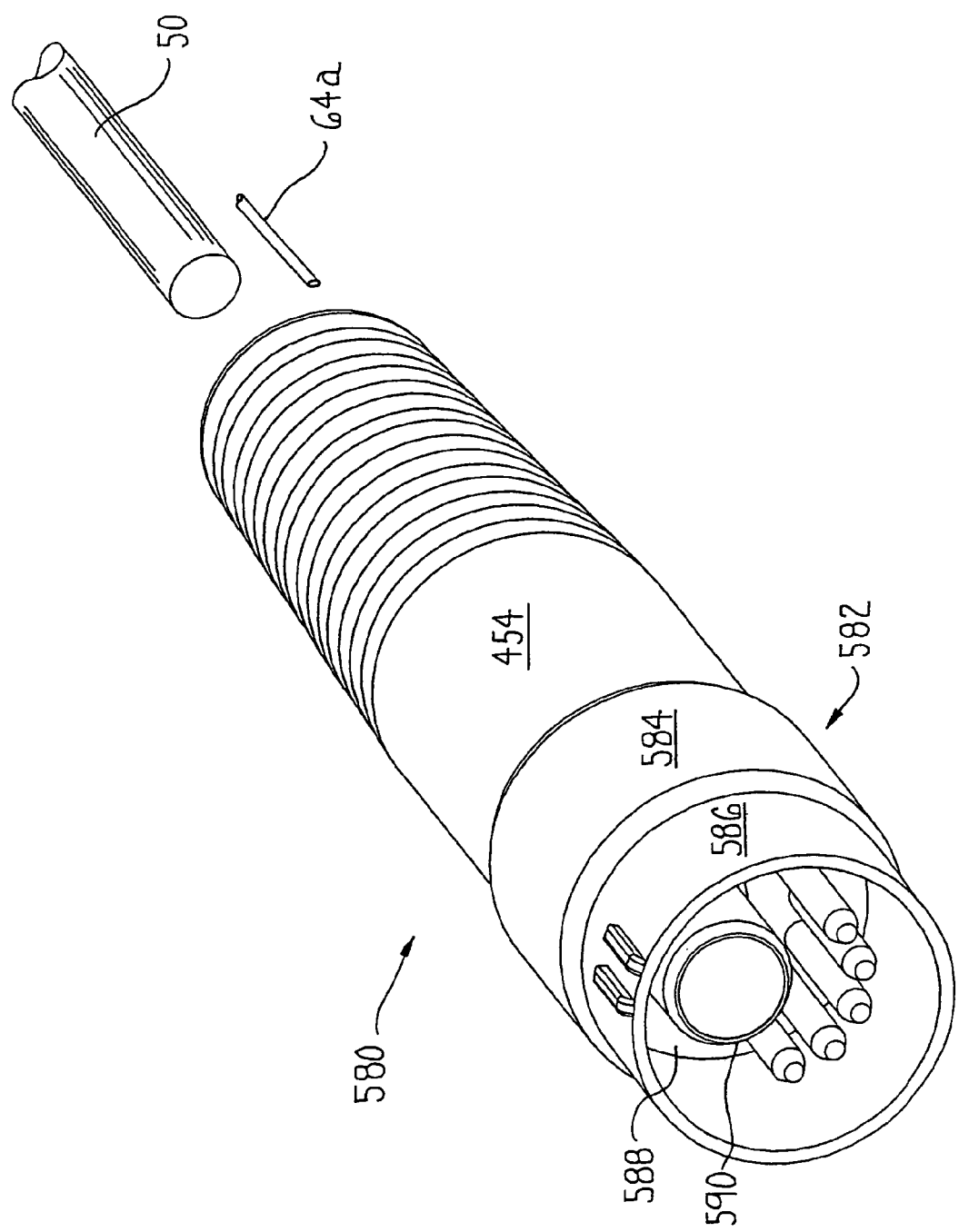
FIG. 37 is a perspective view of an alternative scope end plug of a fiber optic cable of this invention.

FIG. 37 illustrates an alternative light end plug 580 that can be fitted to cable 450. Plug 580 includes the previously described handle 454. The proximal end of core 50, tubing 52 and conductors 64a extend into handle 454. In the illustrated version of the invention, plug 580 is shown as being able to receive five conductors 64a (one shown). Plug 580 has an insert (not shown) similar to insert 456.

A metal cap 582 is fitted over the exposed proximal-facing end of the plug insert. Cap 582 has a wide diameter base 584 that is press fit otherwise secured over the exposed end of the plug insert. The cap 582 also has a ring shaped head 586 that is integral with and extends forward from base 584. There is a front face 588 that covers the base 584 and that is recessed relative to the proximal end of head 586. A tube like tip 590 extends forward from face 588. Tip 590, in the depicted version of plug 580, is axially offset from the longitudinal center axis of the plug. The proximal end of core 50 is seated in tip 590. Five spaced apart electrical contacts 592 extend forward from face 588. Each of the conductors 64a is connected to a separate one of the contacts 592. Plug 580 is dimensioned so that head 586 encloses tip 590 and contacts 592.

Cap 582 is further provided with two alignment ribs 594 are located are parallel to each other and are located on the outer wall of the head 586.

The complementary light source socket to which plug 580 is connected has a first, large diameter opening for receiving tip 590. The socket has five smaller diameter individual electrical sockets for receiving contacts 592. The socket also has notches for receiving alignment ribs 594. When the plug 580 is initially positioned in the light source socket, the alignment ribs first seat in their complementary notches. This alignment ensures that the tip 590 fits in its complementary bore and the contacts are received in their complementary sockets.

Figure 36:
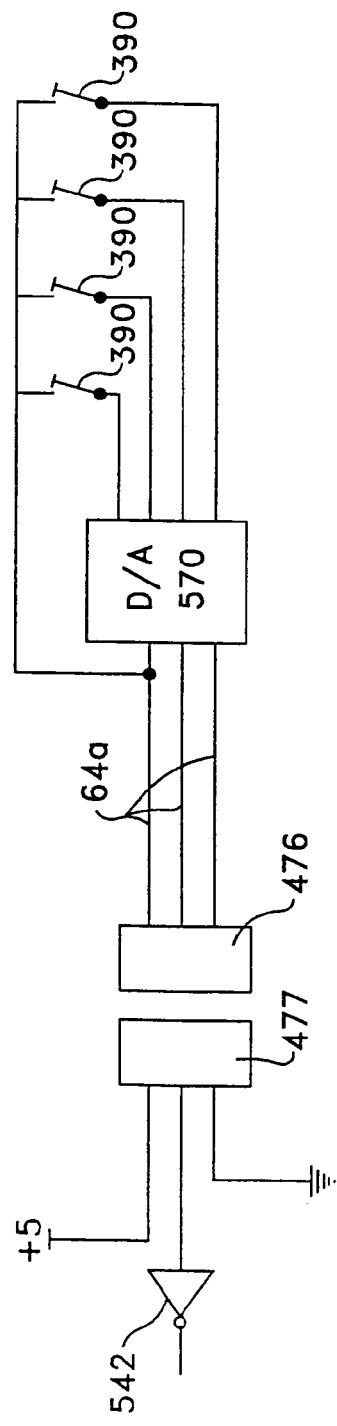
FIG. 36 is a schematic and block diagram of an alternative circuit internal to the cable of FIG. 29.

In versions of the cable 450 in which plug 580 is installed, reed switches may be connected together in the scope end plug 480 in the arrangement of FIG. 36. However, since there are four output conductors 64a extending from the cable 450, the need to provide the digital to analog converter internal to the cable is eliminated. Instead, conductors internal to the light source 536 can supply the signals present over cable conductors 64a directly to the control processor 538. Collectively, these signals provide multi-bit signal representative of the type of endoscope to which the light source is connected. An advantage of this version of the invention is that it eliminates the need to provide additional signal processing components the converters, to both cable 450 and light source 536.

An alternative construction of the invention is now described by initial reference to FIG. 34A. In this version of the invention, communications link 594, the link between the light source 536 and camera control unit 556 is a bi-directional communications link. More particularly, link 594 is the link over which there is bi-directional data exchange between light source control processor 538 and camera microcontroller 559. In this version of the invention, whenever, light source processor 538 receives a new scope-type signal indicating that the type of endoscope 22 attached to source 536 has been changed, processor 538 forwards data identifying the type of scope to microcontroller 559. These new data are sometimes referred to as a second scope-type signal.

Figure 38:
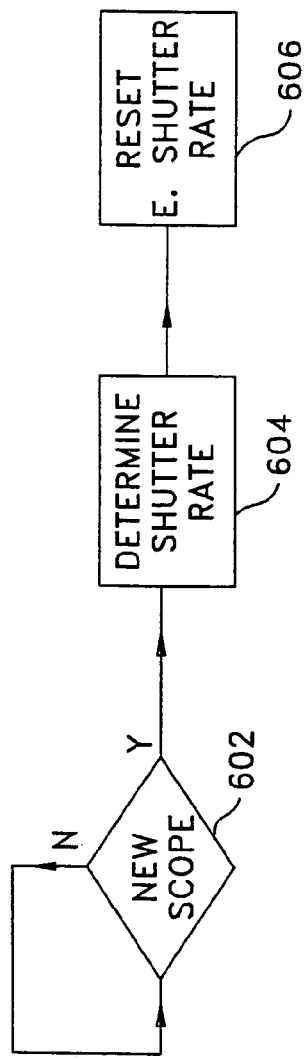
FIG. 38 is a flow chart of the process steps executed by the microcontroller internal to the camera of this invention.

Microcontroller 559 is configured to respond to the second scope-type signal as represented by the flow chart of FIG. 38. As represented by decision step 602, microcontroller 559 constantly monitors the data received from source 536 to determine if data indicating a new endoscope has been attached to the source 536 and camera 552. Once this event occurs, microcontroller 559 determines what the electronic shutter rate should be for the camera based on optical transmission characteristics of the new endoscope 22, step 604. This determination is made by reference to data in a memory 561 internal to the camera control unit 556 to which the microcontroller 559 is connected. Generally, as the diameter of the endoscope shaft 23 increase, the electronic scan rate increases.

Then, in step 606, the microcontroller 559 sends commands to the electronic shutter assembly 555 to reset the rate at which the assembly scans the charge coupled device 553. An advantage of this version of the invention is that the type-of-scope determination made by the light source 536 is used for more than facilitating the resting and subsequent adjustment of the light emitted by the light source. This data are also employed by the camera 552 to facilitate signal processing that ensures a high quality image representative of the surgical site will be presented. This version of the invention thus eliminates the need for medical personnel to, each time a new endoscope is connected to the camera 552, provide the camera control unit 556 with information reflective of this fact.

It should be realized that, in other embodiments of the above-described invention, the type-of-scope data may not be forwarded directly from the light source 536 to the camera 552. In some embodiments of the invention, both the light source 536 and camera 552 may be connected to central control unit, (not illustrated). Other devices in the surgical suite may be connected to this central control unit. The light source 536, upon determining that a new endoscope has been attached to it, is configured to transmit type-of-scope data describing the new endoscope to the central control unit. The central control unit, upon receipt of this data, generates and transmits to the camera 552 a data packet that indicates the type of scope to which it and the light source 526 are connected. The camera microcontroller 559, upon receipt of this data adjusts the electronic shutter rate as described above.

Also, in some versions of the invention, there may be a branch output line from analog-to-digital converter 544, or whatever component performs the scope-detect function. This branch line and a complementary external cable may serve as the link over which the type of scope signal is supplied to the camera microcontroller 559. An advantage of this construction of the invention is that it eliminates the need of having the light source control processor 538 serve as the unit which generates the type-of-scope signal to the camera 552.

Also, it should be understood that scope end plug 484 may function as the distal end plug for an alternative version of cable 124. In these versions of the invention, the stem section 140 and end cap 145 of light end plug 130 function as the conductive contacts through which the conductors and reed switches are connected to the type-of-scope detecting circuit internal to the light source.

It should be recognized that different features of the above described versions of the light source and complementary components of this invention may be arranged as desired.

It should be realized that, in other versions of the invention, the adapter can be provided with sensed elements different from magnets that provide an indication of the type of endoscope 22 with which the adapter is associated. For example, in some versions of the invention, elements that are transparent to light at selective wavelengths may be mounted to the adapter. In these versions of the invention, the scope-end plug of the fiber optic cable may carry both a light emitting member and a light-sensitive transducer. In other versions of the invention, an analog or digital electrical component may be fitted to the adapter. The particular component would be a function of the type of endoscope.

Alternatively, the component internal to the adapter could be a memory unit such as a ROM. In these versions of the invention, the data contained in the memory would either identify the type of endoscope or contain data used by the programs run on the control processor 538 to set the amount of light forwarded from source 536 to the endoscope. In these versions of the invention, the conductors internal to the fiber optical cable are physically connected to the component internal to the adapter.

Also, in some versions of the invention, instead of the magnets all generating magnetic fields of the same general strength, magnets of different strength may be provided. In this version of the invention the strength of the magnet or magnets is a function of the type of associated endoscope. In this versions of the invention, a Hall effect sensor is fitted to the scope end plug of the fiber optic cable. The level of the output signal from the sensor would provide both an indication of whether or not the cable is attached to endoscope and the type of endoscope to which the cable is attached.

Also, through the selective dimensioning of the endoscopes 22 and adapter bodies 516 these components are constructed with complementary physical features that ensure that each type-specific adapter can only be attached to the endoscope 22 with which it is to be associated.

It should likewise be understood that the sensed element may be permanently fixed to the endoscope. In these versions of the invention, the thickness of the member forming the light post 58 is expanded to accommodate the placement of the sensed element or elements. An advantage of this version of the invention is that it eliminates the need to provide a separate component, the adapter. Thus, this construction likewise eliminates the possibility that a type-specific adapter can be inadvertently attached to incorrect type of endoscope.

Moreover, in some versions of the invention, processor 538 may perform additional regulation of the light emitted by source 536 as a function of the scope-type signal. For example, depending upon the type of endoscope, the processor 538 may limit the amount of light emitted unless the medical personnel actuate an override switch. This feature of the invention can be used to prevent an endoscope from receiving large quantities of light that could potentially damage the internal components of the endoscope.

Figure 39:
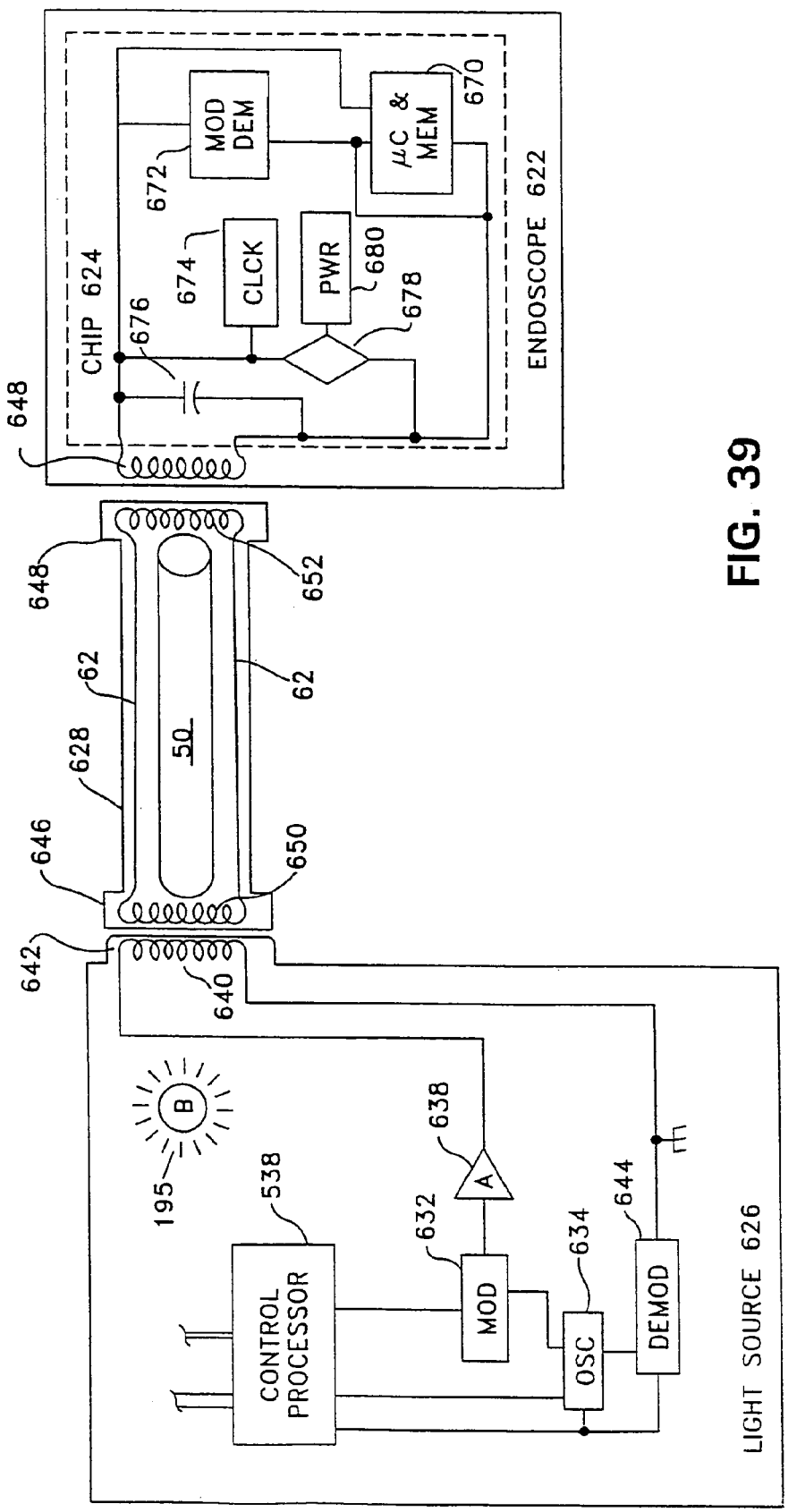
FIG. 39 is a block diagram of an alternative endoscope assembly of this invention.

Also, alternative members other than snap rings and surface threading may be used to facilitate the coupling of the adapter to the endoscope or the light cable to adapter. For example, spring biased clips and tongues may be employed. In these versions of the invention, small levers on the body of the adapter are depressed to facilitate the locking of and/or release of the adapter to and from the components to which it is connected. facilitate the FIG. 39 illustrates the basic structure of another endoscope assembly 620 of this invention. Assembly 620 includes an endoscope 622 in which an identification chip 624 is mounted, Chip 624, as described below, functions as the previously described ROM that contains data that identifies the type of endoscope with which the chip 624 is integral or data, control variables, used by a light source 626 regulate the emission of light from the source. The data in chip 626 is also used by the camera control unit microcontroller 559 to regulate the processing of signals generated by the camera head 554 so that they can be used to present a display image. The data in chip 624 is written out to the complementary light source 626 through conductors 62 in fiber optic cable 628.

Light source 626 of this version of this invention has a control processor 538a similar in function to previously described control processor 538. FIG. 39 illustrates how light source 626 includes lamp 195. While not illustrated, it should be understood that light source 626 contains the previously described shutter 34, motor 37, motor controller 292, and ROM 546. There are also controls, such as knob 548 for manually setting the quantity of light emitted by source 626. Though also not illustrated, it should be understood that control processor 538a is connected to the camera control unit 556. Control processor 538a forwards to the camera control unit 556 the same scope-identifying information control processor 538 forwards to the camera control unit.

Light source 626 also includes a modulator (MOD) 632. Modulator 632 modulates digital signals output in serial form by control processor 538a so they can be inductively transferred to endoscope chip 624. In one preferred version of the invention, modulator 632 receives a fixed-frequency signal from an oscillator 634 internal to the light source 626. In one version of the invention, the signal produced by the oscillator 634 is at a frequency of 125 Khz. In another preferred version of the invention, the carrier signal produced by oscillator 634 is at 13.5 MHz.

Modulator 632, based on the bit stream produced by control processor 538a, engages in selective amplitude shift keying (ASK) of the carrier signal. In one form of amplitude shift keying, based on the 1's and 0's pattern the forms the bit stream selectively transmits/stops transmitting the carrier signal so as to produce a set of variable length rectangular pulses. The amplitude shift keyed signal generated by modulator 632 is amplified by an amplifier 636 internal to the control console 28. The output signal from amplifier 638 is applied to one end of a coil 640 fitted to a light source socket 642 to which the proximal end of cable 628 is attached.

The end of coil 640 opposite the end to which amplifier 638 is connected is tied to a demodulator (DEMOD) 644 internal to the light source 626. This end of light source coil 640 is also tied to a ground internal to the light source 626. Demodulator 644 receives the signal that is coupled to handpiece coil 640, demodulates the signal, and applies the output bit stream to control processor 538a. A typical demodulator may include a product detector to which the carrier signal is applied from oscillator 634. The output from the detector, which is multiplication of the signal from the oscillator 76 and the coil 66, is applied to a low-pass filter, also part of the demodulator 644. The output signal from the low pass filter is a bit stream that is applied to the controller 70. In FIG. 39 oscillator 634 is also shown as connected to control processor 538a. This is because the signal produced by the oscillator is also used to regulate the writing out of the bit stream that is applied to the modulator 632 and the reading in of the bit stream generated by the demodulator 644.

As mentioned above, coil 640 is mounted in the socket 642 to which fiber optic cable 628 is attached. In one preferred version of the invention, socket is constructed so as to be similar to previously described socket 202 (FIGS. 18 and 19). However, socket 642 will not have a contact ring formed of metal. Instead, the contact ring of socket 642 will be formed of plastic. Coil 640 is embedded in the contact ring so as to surround the opening in the ring through which the light end plug of fiber optic cable 628 is inserted. Flexible insulated wires that extend from the coil 640 connect the coil to its complementary circuit components internal to the body of the light source 626.

Fiber optic cable 628 of this embodiment of the invention includes the previously described core 50, tubing 52 and conductors 62. The proximal end of the cable 628 is provided with a light end plug 646. The distal end of the cable is provided with a scope end plug 648. A light end coil 650 is mounted in light end plug 646. A scope end coil 652 is mounted in scope end plug 648. Conductors 62 connect the opposed ends of the coils 650 and 652 together.

Figure 40:
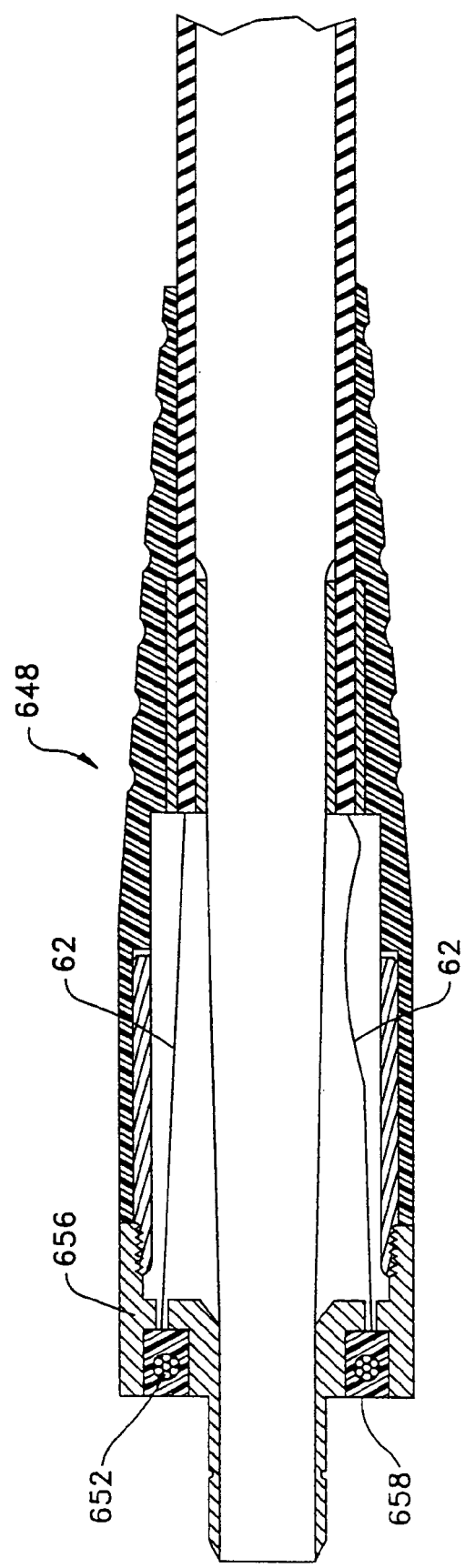
FIG. 40 is cross sectional view of a light end plug of the assembly of FIG. 39.

Scope end plug 648, as seen in FIG. 40, has many components similar to those contained in scope end plug 132 (FIG. 14). However, scope end plug 648 has a scope end tip 656 that is not provided with contacts. Instead, an annular plastic ring 658 is fitted in a circular recess formed in the base of scope end tip 656. Scope end coil 652 is embedded in ring 658. The opposed ends of coil 652 extend through ring 658 and are connected to conductors 62.

Figure 13:
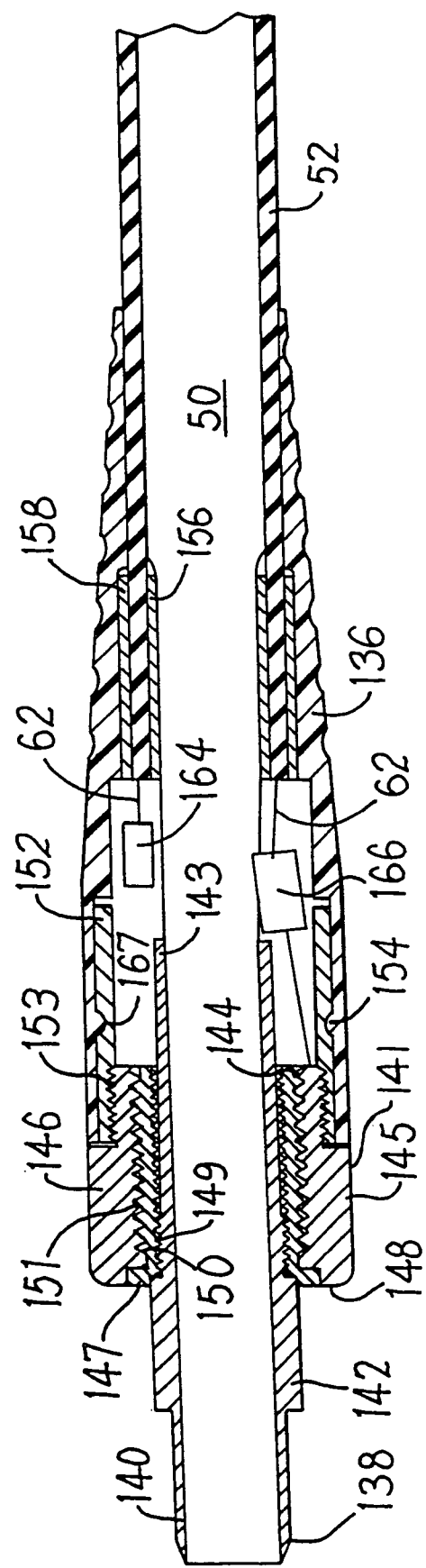
FIG. 13 is a cross-sectional view of the light source plug of the cable of FIG. 12.
Figure 15:
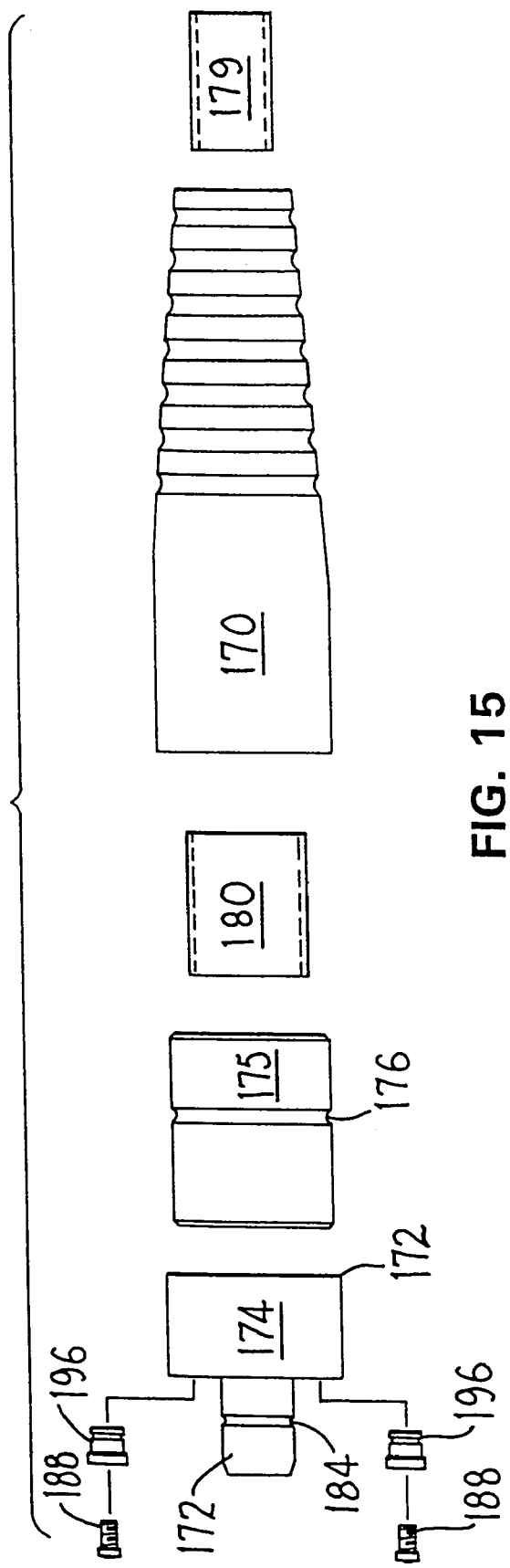
FIG. 15 is an exploded view of the components forming the scope-end plug of the cable of FIG. 12.

Light end plug 646 is similar to previously described light end plug 130 (FIGS. 12 and 13). However, light end plug 646 is formed with a unitary tip, similar to scope end tip 656, that performs the same structural functions as previously described tip 138 and cap 145. The wide diameter base portion of the light end tip is formed with a notch around its outer perimeter. A plastic ring is seated in this notch. Light end coil 650 is embedded or otherwise disposed in this ring. More particularly, the contact ring of light source socket 642 and the ring of the light end plug 646 are collectively positioned so that when the light end plug is seated in the socket, coils 640 and 650 will be in sufficient proximity to each other that signals will be inductively transferred between the coils.

Figure 41:
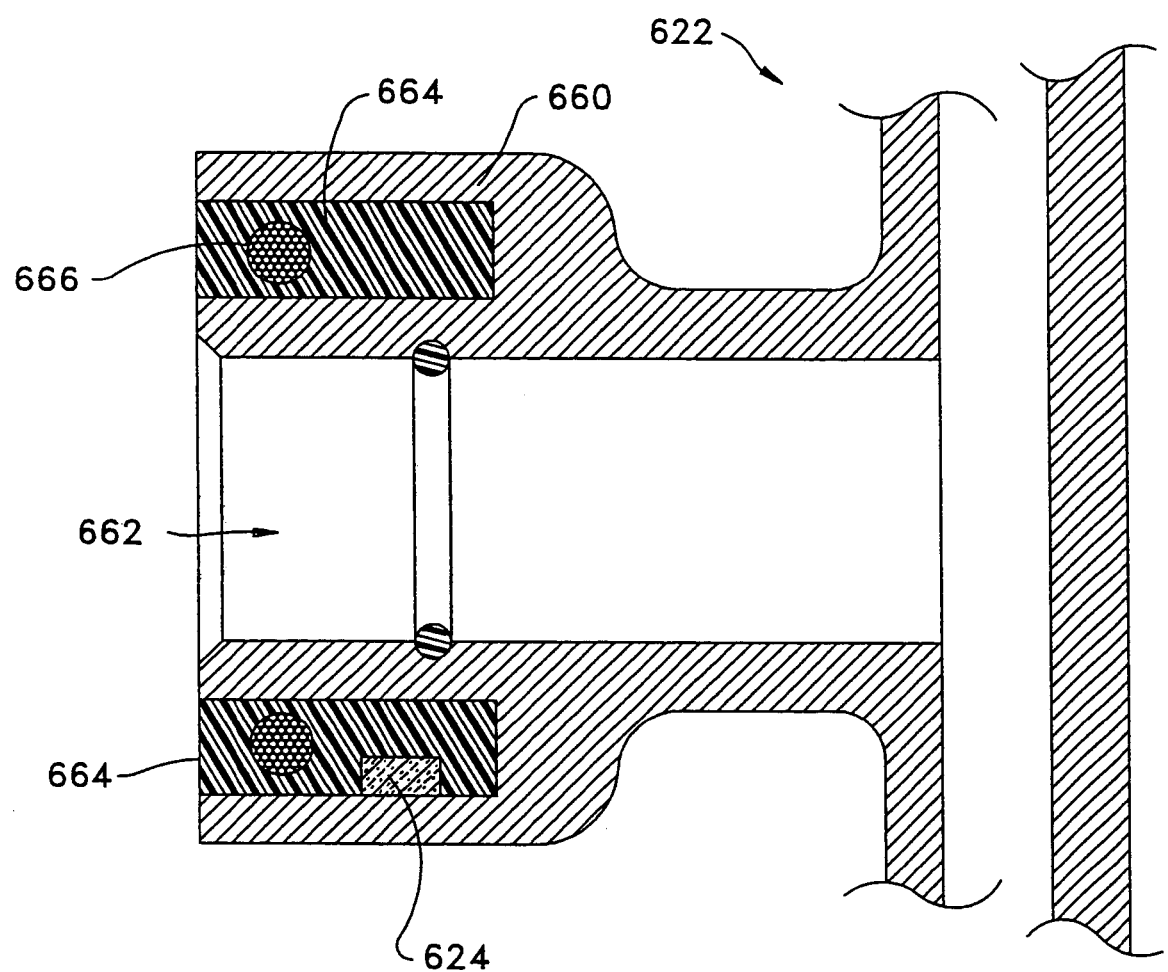
FIG. 41 is a cross sectional view of a light post of an endoscope of the assembly of FIG. 39.

FIG. 41 illustrates the light post 660 of endoscope 622 and how chip 624 is fitted to the light post. Light post 660 is a sleeve-like structure with a bore 662 for receiving the tip end of scope end plug 648. The light post 660, like the rest of the endoscope 622, is formed of stainless steel. A plastic sleeve 664 is seated in a groove formed in the proximal facing face of the light post 660. Chip 624 is embedded in sleeve 664. Also embedded in sleeve 664 is a coil 666. Coil 666 is located towards the proximal facing face of sleeve 664. More particularly, scope end plug 648 and endoscope light post 660 are collectively constructed so that when cable 628 is attached to the endoscope 622, coils 652 and 666 will be in sufficient proximity so as to inductively transfer signals therebetween.

Returning to FIG. 39, the sub-circuits fabricated on chip 624 are now described. The identification chip 624 includes a small controller and an electronically programmable memory (µC&MEM) 670. Controller/memory 670 is capable of storing approximately 2 k bits of data. The controller integral with controller/memory 670 is capable of controlling the writing of data into its complementary memory section and the writing out of the contents of the memory. There is also a modulator/demodulator (MOD DEM) 672 fabricated integrally into chip 624. Modulator/demodulator 672 contains the components necessary to demodulate the ASK signal coupled to coil 666 and apply the resultant bit stream to controller/memory 670. Modulator/demodulator 672 also accepts the bit stream output from the controller/memory 670 and produces an ASK modulated signal based on this bit stream. A clock 674 fabricated into chip 624 produces a clock signal that modulator demodulator 672 uses as a basis for producing a carrier signal produced an ASK modulated signal.

A capacitor 676 is also fabricated integrally with chip 62. More particularly, chip 624 is designed so that coil 666 connected across the opposed ends of capacitor 676. A switch 678 integral with chip 624 is tied across capacitor 676. When a signal is applied to chip 624 through coil 666, the energy in the high portion of the signal is stored in capacitor 876. This energy is applied through switch 678 to a power regulator 680 as an energization signal. The power regulator 680 supplies this energization signal to the other sub-circuits internal to the chip 624. (Connections between power regulator 680 and other sub-circuits internal to chip 624 not shown.)

Controller/memory 670 contains a data field in which is stored data identify the type of endoscope with which chip 624 is integral.

Operation of the endoscope assembly 620 of this invention is now explained with reference to the flow chart of FIG. 42. Once the light source 626 is actuated, control processor 538a periodically generates a read request to endoscope chip 624, step 680. The digital signal forming this request is converted into an ASK signal by modulator 632 and inductively coupled through coils 640 and 650 to fiber optic cable conductors 62. Coils 652 and 666 apply the signal to chip 624. In some versions of the invention, step 680 is executed once every 1 to 10 seconds. More specifically, step 680 is executed more frequently than the shortest time gap that it would take a surgeon to switch endoscopes in a patient.

Figure 42:
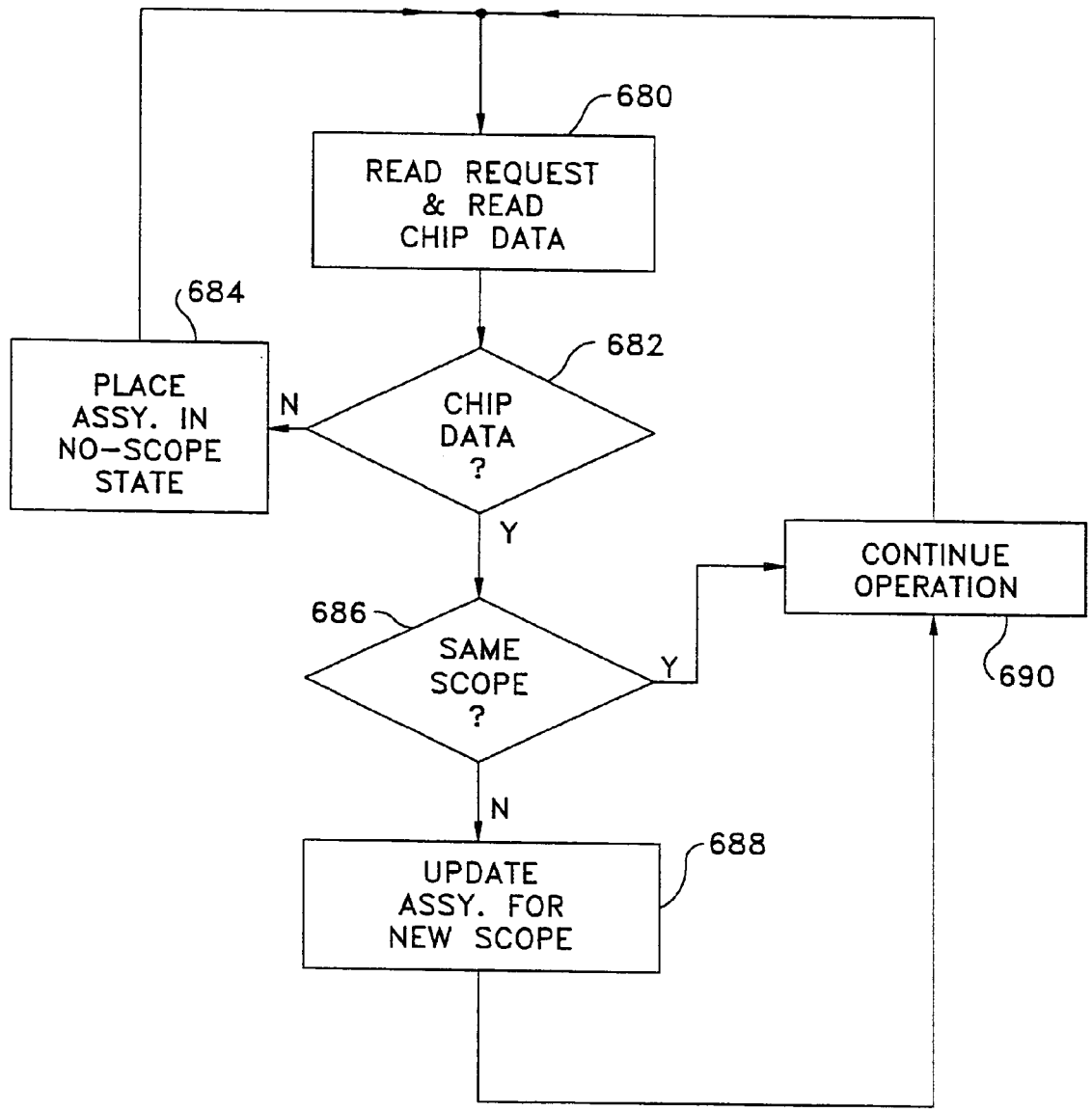
FIG. 42 illustrates some of the process steps executed by the light source of the assembly of FIG. 39.

In response to the read request, chip controller/memory 670 reads out the contents of its stored memory to light source control processor 538a, depicted in FIG. 42 as part of step 680.

However, there may instances when the fiber optic cable is not connected to an endoscope. The control processor 538a determines if this is the case by determining if, in fact it receives data from the endoscope chip 624 in response to the read request, step 682. If no data are received, controller processor 538a recognizes the assembly 620 as being in a state in which the cable 628 is not attached to an endoscope. If the assembly 620 is in this state, control processor 538a places the light source in the no-scope mode, step 684. In other words, basic setting module 562 is executed for the no-scope state. As part of step 684, controller processor 538a sets an internal flag field in RAM memory to indicate the assembly is in the no-scope state.

If, in step 682, it is determined that data was written from the endoscope chip 624 to the light source 626, control processor 538a executes step 686. In step 686, control processor 538a determines whether or not the data indicates that the endoscope now connected to the endoscope is the same type of endoscope that was previously connected. If this comparison indicates that a new endoscope was attached, or this is the first endoscope that is attached after the assembly was in the no-scope state, control processor 538a proceeds to step 688. In step 688, controller processor 538a executes the previously described basic setting module 562. Module 562 is executed based on the type of endoscope data control processor 538a received from the endoscope chip 624. Also, as part of step 688, control processor 538a writes into its RAM an indication of the type of endoscope 622 attached to light source 626.

Also, as part of step 688, control processor 538a forwards a data packet to the camera control unit 556 identifying the type of endoscope that has been just attached to the light source 626. As previously discussed, camera control unit 556 then configures itself to process the output signals received from the camera head 554 based on the to which the camera head is attached.

Control processor 538a then allows the assembly 620 to operate normally, step 690. During step 690, feedback control module 564 is executed when necessary. Module 564 adjusts the light emitted by source 626 based on the type-of-endoscope data received from chip 624.

As discussed above, the reading of data from chip 624 is performed periodically, even after it has been determined that an endoscope is attached to the light source. Steps 680 and 682 are repeatively executed after step 684 is executed to place the assembly 620 in the no-scope state. Steps 680 and 682 are repeatively performed in order to determine if the endoscope has been disconnected from the light source and/or a different endoscope installed. Accordingly, there may be sometimes when, in step 686 it is determined that one endoscope is still continually attached to the endoscope. When control processor 538a determines that this is the state of the system, the control processor will simply continue to repeatively execute steps 690 and 680.

In some versions of this invention, the chip 624 integral with the endoscope may contain data indicating more than just endoscope type. The chip may contain data indicating variables like mechanical shutter setting and the speed at which the shutter motor should be operated for that endoscope. If this information is contained in chip 624, control processor 538a uses these variables for executing modules 562 and 464. Similarly chip 624 can include data that indicates the appropriate electronic shutter setting for the camera with which it is used. If this data are read from the chip, control processor 538a forwards it to the camera control unit microcontroller 559. Microcontroller 559 then regulates the electrical processing of the signals received from the camera head based on the shutter setting data received from chip 624.

Alternative embodiments of the above-described version of endoscope assembly 620 are possible.

For example, in some versions of the invention ring 688 of scope end plug 648 in which coil 652 is seated may not be mounted to the plug to form an outer surface of the plug. Instead, the ring with coil 652 embedded therein may be mounted in the plug. A very thin section of the scope end tip covers the ring. Similarly, sleeve 664 in which coil 666 is housed may be located inside the endoscope light post in which it is mounted. An advantage of these embodiments of the invention is that the plastic forming these members is not directly exposed to the rigors of autoclave sterilization.

In other versions of the invention, the memory within chip 624 may contain more data than the data identify the type of endoscope with which it is integral. For example, the memory may contain a data field in which data are stored indicating the maximum amount of light that can be applied to the associated endoscope. The light source with which the endoscope is used has a transducer that measures the light emitted from the to source socket 642. A signal representative of this light level is provided to the control processor 538a. The control processor uses the data representative of the maximum light that can be applied to the endoscope as well as the emitted light signal to regulate the setting of shutter 34 so as to prevent the light source from emitting more light than it is appropriate to apply through the endoscope.

The chip 624 may also include a data field indicating the rate at which the light applied to the endoscope should be adjusted. Control processor 538a and motor controller 292 use this data to regulate the speed at which the motor 37 rotates shutter 34 to new settings.

Chip 624 may also store data that is used by the camera 552 to regulate the processing of the signal generated by camera head transducer (CCDs) 553. These data are forwarded to the camera control unit 556 by the light source 626 whenever the light source control processor 538a forwards data to the camera control unit indicating that a new light endoscope has been attached to the light source.

One piece of data that, in some versions of the invention it is useful to provide to the camera control unit 556 is the serial number specific to the attached endoscope. Based on a look-up table internal to the camera control unit, microcontroller 559 can determine whether or not that camera has been white balanced for the endoscope. If there was a previous while-balance for that endoscope, the white balance values stored previously can be employed by the white balance circuit to selectively amplify/attenuate the individual red/green/blue signals received from the CCD 553 in order to present an image on display 558 with the appropriate color levels.

In "white balancing", the endoscope is directed at a white object. This allows the white balance circuit internal to the camera control unit 556 to set the appropriate amplification/attenuation levels for the individual red/green/blue signals. Individual amplifiers perform the actual amplification of the individual red/green/blue signals. The red/green/blue signals may be amplified when they are either in their analog or digital states. As discussed above in this version of the invention, after an endoscope is first subjected to white balancing, its serial number and the white balance levels are stored in the camera control unit look-up table. This look-up table maybe part of camera control unit memory 561 or in a separate read/write memory internal to the camera control unit. Having the ability to recall the white balance levels for a particular endoscope eliminates the need to have to white balance a particular endoscope each time it is used with the same camera 552. Specifically, if the white balance data for a particular endoscope is present microcontroller 559, based on the recalled data, sets the amplification/attenuation levels for the individual red/green/blue amplifiers. If the white balance data is present, microcontroller 559 causes a message to be presented on display 558 to inform the surgeon that there is no need to white balance the assembly 620 for the newly attached endoscope. If there camera control unit does not have previously-stored data white balance data stored for the newly attached endoscope, the microcontroller presents a message on the display informing the surgeon that the assembly must be white balanced for this endoscope. The white balance data for the endoscope, along with its serial number, is then stored in the look up table for later use.

The chip memory must also contain a data field in which data indicating whether or not there is a window covering on the endoscope and the type of window covering. This data are also used by the camera control unit to process the images received from the CCD 553.

Chip 624 may also contain a data field with data indicating the area setting, the field of view of the endoscope. These data are employed by the CCD to regulate the generation of video signals so that a representation of appropriate size, usually full screen, of the image captured by the endoscope is presented on the display 558.

Therefore, it is the object of the appended claims to cover all such modifications as common within the true spirit and scope of this invention.

What is claimed is:

1. A fiber optic cable for applying light generated by a light source to an endoscope, said fiber optic cable comprising:
   a light source plug for connection to the light source;
   a core formed of optically transmissive material that extends from the light source plug;
   a scope end plug attached to an end of the core opposite the end to which the light source is attached;
   conductors that extend from the light source plug;
   a sensor assembly is disposed in the scope end plug for determining the type of endoscope to which the fiber optic cable is attached and said sensor assembly applies a variable voltage analog signal over the conductors to the scope end plug.

2. The fiber optic cable of claim 1, wherein said sensor assembly includes a plurality of magnetically sensitive switches that open/close as a function of the presence/absence of magnets integral with the endoscope.

3. The fiber optic cable of claim 2, wherein said sensor assembly includes a digital signal converter to which said switches are attached and said digital signal converter generates the variable voltage signal as a function of the open/closed states of the switches.

4. The fiber optic cable of claim 2, wherein said sensor assembly includes a plurality of resistors that form a resistor circuit and said switches are connected to said resistors to establish the resistance of said resistor circuit as a function of the open/closed state of said switches.

5. A fiber optic cable for applying light generated by a light source to an endoscope, said fiber optic cable comprising:
   a light source plug for connection to the light source;
   a core formed of optically transmissive material that extends from the light source plug;
   a scope end plug attached to an end of the core opposite the end to which the light source is attached, said scope end plug shaped to be removably coupled to a socket integral with the endoscope;
   conductors that extend from the light source plug to said scope end plug;
   a plurality of magnetically-sensitive switches disposed in said scope end plug that open/close as a function of the presence/absence of magnets associated with the endoscope; and
   a monitoring circuit to which said conductors and said switches are attached, said monitoring circuit configured to output a variable level analog signal as a functidn of the open/closed states of said switches.

6. The fiber optic cable of claim 5, wherein said monitoring circuit includes a digital-to-analog converter to which said switches are attached, and said digital-to-analog converter outputs the variable level analog signal as a function of the open/closed states of said switches.

7. The fiber optic cable of claim 6, wherein said switches collectively provide said digital-to-analog circuit with a multi-bit input signal and said digital-to-analog circuit generates the variable level analog signal as a function of a binary value established by the open/closed states of said switches.

8. The fiber optic cable of claim 5, wherein said monitoring circuit comprises a plurality of resistors that form a resistor circuit and said switches are connected to said resistors to establish the resistance of said resistors as a function of the open/closed state of said switches.

9. An endoscope assembly including:
an endoscope, the endoscope having an indicator that contains identifier data specific to the endoscope;
a camera including: a camera head attached to said endoscope for receiving images through the endoscope, said camera head configured to generate camera signals representative of the images received by said camera head; and a camera control unit attached to said camera head for receiving the camera signals, said camera control unit having an electronic assembly that processes the camera signals to produce display signals representative of the images received by the camera head and the electronic assembly produces the display signals based on the type of endoscope attached to said camera head;
an assembly for supplying the data stored in the endoscope indicator to the camera control unit;
a memory internal to said camera control unit in which endoscope-specific identifiers are stored for endoscopes previously connected to said camera head and the camera control unit and calibration data for the previously-connected endoscopes; and
a controller integral with said camera control unit electronic assembly to which the endoscope specific identifier for the endoscope attached to said camera head is applied and said controller is configured to:
determine, by reference to the endoscope specific identifier and the data in said memory, if the endoscope was previously connected to the camera head;
if the endoscope was previously attached to said camera head, retrieve from said memory the calibration data for the endoscope and to control the other components of the electronic assembly so that the electronic assembly produces the display signals based on the retrieved calibration data for the endoscope; and
if the endoscope was not previously attached to said camera head: forcing said camera control unit into a calibration sequence for the endoscope to obtain calibration data for that endoscope; control the other components of the electronic assembly so that the electronic assembly produces the display signals based on the newly obtained calibration data for the endoscope; and storing in said memory the endoscope-specific identifier and the newly obtained calibration data for the endoscope.

10. The endoscope assembly of claim 9, wherein:
said endoscope indicator is attached to a light post on said endoscope through which light is introduced into the endoscope;
a light source is provided for generating light for application to the endoscope, wherein said light source is connected to the camera control unit;
a fiber optic cable connects said light source to said endoscope light post, wherein said fiber optic cable contains a read device for reading the data from the endoscope indicator;
a decoder is disposed in said light source and connected to said fiber optic cable read device for receiving the data from said endoscope indicator and said decoder, based on the data from said endoscope indicator, generates a signal for application to said camera control unit controller containing the endoscope-specific identifier.

* * * * *

UNITED STATES PATENT AND TRADEMARK OFFICE
CERTIFICATE OF CORRECTION

| | | |
|---|---|---|
| PATENT NO. | : 7,018,331 B2 | |
| APPLICATION NO. | : 10/343375 | |
| DATED | : March 28, 2006 | |
| INVENTOR(S) | : Huei Liang Chang et al. | |

It is certified that error appears in the above-identified patent and that said Letters Patent is hereby corrected as shown below:

Title page,

Item [75] change
"[75]  Inventors: Huei Liang Chang, Milpitas, CA (US); Richard A. Beutter, San Diego, CA (US)"
to -- [75]  Inventors: Huei Liang Chang, Milpitas, CA (US); Richard A. Beutter, Lantana, TX (US); YanPeng Ng, Santa Clara, CA (US) --.

Signed and Sealed this

Ninth Day of January, 2007

JON W. DUDAS
*Director of the United States Patent and Trademark Office*